(12) United States Patent
Aertgeerts et al.

(10) Patent No.: US 7,759,339 B2
(45) Date of Patent: Jul. 20, 2010

(54) HYDROXYSTEROID DEHYDROGENASE INHIBITORS

(75) Inventors: Kathleen Aertgeerts, San Diego, CA (US); Nancy K. Brennan, Boston, MA (US); Sheldon X. Cao, San Diego, CA (US); Edcon Chang, San Diego, CA (US); Andre A. Kiryanov, San Diego, CA (US); Yan Liu, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 963 days.

(21) Appl. No.: 11/392,297

(22) Filed: Mar. 28, 2006

(65) Prior Publication Data

US 2006/0223829 A1 Oct. 5, 2006

Related U.S. Application Data

(60) Provisional application No. 60/667,297, filed on Mar. 31, 2005.

(51) Int. Cl.
*C07D 241/04* (2006.01)
*C07D 295/00* (2006.01)
*C07D 413/12* (2006.01)
*A61K 31/496* (2006.01)
*A61K 31/445* (2006.01)

(52) U.S. Cl. ............ 514/224.2; 514/230.5; 514/253.06; 514/253.07; 514/252.13; 544/49; 544/105; 544/359; 544/363

(58) Field of Classification Search ................ 544/49, 544/105, 359, 363; 514/224.2, 230.5, 253.06, 514/253.07, 252.13
See application file for complete search history.

(56) References Cited

U.S. PATENT DOCUMENTS

| | | | |
|---|---|---|---|
| 6,368,816 B2 | 4/2002 | Walker et al. | |
| 6,376,506 B1 * | 4/2002 | Broka et al. | 514/292 |
| 6,730,690 B2 | 5/2004 | Olson et al. | |
| 6,849,636 B2 | 2/2005 | Waddell et al. | |
| 6,875,782 B2 | 4/2005 | Cheng et al. | |
| 2003/0130258 A1 | 7/2003 | Kurz et al. | |
| 2003/0130279 A1 | 7/2003 | Kurz et al. | |
| 2003/0130318 A1 | 7/2003 | Barf et al. | |
| 2003/0148987 A1 | 8/2003 | Morris et al. | |
| 2003/0166689 A1 | 9/2003 | Kurz et al. | |
| 2003/0176476 A1 | 9/2003 | Barf et al. | |
| 2003/0198965 A1 | 10/2003 | Freier | |
| 2003/0199501 A1 | 10/2003 | Nilsson et al. | |
| 2003/0199553 A1 | 10/2003 | Gammill et al. | |
| 2004/0048912 A1 | 3/2004 | Olson et al. | |
| 2004/0063700 A1 | 4/2004 | Cheng et al. | |
| 2004/0063762 A1 | 4/2004 | Cheng et al. | |
| 2004/0106664 A1 | 6/2004 | Olson et al. | |
| 2004/0133011 A1 | 7/2004 | Waddell et al. | |
| 2004/0143124 A1 | 7/2004 | Vicker et al. | |
| 2004/0147494 A1 | 7/2004 | Potter et al. | |
| 2004/0224996 A1 | 11/2004 | Barf et al. | |
| 2005/0009821 A1 | 1/2005 | Pyring et al. | |
| 2005/0070720 A1 | 3/2005 | Balkovec et al. | |
| 2005/0085472 A1 | 4/2005 | Tanaka et al. | |
| 2005/0118263 A1 | 6/2005 | Walker et al. | |
| 2005/0119312 A1 | 6/2005 | Cheng et al. | |
| 2005/0148631 A1 | 7/2005 | Cheng et al. | |
| 2005/0154038 A1 | 7/2005 | Waddell et al. | |
| 2005/0171161 A1 | 8/2005 | Fong et al. | |
| 2005/0192310 A1 | 9/2005 | Gavai et al. | |
| 2005/0208658 A1 | 9/2005 | Castonguay | |
| 2005/0227987 A1 | 10/2005 | Vicker et al. | |
| 2005/0228038 A1 | 10/2005 | Vander Jagt et al. | |
| 2005/0239853 A1 | 10/2005 | Barf et al. | |
| 2005/0245532 A1 | 11/2005 | Hoff et al. | |
| 2005/0245533 A1 | 11/2005 | Hoff et al. | |
| 2005/0245534 A1 | 11/2005 | Link et al. | |
| 2005/0245745 A1 | 11/2005 | Link et al. | |
| 2005/0250776 A1 | 11/2005 | Barf et al. | |
| 2005/0256159 A1 | 11/2005 | Barton et al. | |
| 2005/0261290 A1 | 11/2005 | Cheng et al. | |
| 2005/0261292 A1 | 11/2005 | Antel et al. | |
| 2005/0261302 A1 | 11/2005 | Hoff et al. | |
| 2005/0272036 A1 | 12/2005 | Barton et al. | |

(Continued)

FOREIGN PATENT DOCUMENTS

EP 0251784 A 1/1988

(Continued)

OTHER PUBLICATIONS

Database CA [Online] Chemical Abstracts Service, Columbus Ohio, US; Komoto, Teruo et al.: "Preparation of piperazine-containing arylamide analogs as cardiovascular agents" XP002396840. retrieved from STN Database accession No. 1993:625978 abstract, (1993).

(Continued)

*Primary Examiner*—Kahsay T Habte
(74) *Attorney, Agent, or Firm*—Mitchell R. Brustein; David J. Weitz

(57) ABSTRACT

Compounds, pharmaceutical compositions, kits and methods are provided for use with hydroxysteroid dehydrogenases that comprise a compound selected from the group consisting of:

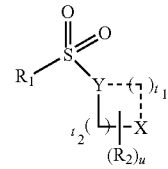

wherein the variables are as defined herein.

33 Claims, 1 Drawing Sheet

U.S. PATENT DOCUMENTS

| | | | |
|---|---|---|---|
| 2005/0272793 A1 | 12/2005 | Goto et al. |
| 2005/0277647 A1 | 12/2005 | Link et al. |
| 2005/0277649 A1 | 12/2005 | DeGraffenreid et al. |
| 2005/0277665 A1 | 12/2005 | Fan et al. |
| 2005/0282858 A1 | 12/2005 | Yao et al. |
| 2005/0288271 A1 | 12/2005 | DeGraffenreid et al. |
| 2005/0288308 A1 | 12/2005 | Amrien et al. |
| 2005/0288317 A1 | 12/2005 | Yao et al. |
| 2005/0288329 A1 | 12/2005 | Yao et al. |
| 2005/0288338 A1 | 12/2005 | Yao et al. |
| 2006/0004049 A1 | 1/2006 | Yao et al. |
| 2006/0009471 A1 | 1/2006 | Yao et al. |
| 2006/0009491 A1 | 1/2006 | Yao et al. |

FOREIGN PATENT DOCUMENTS

| | | |
|---|---|---|
| EP | 0626369 A | 11/1994 |
| WO | WO 01/30383 A2 | 5/2001 |
| WO | WO 01/30383 A3 | 5/2001 |
| WO | WO 01/90090 A1 | 11/2001 |
| WO | WO 01/90091 A1 | 11/2001 |
| WO | WO 01/90092 A1 | 11/2001 |
| WO | WO 01/90093 A1 | 11/2001 |
| WO | WO 01/90094 A1 | 11/2001 |
| WO | WO 02/08179 A1 | 1/2002 |
| WO | WO 02/072084 A2 | 9/2002 |
| WO | WO 02/072084 A3 | 9/2002 |
| WO | WO 02072085 A1 | 9/2002 |
| WO | WO 02072085 A3 | 9/2002 |
| WO | WO 03/020303 A1 | 3/2003 |
| WO | WO 03/043999 A1 | 5/2003 |
| WO | WO 03/044000 A1 | 5/2003 |
| WO | WO 03/044009 A1 | 5/2003 |
| WO | WO 03/059267 A2 | 7/2003 |
| WO | WO 03/065983 A2 | 8/2003 |
| WO | WO 03/076422 A | 9/2003 |
| WO | WO 03/086410 A1 | 10/2003 |
| WO | WO 03/088921 A2 | 10/2003 |
| WO | WO 03/104207 A2 | 12/2003 |
| WO | WO 03/104208 A1 | 12/2003 |
| WO | WO 2004/004655 A2 | 1/2004 |
| WO | WO 2004/004665 A2 | 1/2004 |
| WO | WO 2004/004665 A3 | 1/2004 |
| WO | WO 2004/027047 A2 | 4/2004 |
| WO | WO 2004/033427 A1 | 4/2004 |
| WO | WO 2004/037251 A1 | 5/2004 |
| WO | WO 2004/056744 | 7/2004 |
| WO | WO 2004/056745 A2 | 7/2004 |
| WO | WO 2004/058730 A2 | 7/2004 |
| WO | WO 2004/058741 A1 | 7/2004 |
| WO | WO 2004/065351 A1 | 8/2004 |
| WO | WO 2004/089367 A | 10/2004 |
| WO | WO 2004/089470 A | 10/2004 |
| WO | WO 2004/103980 A1 | 12/2004 |
| WO | WO 2004/106294 A2 | 12/2004 |
| WO | WO 2004/108686 A2 | 12/2004 |
| WO | WO 2004/112779 A1 | 12/2004 |
| WO | WO 2004/112781 A1 | 12/2004 |
| WO | WO 2004/112782 A1 | 12/2004 |
| WO | WO 2004/112783 A1 | 12/2004 |
| WO | WO 2004/112784 A1 | 12/2004 |
| WO | WO 2004/112785 | 12/2004 |
| WO | WO 2004/113310 A1 | 12/2004 |
| WO | WO 2005/007085 A2 | 1/2005 |
| WO | WO 2005/009974 A1 | 2/2005 |
| WO | WO 2005/016877 A2 | 2/2005 |
| WO | WO 2005/016877 A3 | 2/2005 |
| WO | WO 2005/025507 A2 | 3/2005 |
| WO | WO 2005/027882 A1 | 3/2005 |
| WO | WO 2005/035534 A1 | 4/2005 |
| WO | WO 2005/040136 A1 | 5/2005 |
| WO | WO 2005/042513 A1 | 5/2005 |
| WO | WO 2005/044192 A2 | 5/2005 |
| WO | WO 2005/046685 A1 | 5/2005 |
| WO | WO 2005/047250 A1 | 5/2005 |
| WO | WO 2005/058281 A1 | 6/2005 |
| WO | WO 2005/060963 A1 | 7/2005 |
| WO | WO 2005/063247 A1 | 7/2005 |
| WO | WO 2005/073200 A1 | 8/2005 |
| WO | WO 2005/075471 A2 | 8/2005 |
| WO | WO 2005/077925 A1 | 8/2005 |
| WO | WO 2005/086656 A2 | 9/2005 |
| WO | WO 2005/095350 A1 | 10/2005 |
| WO | WO 2005/097759 A1 | 10/2005 |
| WO | WO 2005/097764 A1 | 10/2005 |
| WO | WO 2005/108359 A1 | 11/2005 |
| WO | WO 2005/108360 A1 | 11/2005 |
| WO | WO 2005/108361 A1 | 11/2005 |
| WO | WO 2005/110413 A2 | 11/2005 |
| WO | WO 2005/110980 A2 | 11/2005 |
| WO | WO 2005/110992 A1 | 11/2005 |
| WO | WO 2005/116002 A2 | 12/2005 |
| WO | WO 2005/118538 A2 | 12/2005 |

OTHER PUBLICATIONS

Cui, Yingjie et al.: "Synthesis and antibacterial activity of oxazolidinone containing sulfonyl group" Bioorganic & Medicinal Chemistry Letters, 13(14), 2311-2313 Coden: BMCLE8; ISSN: 0960-894X, 2003, XP002396838 p. 2311; compounds YC-20 p. 2312; table 1; compounds 6-17 abstract, (2003).

Fotsch C. et al.: "11[beta]-Hydroxysteroid dehydrogenase-1 as a therapeutic target for metabolic diseases" Expert Opinion on Therapeutic Patents, Ashley Publications, GB, vol. 15, No. 3, 2005, pp. 289-303, XP002376609, ISSN: 1354-3776.

* cited by examiner

FIGURE 1

DNA sequence encoding PCR Primer hsd1_24-f [SEQ. ID No. 1]

1 AACGAGGAAT TCAGACCAGA GATG

DNA sequence encoding PCR Primer hsd1-292-r [SEQ. ID No. 2]

1 TTACTTGTTT ATGAATCTGT CCAT

HYDROXYSTEROID DEHYDROGENASE INHIBITORS

RELATED APPLICATION

This application claims the benefit of U.S. Provisional Application No. 60/667,297, filed Mar. 31, 2005, which is incorporated herein by reference.

FIELD OF THE INVENTION

The present invention relates to compounds that may be used to inhibit hydroxysteroid dehydrogenases, as well as compositions of matter and kits comprising these compounds. The invention also relates to methods for inhibiting hydroxysteroid dehydrogenases and treatment methods using compounds according to the present invention. In particular, the present invention relates to 11β-Hydroxysteroid Dehydrogenase Type 1 inhibitors, compositions of matter and kits comprising these compounds and methods for inhibiting 11β-Hydroxysteroid Dehydrogenase Type 1.

BACKGROUND OF THE INVENTION

The present invention relates to inhibitors of enzymes that catalyse the interconversion of active and inactive glucocorticoids, compositions comprising the inhibitors, kits and articles of manufacture comprising the inhibitors and compositions, methods of making the inhibitors and compositions, and methods of using the inhibitors and compositions. The inhibitors and compositions comprising them are useful for treating or modulating diseases in which enzymes that catalyse the interconversion of glucocorticoids may be involved, symptoms of such diseases, or the effect of other physiological events mediated by these enzymes. Accordingly, the invention also provides for methods of treating diseases in which one or more enzymes that catalyse the interconversion of glucocorticoids is involved.

Short-chain dehydrogenases/reductases are a family of reversible NAD(H)/NADP(H) dependent oxidoreductases that interconvert active and inactive glucocorticoids. For example, 11β-Hydroxysteroid Dehydrogenase Type 1 (11b-HSD1) belongs to the short-chain dehydrogenase/reductase family of enzymes. Specifically, 11b-HSD1 catalyses the conversion of inactive and active glucocorticoids in a number of tissues and organs including adipose tissue, liver, bone, pancreas, endothelium, ocular tissue, muscle and parts of the central nervous system (Tomlinson et al., *Endocr. Rev.*, 25 (5), 831-66 (2004)).

11b-HSD1 has been implicated in type-2 diabetes, osteoporosis, hypertension, ocular disorders, cognitive disorders, the metabolic syndrome and other metabolic disorders. The non-specific 11b-HSD1 inhibitor carbenoxolone increases insulin sensitivity in healthy, lean, humans as well as those with the symptoms of type-2 diabetes (Andrews et al., *J. Clin. Endocrinol. Metab.*, 88 (1), 285-91 (2003)). Mice that overexpress 11b-HSD1 in adipocytes develop hyderlipidemia, insulin resistance and visceral obesity. This phenotype has been shown to resemble the human metabolic syndrome (Masuzaki et al., *Science*, 294 (5549), 2166-70 (2001)). 11b-HSD1 knockout mice have shown resistance to developing obesity-induced, and stress-induced, insulin resistance as well as displaying decreased HDL-cholesterol and VLDL triglycerides (Kotelevtsev et al., *Proc. Natl. Acad. Sci. USA,* 94 (26), 14924-29 (1997)). These findings have stimulated interest in inhibitors of 11b-HSD1 as potential drugs for the treatment of disorders where a decreased level of active intracellular glucocorticoid is desired.

There is a continued need to find new therapeutic agents to treat human diseases. The hydroxysteroid dehydrogenases, specifically but not limited to 11β-Hydroxysteroid Dehydrogenase Type 1, are especially attractive targets for the discovery of new therapeutics due to their important role in type-2 diabetes, osteoporosis, hypertension, ocular disorders, cognitive disorders, the metabolic syndrome and other metabolic disorders.

SUMMARY OF THE INVENTION

The present invention relates to compounds that have activity for inhibiting hydroxysteroid dehydrogenases. The present invention also provides compositions, articles of manufacture and kits comprising these compounds.

In one embodiment, a pharmaceutical composition is provided that comprises a hydroxysteroid dehydrogenase inhibitor according to the present invention as an active ingredient. Pharmaceutical compositions according to the invention may optionally comprise 0.001%-100% of one or more hydroxysteroid dehydrogenase inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with hydroxysteroid dehydrogenases.

In one embodiment, a kit is provided that comprises a composition comprising at least one hydroxysteroid dehydrogenase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one hydroxysteroid dehydrogenase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit hydroxysteroid dehydrogenases. In particular, the compounds, compositions, kits and articles of manufacture can be used to inhibit 11-β Hydroxysteroid Dehydrogenase Type 1.

In another embodiment, the compounds, compositions, kits and articles of manufacture are used to treat a disease state for which hydroxysteroid dehydrogenases possess activity that contributes to the pathology and/or symptomology of the disease state.

In another embodiment, a compound is administered to a subject wherein hydroxysteroid dehydrogenase activity within the subject is altered, preferably reduced.

In another embodiment, a prodrug of a compound is administered to a subject that is converted to the compound in vivo where it inhibits hydroxysteroid dehydrogenase.

In another embodiment, a method of inhibiting hydroxysteroid dehydrogenases is provided that comprises contacting a hydroxysteroid dehydrogenase with a compound according to the present invention.

In another embodiment, a method of inhibiting hydroxysteroid dehydrogenases is provided that comprises causing a compound according to the present invention to be present in a subject in order to inhibit hydroxysteroid dehydrogenase in vivo.

In another embodiment, a method of inhibiting a hydroxysteroid dehydrogenase is provided that comprises administering a first compound to a subject that is converted in vivo to a second compound wherein the second compound inhibits hydroxysteroid dehydrogenase in vivo. It is noted that the compounds of the present invention may be the first or second compounds.

In another embodiment, a therapeutic method is provided that comprises administering a compound according to the present invention.

In another embodiment, a method of treating a condition in a patient which is known to be mediated by hydroxysteroid dehydrogenases, or which is known to be treated by hydroxysteroid dehydrogenase inhibitors, comprising administering to the patient a therapeutically effective amount of a compound according to the present invention.

In another embodiment, a method is provided for treating a disease state for which hydroxysteroid dehydrogenases possess activity that contributes to the pathology and/or symptomology of the disease state, the method comprising: causing a compound according to the present invention to be present in a subject in a therapeutically effective amount for the disease state.

In another embodiment, a method is provided for treating a disease state for which hydroxysteroid dehydrogenases possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which hydroxysteroid dehydrogenases possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by hydroxysteroid dehydrogenases, or that is known to be treated by hydroxysteroid dehydrogenase inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting hydroxysteroid dehydrogenases and thus may themselves be prodrugs for another compound. Such prodrugs of another compound may or may not themselves independently have hydroxysteroid dehydrogenase inhibitory activity.

BRIEF DESCRIPTION OF THE FIGURES

FIG. 1 illustrates SEQ. ID Nos. 1 and 2 referred to in this application.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "anminoalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})aryl(C_{1-3})alkyl$ includes, benzyl, phenethyl, 1-phenylethyl, 3-phenylpropyl, 2-thienylmethyl, 2-pyridinylmethyl and the like).

"Alkenyl" means a straight or branched, carbon chain that contains at least one carbon-carbon double bond. Examples of alkenyl include vinyl, allyl, isopropenyl, pentenyl, hexenyl, heptenyl, 1-propenyl, 2-butenyl, 2-methyl-2-butenyl, and the like.

"Alkynyl" means a straight or branched, carbon chain that contains at least one carbon-carbon triple bond. Examples of alkynyl include ethynyl, propargyl, 3-methyl-1-pentynyl, 2-heptynyl and the like.

"Alkylene", unless indicated otherwise, means a straight or branched, saturated or unsaturated, aliphatic, divalent radical. $C_X$ alkylene and $C_{X-Y}$ alkylene are typically used where X and Y indicate the number of carbon atoms in the chain. For example, $C_{1-6}$ alkylene includes methylene (—$CH_2$—), ethylene (—$CH_2CH_2$—), trimethylene (—$CH_2CH_2CH_2$—), tetramethylene (—$CH_2CH_2CH_2CH_2$—) 2-butenylene (—$CH_2CH=CHCH_2$—), 2-methyltetramethylene (—$CH_2CH(CH_3)CH_2CH_2$—), pentamethylene (—$CH_2CH_2CH_2CH_2CH_2$—) and the like).

"Alkylidene" means a straight or branched saturated or unsaturated, aliphatic radical connected to the parent molecule by a double bond. $C_X$ alkylidene and $C_{X-Y}$ alkylidene are typically used where X and Y indicate the number of carbon atoms in the chain. For example, $C_{1-6}$ alkylidene includes methylene (=$CH_2$), ethylidene (=$CHCH_3$), isopropylidene (=$C(CH_3)_2$), propylidene (=$CHCH_2CH_3$), allylidene (=$CH—CH=CH_2$), and the like).

"Amino" means a nitrogen moiety having two further substituents where, for example, a hydrogen or carbon atom is attached to the nitrogen. For example, representative amino groups include —$NH_2$, —$NHCH_3$, —$N(CH_3)_2$, —$NHC_{1-10}$-alkyl, —$N(C_{1-10}$-alkyl$)_2$, —NHaryl, —NHheteroaryl, —$N(aryl)_2$, —$N(heteroaryl)_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aminoalkyl" means an alkyl, as defined above, except where one or more substituted or unsubstituted nitrogen atoms (—N—) are positioned between carbon atoms of the alkyl. For example, an $(C_{2-6})$ aminoalkyl refers to a chain comprising between 2 and 6 carbons and one or more nitrogen atoms positioned between the carbon atoms.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $Sp^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. $C_X$ aryl and $C_{X-Y}$ aryl are typically used where X and Y indicate the number of atoms in the ring.

"Bicycloalkyl" means a saturated or partially unsaturated fused bicyclic or bridged polycyclic ring assembly.

"Bicycloaryl" means a bicyclic ring assembly wherein the rings are linked by a single bond or fused and at least one of the rings comprising the assembly is aromatic. $C_X$ bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)$NR_aR_b$ where $R_a$ and $R_b$ are each independently two further substituents where a hydrogen or carbon atom is attached to the nitrogen.

"Carbocycle" means a ring consisting of carbon atoms.

"Carbocyclic ketone derivative" means a carbocyclic derivative wherein the ring contains a —CO— moiety.

"Carbonyl" means the radical —CO—. It is noted that the carbonyl radical may be further substituted with a variety of substituents to form different carbonyl groups including acids, acid halides, aldehydes, amides, esters, and ketones.

"Carboxy" means the radical —$CO_2$—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, fused bicyclic or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

"Cycloalkylene" means a divalent saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted $(C_{1-3})$alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N═, —NR$_c$—, —N$^+$(O$^-$)═, —O—, —S— or —S(O)$_2$—, wherein R$_c$ is further substituent.

"Heterobicycloalkyl" means bicycloalkyl, as defined in this Application, provided that one or more of the atoms within the ring is a heteroatom. For example hetero$(C_{9-12})$ bicycloalkyl as used in this application includes, but is not limited to, 3-aza-bicyclo[4.1.0]hept-3-yl, 2-aza-bicyclo [3.1.0]hex-2-yl, 3-aza-bicyclo[3.1.0]hex-3-yl, and the like.

"Heterocycloalkylene" means cycloalkylene, as defined in this Application, provided that one or more of the ring member carbon atoms is replaced by a heteroatom.

"Heteroaryl" means a cyclic aromatic group having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo [2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring is a heteroatom. For example, hetero$(C_{4-12})$bicycloaryl as used in this Application includes, but is not limited to, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Hydroxy" means the radical —OH.

"Iminoketone derivative" means a derivative comprising the moiety —C(NR)—, wherein R comprises a hydrogen or carbon atom attached to the nitrogen.

"Isomers" mean any compound having an identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Nitro" means the radical —NO$_2$.

"Oxaalkyl" means an alkyl, as defined above, except where one or more oxygen atoms (—O—) are positioned between carbon atoms of the alkyl. For example, an $(C_{2-6})$oxaalkyl refers to a chain comprising between 2 and 6 carbons and one or more oxygen atoms positioned between the carbon atoms.

"Oxoalkyl" means an alkyl, further substituted with a carbonyl group. The carbonyl group may be an aldehyde, ketone, ester, amide, acid or acid chloride.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of inhibitors of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have hydroxysteroid dehydrogenase inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" means a carbocyclic or a heterocyclic system.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, ($C_{1-10}$)alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

"Sulfinyl" means the radical —SO—. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$—. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —CS—. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —$CH_3$) as well as —$CR_aR_bR_c$ where $R_a$, $R_b$, and $R_c$ may each independently be hydrogen or any other substituent where the atom attached to the carbon is a heteroatom or cyano. Hence, $CF_3$, $CH_2OH$ and $CH_2CN$, for example, are all $C_1$ alkyls.

DETAILED DESCRIPTION OF THE INVENTION

The present invention relates to compounds, compositions, kits and articles of manufacture that may be used to inhibit hydroxysteroid dehydrogenases and, in particular, 11β-hydroxysteroid dehydrogenase type 1 (referred to herein as 11b-HSD1).

11b-HSD1 belongs to the short-chain dehydrogenase/reductase (SDR) family of enzymes, of which over 60 members are found in humans (Oppermann et al., *Chem Biol Interact,* 143-144, 247-253 (2003); Kallberg et al., *Protein Sci,* 11, 636-641 (2002)). SDRs are reversible NAD(H)/NADP(H) dependent oxidoreductases containing a structurally conserved α/β nucleotide-binding Rossman fold. Within the core structure, two conserved motifs are shared among all SDR enzymes. A dinucleotide-binding P-loop forms a turn between a β-strand and an α-helix and directly contacts the ribose sugar and pyrophosphate. A Tyr-X—X—X-Lys motif, often in concert with a conserved Ser that orients substrate, catalyzes proton transfer to and from reduced and oxidized reaction intermediates. A flexible region in SDR enzymes, that often changes conformation upon substrate binding to shield the active site from bulk solvent, mediates enzyme specificity. SDR oligomerization and intracellular localization is often mediated by extensions at the N-and C-termini.

11b-HSD1 is a NADPH-dependent enzyme that functions predominantly as a reductase in vivo. In cells, a single N-terminal transmembrane helix and associated linker anchors the C-terminal catalytic domain within the lumen of the endoplasmic reticulum (ER).

11b-HSD1 is important in regulating local concentrations of glucocorticoids in various tissue types, for example, adipose, vascular, brain, testis, ocular and placental. Disregulation of 11b-HSD1 is implicated in such areas as type-2 diabetes, osteoporosis, hypertension, ocular disorders, cognitive disorders, the metabolic syndrome and other metabolic disorders.

It is noted that the compounds of the present invention may also possess inhibitory activity for other short chain dehydrogenase family members and thus may be used to address disease states associated with these other family members.

Crystal Structure of 11β-Hydroxysteroid Dehydrogenase

Syrrx, Inc. (San Diego, Calif.) solved the crystal structure of 11β-hydroxysteroid dehydrogenase type 1 (11b-HSD1) (U.S. patent application Ser. No. 10/800,024, filed Mar. 12, 2004, and Ser. No. 10/800,427, filed Mar. 12, 2004, each of which is hereby incorporated herein by reference in its entirety). Knowledge of the crystal structure was used to guide the design of the inhibitors provided herein.

The overall Rossman fold topology of 11b-HSD1 resembles other SDR enzymes in which a central 6-stranded, all-parallel β-sheet is sandwiched on both sides by 3α-helices (Hosfield et al., *J. Biol. Chem.*, 280 (6), 4639-48 (2005)). A conformationally-variable β6-α6 insertion that forms one wall of the steroid binding pocket, an additional β-strand (β7) and two C terminal α-helices (αE and αF) are appended to the core structure and complete the 11b-HSD1 fold. NADP+ binding to 11b-HSD1 is similar to other SDR enzymes, with the molecule binding in an extended conformation in which both ribose sugars adopt a C2-endo conformation. The adenine and nicotinamide rings are both well ordered and bind roughly perpendicular to the plane of the ribose sugars with the adenine adopting an anti configuration and the nicotinamide adopting a syn configuration. The adenosine moiety lies in a cleft formed by 4 loops (β1/α1, β2/α2, β3/α3, and β4/α4) and an α-helix (α4).

Hydroxysteroid Dehydrogenase Inhibitors

In one embodiment, hydroxysteroid dehydrogenase inhibitors of the present invention comprise:

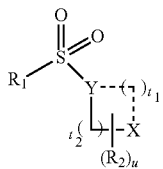

wherein:

$t_1$ is selected from the group consisting of 1, 2 and 3;

$t_2$ is selected from the group consisting of 1, 2 and 3;

u is selected from the group consisting of 0, 1, 2, 3, 4, 5, 6, 7, 8, 9 and 10;

X is selected from the group consisting of $NR_3$ and $CR_4R_5$;

Y is selected from the group consisting of N and $CR_{10}$;

$R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted, with the proviso that $R_1$ is not alk-4-yl-phenyl when Y is N;

$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;

$R_3$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;

$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring; and $R_{10}$ is selected from the group consisting of nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted.

In one variation of the above embodiment, t, is selected from the group consisting of 2 and 3. In another variation, $t_1$ is 2. In yet another variation, $t_2$ is selected from the group consisting of 2 and 3. In still another variation, $t_2$ is 2.

In another embodiment, hydroxysteroid dehydrogenase inhibitors of the present invention comprise:

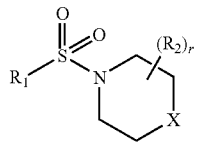

wherein:
r is selected from the group consisting of 0, 1, 2, 3, 4, 5, 6, 7 and 8;
X is selected from the group consisting of $NR_3$ and $CR_4R_5$;
$R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted, with the proviso that $R_1$ is not alk-4-yl-phenyl;
$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;
$R_3$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;
$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring; and
$R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring.

In yet another embodiment, hydroxysteroid dehydrogenase inhibitors of the present invention comprise:

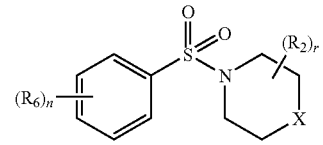

wherein:
r is selected from the group consisting of 0, 1, 2, 3, 4, 5, 6, 7 and 8;
n is selected from the group consisting of 1, 2, 3, 4 and 5;
X is selected from the group consisting of $NR_3$ and $CR_4R_5$;
$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;
$R_3$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;
$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring; and
$R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring; and each $R_6$ is independently selected from the group consisting of hydrogen, nitro, cyano, thio, hydroxy, carboxy, alkoxy, aryloxy, heteroaryloxy, carbonyl, amino, carboxamido, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_6$ are taken together to form a ring, with the proviso that $R_6$ is not an alk-4-yl.

In still another embodiment, hydroxysteroid dehydrogenase inhibitors of the present invention comprise:

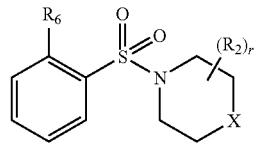

wherein:

r is selected from the group consisting of 0, 1, 2, 3, 4, 5, 6, 7 and 8;

X is selected from the group consisting of $NR_3$ and $CR_4R_5$;

$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;

$R_3$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;

$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring; and $R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring; and $R_6$ is selected from the group consisting of hydrogen, nitro, cyano, thio, hydroxy, carboxy, alkoxy, aryloxy, heteroaryloxy, carbonyl, amino, carboxamido, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted.

In a further embodiment, hydroxysteroid dehydrogenase inhibitors of the present invention comprise:

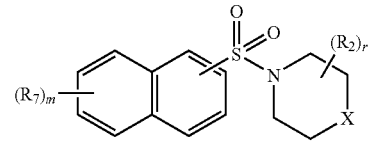

wherein:

r is selected from the group consisting of 0, 1, 2, 3, 4, 5, 6, 7 and 8;

m is selected from the group-consisting of 0, 1, 2, 3, 4, 5, 6 and 7;

X is selected from the group consisting of $NR_3$ and $CR_4R_5$;

$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;

$R_3$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;

$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring; and each $R_7$ is independently selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_7$ are taken together to form a ring.

In another embodiment, hydroxysteroid dehydrogenase inhibitors of the present invention comprise:

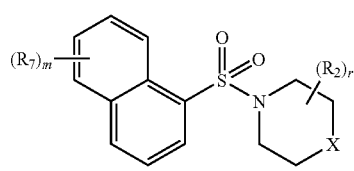

wherein:

r is selected from the group consisting of 0, 1, 2, 3, 4, 5, 6, 7 and 8;

m is selected from the group consisting of 0, 1, 2, 3, 4, 5, 6 and 7;

X is selected from the group consisting of $NR_3$ and $CR_4R_5$;

$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;

$R_3$ is selected from the group consisting of hydrogen, nitro, thio, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;

$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring; and each $R_7$ is independently selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl ($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_7$ are taken together to form a ring.

In yet another embodiment, hydroxysteroid dehydrogenase inhibitors of the present invention comprise:

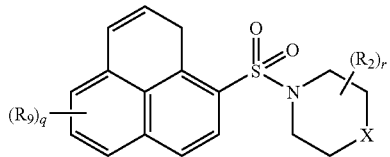

wherein:

r is selected from the group consisting of 0, 1, 2, 3, 4, 5, 6, 7 and 8;

q is selected from the group consisting of 0, 1, 2, 3, 4, 5, 6, 7, 8 and 9;

X is selected from the group consisting of $NR_3$ and $CR_4R_5$;

$R_2$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;

$R_3$ is selected from the group consisting of hydrogen, nitro, thio, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_3$ are taken together to form a ring;

$R_4$ is selected from the group consisting of halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_4$ and $R_5$ are taken together to form a ring; and each $R_9$ is independently selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$) alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl ($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_9$ are taken together to form a ring.

In a further embodiment, hydroxysteroid dehydrogenase inhibitors of the present invention comprise:

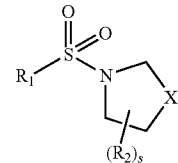

wherein:

s is selected from the group consisting of 0, 1, 2, 3, 4, 5 and 6;

X is $CR_4R_5$;

$R_1$ is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted, with the proviso that $R_1$ is not an alk-4-yl-phenyl;

$R_2$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;

$R_4$ is selected from the group consisting of halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl ($C_{1-5}$)alkyl, perhalo($C_{1-10}$)alkyl, ($C_{3-12}$)cycloalkyl ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_4$ are taken together to form a ring; and $R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring.

In still a further embodiment, hydroxysteroid dehydrogenase inhibitors of the present invention comprise:

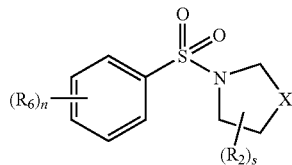

wherein:

s is selected from the group consisting of 0, 1, 2, 3, 4, 5 and 6;

n is selected from the group consisting of 1, 2, 3, 4 and 5;

X is $CR_4R_5$;

$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;

$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring; and $R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_4$ and $R_5$ are taken together to form a ring; and each $R_6$ is independently selected from the group consisting of hydrogen, nitro, cyano, thio, hydroxy, carboxy, alkoxy, aryloxy, heteroaryloxy, carbonyl, amino, carboxamido, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_6$ are taken together to form a ring, with the proviso that $R_6$ is not an alk-4-yl.

In yet a further embodiment, hydroxysteroid dehydrogenase inhibitors of the present invention comprise:

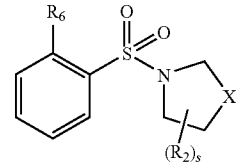

wherein:

s is selected from the group consisting of 0, 1, 2, 3, 4, 5 and 6;

X is $CR_4R_5$;

$R_2$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;

$R_4$ is selected from the group consisting of halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_4$ are taken together to form a ring; and $R_5$ is selected from the group consisting of hydrogen, halo, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_4$ and $R_5$ are taken together to form a ring; and $R_6$ is selected from the group consisting of hydrogen, nitro, cyano, thio, hydroxy, carboxy, alkoxy, aryloxy, heteroaryloxy, carbonyl, amino, carboxamido, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted.

In another embodiment, hydroxysteroid dehydrogenase inhibitors of the present invention comprise:

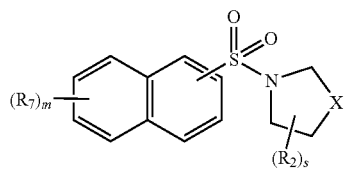

wherein:

S is selected from the group consisting of 0, 1, 2, 3, 4, 5 and 6;

m is selected from the group consisting of 0, 1, 2, 3, 4, 5, 6 and 7;

X is $CR_4R_5$;

$R_2$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;

$R_4$ is selected from the group consisting of halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_4$ and $R_5$ are taken together to form a ring; and each $R_7$ is independently selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_7$ are taken together to form a ring.

In still another embodiment, hydroxysteroid dehydrogenase inhibitors of the present invention comprise:

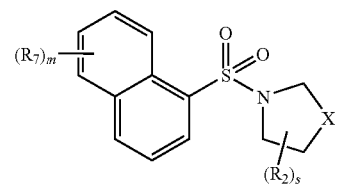

wherein:

s is selected from the group consisting of 0, 1, 2, 3, 4, 5 and 6;

m is selected from the group consisting of 0, 1, 2, 3, 4, 5, 6 and 7;

X is $CR_4R_5$;

$R_2$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;

$R_4$ is selected from the group consisting of halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_4$ and $R_5$ are taken together to form a ring; and each $R_7$ is independently selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_7$ are taken together to form a ring.

In yet another embodiment, hydroxysteroid dehydrogenase inhibitors of the present invention comprise:

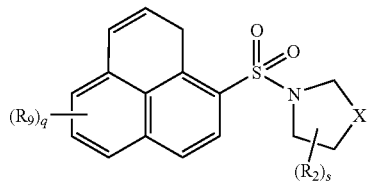

wherein:
s is selected from the group consisting of 0, 1, 2, 3, 4, 5 and 6;
q is selected from the group consisting of 0, 1, 2, 3, 4, 5, 6, 7, 8 and 9;
X is $CR_4R_5$;
$R_2$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;

$R_4$ is selected from the group consisting of halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_4$ are taken together to form a ring;

$R_5$ is selected from the group consisting of hydrogen, halo, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_4$ and $R_5$ are taken together to form a ring; and each $R_9$ is independently selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_9$ are taken together to form a ring.

In one variation of each of the above embodiments and variations, $R_1$ is selected from the group consisting of:

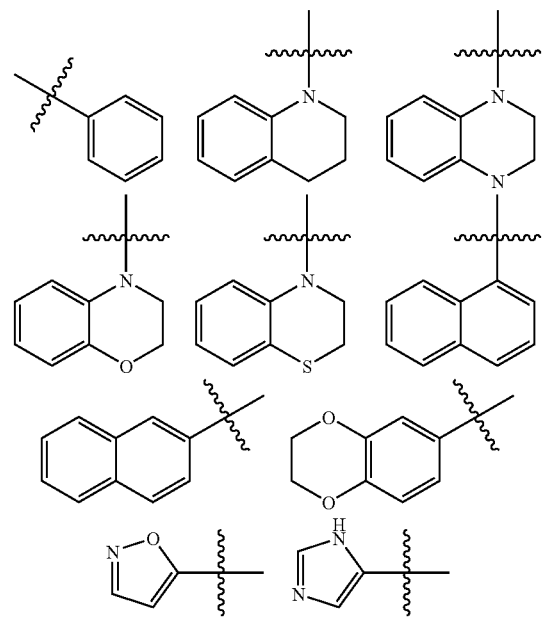

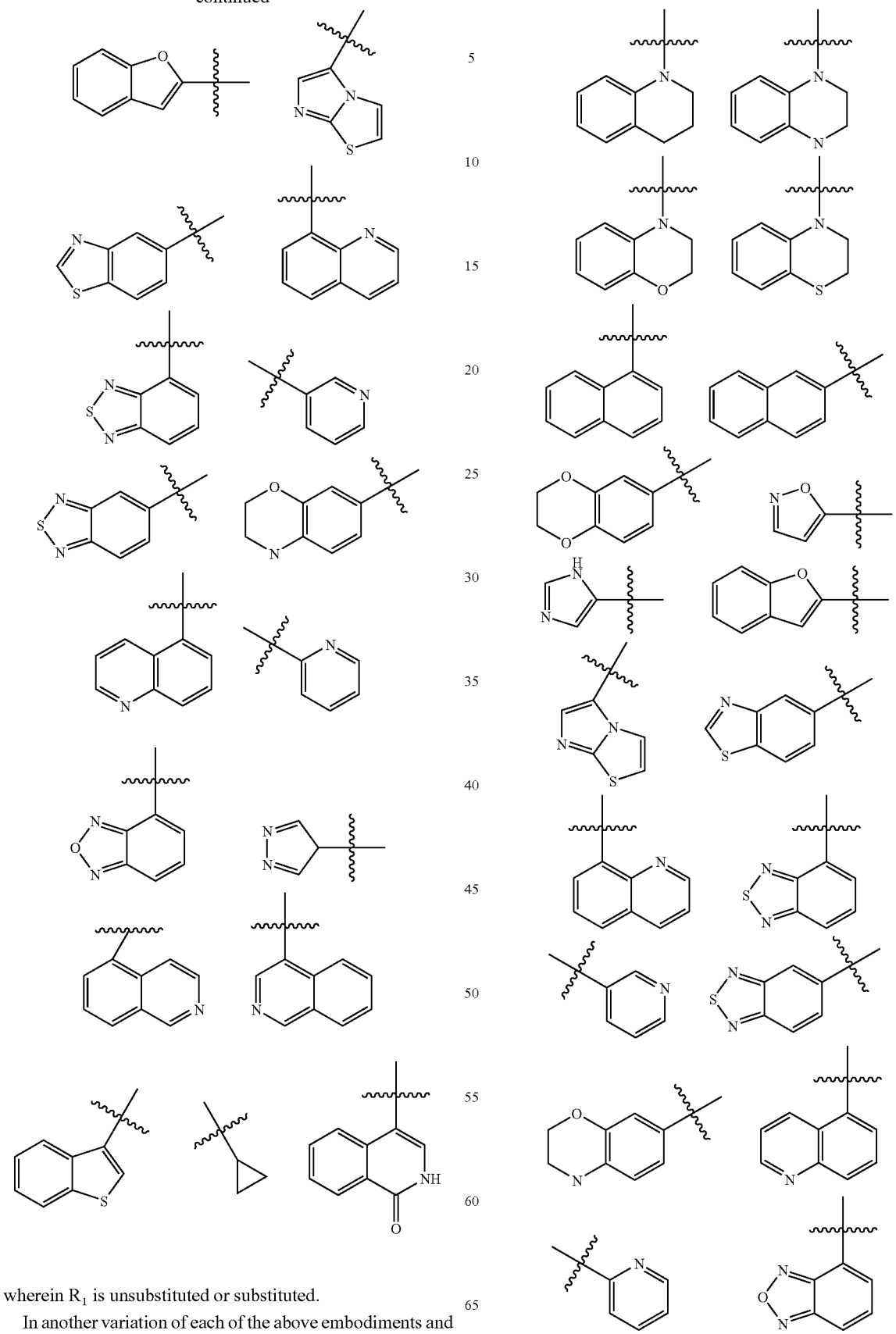
wherein $R_1$ is unsubstituted or substituted.
In another variation of each of the above embodiments and variations, $R_1$ is selected from the group consisting of:

-continued

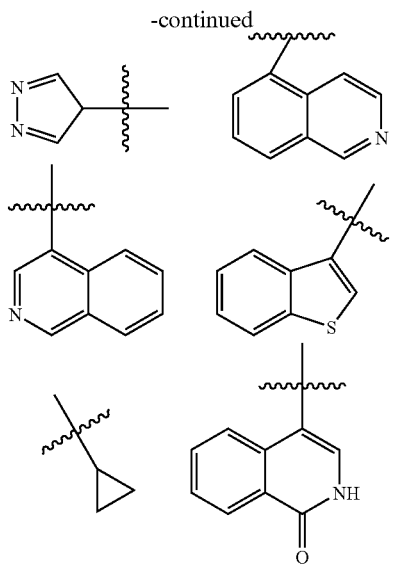

wherein $R_1$ is unsubstituted or substituted.

In another variation of each of the above embodiments and variations, $R_2$ is selected from the group consisting of halo, alkoxy, $(C_{1-3})$alkyl, halo$(C_{1-3})$alkyl, $(C_{3-6})$cycloalkyl, dialkylamino and cycloamino, each substituted or unsubstituted. In another variation, $R_2$ is selected from the group consisting of —$CH_3$, cyclopropyl, —F, —$CF_3$ and —$OCH_3$, each substituted or unsubstituted.

In another variation of each of the above embodiments and variations, $R_3$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted. In another variation, $R_3$ comprises:

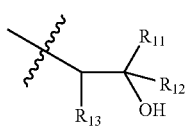

wherein:
$R_{11}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted;
$R_{12}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_{11}$ and $R_{12}$ are taken together to form a ring; and
$R_{13}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted.

In still another variation of each of the above embodiments and variations, $R_3$ comprises:

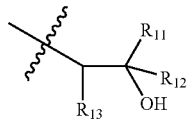

wherein:
$R_{11}$ is selected from the group consisting of hydrogen, —$CH_3$; —$CH_2CH_3$; —$CH(CH_3)_2$; —$CH_2CH(CH_3)_2$; —$CH_2C(CH_3)H_2$; -Ph; —$CH_2Ph$; spiro-cyclobutyl; or spiro-cyclopentyl, each substituted or unsubstituted;
$R_{12}$ is selected from the group consisting of hydrogen and methyl, substituted or unsubstituted; and
$R_{13}$ is selected from the group consisting of hydrogen, propyl, cyclopropyl, spiro-cyclopropyl, butyl, spiro-cyclobutyl, spiro-cyclopentyl, benzyl, and phenyl, each substituted or unsubstituted.

In yet another variation of each of the above embodiments and variations, $R_3$ is selected from the group consisting of methyl, cyclopropyl, cyclobutyl, cyclopentyl, phenyl, pyridyl, pyrimidyl, thiazolyl, and adamantly, each substituted or unsubstituted. In another variation, $R_3$ comprises:

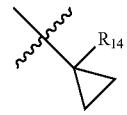

wherein $R_{14}$ is selected from the group consisting of hydrogen, nitro, cyano, thio, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$ cycloalkyl, hetero$(C_{3-12})$cycloalkyl, $(C_{9-12})$ bicycloalkyl, hetero$(C_{3-12})$bicycloalkyl, aryl$(C_{1-10})$ alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted.

In one variation of the above variation, $R_{14}$ is selected from the group consisting of $(C_{1-6})$alkyl, halo$(C_{1-6})$alkyl, and aminocarbonyl, each substituted or unsubstituted.

In a further variation of each of the above embodiments and variations, $R_3$ is a substituted or unsubstituted phenyl. In another variation, $R_3$ is a phenyl substituted with a substituent selected from the group consisting of hydroxy, halo, alkoxy, carbonyl, nitro, and amino, each substituted or unsubstituted.

In one variation of each of the above embodiments and variations, $R_4$ is selected from the group consisting of ($C_{3-12}$) cycloalkyl, hetero($C_{3-12}$)cycloalkyl, ($C_{9-12}$)bicycloalkyl, hetero($C_{3-12}$)bicycloalkyl, aryl, heteroaryl, ($C_{9-12}$)bicycloaryl, and hetero($C_{4-12}$)bicycloaryl, each substituted or unsubstituted. In another variation, $R_4$ is selected from the group consisting of:

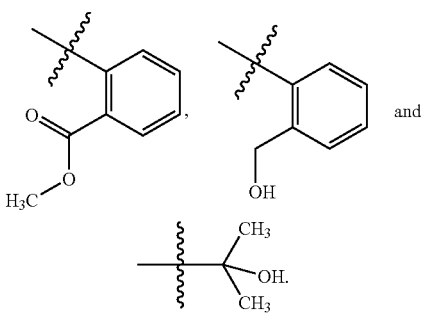

In still another variation of each of the above embodiments and variations, $R_4$ comprises:

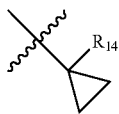

wherein $R_{14}$ is selected from the group consisting of hydrogen, nitro, cyano, thio, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$) cycloalkyl, hetero($C_{3-12}$)cycloalkyl, ($C_{9-12}$) bicycloalkyl, hetero($C_{3-12}$)bicycloalkyl, aryl($C_{1-10}$) alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted.

In one variation of the above variation, $R_{14}$ is selected from the group consisting of ($C_{1-6}$)alkyl, halo($C_{1-6}$)alkyl, and aminocarbonyl, each substituted or unsubstituted.

In another variation of each of the above embodiments and variations, $R_4$ is a substituted or unsubstituted phenyl. In another variation, $R_4$ is a phenyl substituted with a substituent selected from the group consisting of hydroxy, halo, alkoxy, carbonyl, nitro, and amino, each substituted or unsubstituted.

In still another variation of each of the above embodiments and variations, $R_6$ is selected from the group consisting of halo, cyano, alkoxy, aryloxy, ($C_{1-6}$)alkyl, and aryl, each substituted or unsubstituted.

In a further variation of each of the above embodiments and variations, $R_7$ is selected from the group consisting of ($C_{1-6}$) alkyl and amino, each substituted or unsubstituted.

In still another embodiment, the present invention relates to a compound selected from the group consisting of:

1-Phenyl-4-(m-tolylsulfonyl)piperazine;
1-(3-Methoxyphenylsulfonyl)-4-phenylpiperazine;
1-(3-Phenoxyphenylsulfonyl)-4-phenylpiperazine;
1-(3-Chloro-2-methylphenylsulfonyl)-4-phenylpiperazine;
1-(naphthalen-1-ylsulfonyl)-4-phenylpiperazine;
1-(2,3-dihydrobenzo[b][1,4]dioxin-6-ylsulfonyl)-4-phenylpiperazine;
1-(4-Phenoxyphenylsulfonyl)-4-phenylpiperazine;
1-(4-Methoxyphenylsulfonyl)-4-phenylpiperazine;
1-(2,4-Dimethoxy-benzenesulfonyl)-4-phenyl-piperazine;
N-[4-(4-Phenyl-piperazine-1-sulfonyl)-phenyl]-acetamide;
1-(2-Chloro-6-methyl-benzenesulfonyl)-4-phenyl-piperazine;
1-(2,6-Dichloro-benzenesulfonyl)-4-phenyl-piperazine;
1-(2-Chloro-4-fluoro-benzenesulfonyl)-4-phenyl-piperazine;
1-(2,3-Dichloro-benzenesulfonyl)-4-phenyl-piperazine;
1-(2,4-Dichloro-benzenesulfonyl)-4-phenyl-piperazine;
1-(3,4-Dimethyl-isoxazole-5-sulfonyl)-4-phenyl-piperazine;
1-(1,2-Dimethyl-$^1$H-imidazole-4-sulfonyl)-4-phenyl-piperazine;
1-(Benzofuran-2-sulfonyl)-4-phenyl-piperazine;
6-Methyl-5-(4-phenyl-piperazine-1-sulfonyl)-imidazo[2,1-b]thiazole;
5-(4-Phenyl-piperazine-1-sulfonyl)-benzothiazole;
2-(4-phenylpiperazin-1-ylsulfonyl)benzonitrile;
4-(4-phenylpiperazin-1-ylsulfonyl)benzonitrile;
1-(2-chlorophenylsulfonyl)-4-phenylpiperazine;
1-(3-chlorophenylsulfonyl)-4-phenylpiperazine;
1-Phenyl-4-(o-tolylsulfonyl)piperazine;
1-(2,5-Difluorophenylsulfonyl)-4-phenylpiperazine;
8-(4-Phenylpiperazin-1-ylsulfonyl)quinoline;
1-(3-Chloro-2-fluorophenylsulfonyl)-4-phenylpiperazine;
4-(4-Phenylpiperazin-1-ylsulfonyl)benzo[c][1,2,5]thiadiazole;
1-(5-Bromo-6-chloropyridin-3-ylsulfonyl)-4-phenylpiperazine;
1-(6-Morpholinopyridin-3-ylsulfonyl)-4-phenylpiperazine;
3-(4-Phenylpiperazin-1-ylsulfonyl)benzonitrile;
1-(2-Fluorophenylsulfonyl)-4-phenylpiperazine;
1-(2-Bromophenylsulfonyl)-4-phenylpiperazine;
5-(4-Phenylpiperazin-1-ylsulfonyl)benzo[c][1,2,5]thiadiazole;
4-Methyl-7-(4-phenylpiperazin-1-ylsulfonyl)-3,4-dihydro-2H-benzo[b][1,4]oxazine;
5-(4-Phenylpiperazin-1-ylsulfonyl)Isoquinoline;
1-Phenyl-4-(pyridin-2-ylsulfonyl)piperazine;
4-(4-Phenylpiperazin-1-ylsulfonyl)benzo[c][1,2,5]oxadiazole;
1-(3,5-Dimethyl-1H-pyrazol-4-ylsulfonyl)-4-phenylpiperazine;
2-(4-(2-Chlorophenylsulfonyl)piperazin-1-yl)phenol;
2-(4-(3-Chlorophenylsulfonyl)piperazin-1-yl)phenol;
2-(4-Naphthalen-1-ylsulfonyl)piperazin-1-yl)phenol;
1-(2-Chlorophenyl)-4-(2-chlorophenylsulfonyl)piperazine;
1-(3-Chlorophenyl)-4-(2-chlorophenylsulfonyl)piperazine;
1-(4-Chlorophenyl)-4-(2-chlorophenylsulfonyl)piperazine;
1-(2-Chlorophenylsulfonyl)-4-(2-methoxyphenyl)piperazine;
(1R,4S)-2-(4-Chlorophenyl)-5-(2-chlorophenylsulfonyl)-2,5-diaza-bicyclo[2.2.1]heptane;
4-(4-(2-Chlorophenylsulfonyl)piperazin-1-yl)benzaldehyde;
4-(4-(2-Chlorophenylsulfonyl)piperazin-1-yl)phenol;
1-(4-(4-(2-Chlorophenylsulfonyl)piperazin-1-yl)phenyl) ethanone;

1-(2-Chlorophenylsulfonyl)-4-(2-nitrophenyl)piperazine;
1-(2-Chlorophenylsulfonyl)-4-(3-nitrophenyl)piperazine;
1-(2-Chlorophenylsulfonyl)-4-(4-nitrophenyl)piperazine;
2-(4-(2-Chlorophenylsulfonyl)piperazin-1-yl)benzenamine;
2-(4-(2-Chlorophenylsulfonyl)piperazin-2-yl)benzenamine;
2-(4-(2-Chlorophenylsulfonyl)piperazin-1-yl)benzoic acid;
2-(4-(2-Chlorophenylsulfonyl)piperazin-1-yl)benzamide;
1-(2-Chlorophenylsulfonyl)-4-(pyridin-2-yl)piperazine;
1-(Naphthalen-1-ylsulfonyl)-4-(pyridin-2-yl)piperazine;
1-(2-Chlorophenylsulfonyl)-4-(5-chloropyridin-2-yl)piperazine;
1-(2-Chlorophenylsulfonyl)-4-(3-nitropyridin-2-yl)piperazine;
3-[4-(2-Chloro-benzenesulfonyl)-piperazin-1-yl]-pyridin-2-ol;
2-(4-(2-Chlorophenylsulfonyl)piperazin-1-yl)pyrimidine;
2-(4-(Naphthalen-1-ylsulfonyl)piperazin-1-yl)pyrimidine;
2-(4-(Naphthalen-2-ylsulfonyl)piperazin-1-yl)pyrimidine;
1-(2-Chlorophenylsulfonyl)-4-(5-nitrothiazol-2-yl)piperazine;
2-(4-(2-chlorophenylsulfonyl)piperazin-1-yl)thiazole-4-carboxylic acid;
2-(4-(2-Chlorophenylsulfonyl)piperazin-1-yl)thiazole-4-carboxamide;
(2-(4-(2-Chlorophenylsulfonyl)piperazin-1-yl)thiazol-4-yl)methanol;
1-(Naphthalen-1-ylsulfonyl)-4-(thiazol-2-yl)piperazine;
1-(2-Chlorophenylsulfonyl)-4-1'-adamantylpiperazine
tert-Butyl 2-(4-(4-chlorophenylsulfonyl)-2-oxopiperazin-1-yl)acetate;
1-(2-Chlorophenylsulfonyl)-4-cyclopentylpiperazine;
1-(2-chlorophenylsulfonyl)-4-cyclohexylpiperazine;
1-Cyclopentyl-4-(naphthalen-1-ylsulfonyl)piperazine;
8-(4-Cyclopentylpiperazin-1-ylsulfonyl)quinoline;
1-Cyclopentyl-4-(4-methylnaphthalen-1-ylsulfonyl)piperazine;
5-(4-Cyclopentylpiperazin-1-ylsulfonyl)-N,N-dimethylnaphthalen-1-amine;
5-(4-Cyclopentylpiperazin-1-ylsulfonyl)Isoquinoline;
1-(5-Chloronaphthalen-1-ylsulfonyl)-4-cyclopentylpiperazine;
1-(2-Chlorophenylsulfonyl)piperazine;
1-Benzyl-4-(2-chlorophenylsulfonyl)piperazin-2-one;
(R)-N-(1-Benzylpyrrolidin-3-yl)-2-chlorobenzenesulfonamide;
2-(2-Chlorophenylsulfonyl)-octahydropyrrolo[1,2-a]pyrazine;
2-(2-Chlorophenylsulfonyl)-octahydro-1H-pyrido[1,2-a]pyrazine;
4-(4-(2-Chlorophenylsulfonyl)piperazin-1-yl)-1H-indole;
7-(4-(2-Chlorophenylsulfonyl)piperazin-1-yl)-1H-indazole;
4-(4-(2-Chlorophenylsulfonyl)piperazin-1-yl)-1H-indazole;
1-(1-(Naphthalen-1-ylsulfonyl)piperidin-4-yl)-1H-benzo[d]imidazol-2(3H)-one;
1-(1-(2-Chlorophenylsulfonyl)piperidin-4-yl)piperidin-2-one;
1-(2-chlorophenylsulfonyl)-4-(piperidin-1-yl)piperidine;
1-(2-chlorophenylsulfonyl)-4-phenyl-1,2,3,6-tetrahydropyridine;
1-(2-chlorophenylsulfonyl)-4-phenylpiperidine;
1-(2-Chlorophenylsulfonyl)-4-(pyrrolidin-1-yl)piperidine;
4-(1-(2-Chlorophenylsulfonyl)piperidin-4-yl)morpholine;
1-(2-Chlorophenylsulfonyl)-4-(2-methoxyphenyl)piperidine;
1-(2-Chlorophenylsulfonyl)-4-o-tolylpiperidine;
Methyl 2-(1-(naphthalen-1-ylsulfonyl)piperidin-4-yl)benzoate;
(2-(1-(Naphthalen-1-ylsulfonyl)piperidin-4-yl)phenyl)methanol;
(4aR,8aS)-2-(2-Chlorophenylsulfonyl)-decahydroisoquinoline;
3-(1-(2-Chlorophenylsulfonyl)piperidin-4-yl)-6-fluorobenzo[d]isoxazole;
1-(4-(Naphthalen-1-ylsulfonyl)piperazin-1-yl)butan-2-ol;
(R)-3-Methyl-2-(4-(naphthalen-1-ylsulfonyl)piperazin-1-yl)butan-1-ol;
(S)-3-Methyl-2-(4-(naphthalen-1-ylsulfonyl)piperazin-1-yl)butan-1-ol;
Methyl 2-methyl-2-(4-(naphthalen-1-ylsulfonyl)piperazin-1-yl)propanoate;
(R)-4-Methyl-2-(4-(naphthalen-1-ylsulfonyl)piperazin-1-yl)pentan-1-ol;
(R)-2-(4-(Naphthalen-1-ylsulfonyl)piperazin-1-yl)pentan-1-ol;
(1-(4-(Naphthalen-1-ylsulfonyl)piperazin-1-yl)cyclopentyl)methanol;
(R)-2-(4-(Naphthalen-1-ylsulfonyl)piperazin-1-yl)-3-phenylpropan-1-ol;
(R)-2-(4-(Naphthalen-1-ylsulfonyl)piperazin-1-yl)-2-phenylethanol;
(R)-1-(4-(Naphthalen-1-ylsulfonyl)piperazin-1-yl)propan-2-ol;
(S)-1-(4-(Naphthalen-1-ylsulfonyl)piperazin-1-yl)propan-2-ol;
Trans-2-(4-(2-chlorophenylsulfonyl)piperazin-1-yl)cyclopentanol;
Trans-2-(4-(2-chlorophenylsulfonyl)piperazin-1-yl)cyclohexanol;
4-(4-cyclopentylpiperazin-1-ylsulfonyl)isoquinolin-1-ol;
Methyl 1-(naphthalen-1-ylsulfonyl)piperidine-4-carboxylate;
2-(1-(Naphthalen-1-ylsulfonyl)piperidin-4-yl)propan-2-ol;
1-(1-(Naphthalen-1-ylsulfonyl)piperidin-4-yl)cyclopropanol;
1-(4-(Naphthalen-1-ylsulfonyl)piperazin-1-yl)ethanone;
1-(1-Methylcyclopropyl)-4-(naphthalen-1-ylsulfonyl)piperazine;
1-(2-Chlorophenylsulfonyl)-4-(1-methylcyclopropyl)piperazine;
1-(3-Chloro-2-methylphenylsulfonyl)-4-(1-methylcyclopropyl)piperazine;
1-(2-Chloro-6-methylphenylsulfonyl)-4-(1-methylcyclopropyl)piperazine;
1-(2-Chloro-4-fluorophenylsulfonyl)-4-(1-methylcyclopropyl)piperazine;
1-(4-Bromo-2-chlorophenylsulfonyl)-4-(1-methylcyclopropyl)piperazine;
1-(1-Methylcyclopropyl)-4-(2-(trifluoromethyl)phenylsulfonyl)piperazine;
3-Chloro-4-(4-(1-methylcyclopropyl)piperazin-1-ylsulfonyl)benzonitrile;
1-(4-Bromo-2-methylphenylsulfonyl)-4-(1-methylcyclopropyl)piperazine;
1-(4-Bromo-2-(trifluoromethyl)phenylsulfonyl)-4-(1-methylcyclopropyl) piperazine;
1-(Benzo[b]thiophen-3-ylsulfonyl)-4-(1-methylcyclopropyl)piperazine;
5-(4-(1-Methylcyclopropyl)piperazin-1-ylsulfonyl)Isoquinoline;
1-(Cyclopropylsulfonyl)-4-(1-methylcyclopropyl)piperazine;
4-(4-(1-Methylcyclopropyl)piperazin-1-ylsulfonyl)benzonitrile;

1-(4-Isopropoxyphenylsulfonyl)-4-(1-methylcyclopropyl)piperazine;
1-(4-(Difluoromethoxy)phenylsulfonyl)-4-(1-methylcyclopropyl)piperazine;
1-(3-(Difluoromethoxy)phenylsulfonyl)-4-(1-methylcyclopropyl)piperazine;
1-(1-Methylcyclopropyl)-4-(perfluorophenylsulfonyl)piperazine;
(1-(4-(2-chlorophenylsulfonyl)piperazin-1-yl)cyclobutyl)methanol;
Ethyl 1-(4-(2-chlorophenylsulfonyl)piperazin-1-yl)cyclopropanecarboxylate;
4-(2-chlorophenylsulfonyl)-1-cyclopentylpiperidine;
(R)-4-(3-methyl-4-(1-methylcyclopropyl)piperazin-1-ylsulfonyl)isoquinolin-1-ol;
(S)-4-(3-methyl-4-(1-methylcyclopropyl)piperazin-1-ylsulfonyl)isoquinolin-1-ol;
4-(4-(1-methylcyclopropyl)piperazin-1-ylsulfonyl)isoquinolin-1-ol;
(R)-4-(2-chlorophenylsulfonyl)-2-methyl-1-(1-methylcyclopropyl)piperazine;
(R)-4-(2-chlorophenylsulfonyl)-2-methyl-1-(1-methylcyclopropyl)piperazine;
(R)-1-(2-chlorophenylsulfonyl)-2-methyl-4-(1-methylcyclopropyl)piperazine;
1'-(2-chlorophenylsulfonyl)spiro[benzo[d][1,3]dioxole-2,4'-piperidine];
2-(4-(1-methylcyclopropyl)piperazin-1-ylsulfonyl)benzonitrile;
4-benzyl-7-(2-chlorophenylsulfonyl)-4,7-diazaspiro[2.5]octane;
1-(4-fluoronaphthalen-1-ylsulfonyl)-4-(1-methylcyclopropyl)piperazine;
1-(2-chlorophenylsulfonyl)-4-(trifluoromethyl)piperidine;
1-(2-chlorophenylsulfonyl)-4-cyclopropylpiperazine;
(S)-N-cyclopentyl-1-(quinolin-8-ylsulfonyl)pyrrolidin-3-amine;
(S)-8-(3-(azetidin-1-yl)pyrrolidin-1-ylsulfonyl)quinoline;
(R)-4-(3-(dimethylamino)pyrrolidin-1-ylsulfonyl)isoquinolin-1-ol;
(S)-4-(3-(dimethylamino)pyrrolidin-1-ylsulfonyl)isoquinolin-1-ol;
(R)-N,N-dimethyl-1-(quinolin-8-ylsulfonyl)pyrrolidin-3-amine;
(S)-N,N-dimethyl-1-(quinolin-8-ylsulfonyl)pyrrolidin-3-amine;
(R)-1-(1-chloroisoquinolin-4-ylsulfonyl)-N-(cyclopropylmethyl)pyrrolidin-3-amine;
(R)-4-(3-(cyclopropylmethylamino)pyrrolidin-1-ylsulfonyl)isoquinolin-1-ol;
(R)-4-(3-(azetidin-1-yl)pyrrolidin-1-ylsulfonyl)-1-chloroisoquinoline;
(R)-4-(3-(azetidin-1-yl)pyrrolidin-1-ylsulfonyl)isoquinolin-1-ol;
(R)-1-(5-(3-(dimethylamino)pyrrolidin-1-ylsulfonyl)indolin-1-yl)ethanone;
(R)-N,N-dimethyl-1-(2-methyl-4-(thiophen-3-yl)phenylsulfonyl)pyrrolidin-3-amine;
(R)-1-(indolin-5-ylsulfonyl)-N,N-dimethylpyrrolidin-3-amine;
(R)-N,N-dimethyl-1-(3-methylbiphenyl-4-ylsulfonyl)pyrrolidin-3-amine;
(R)-4-(3-(dimethylamino)pyrrolidin-1-ylsulfonyl)-3-methylbenzonitrile;
(R)-1-(4-(dimethylamino)-2-methylphenylsulfonyl)-N,N-dimethylpyrrolidin-3-amine;
1-(4-chloro-5-(4-(1-methylcyclopropyl)piperazin-1-ylsulfonyl)indolin-1-yl)-2,2,2-trifluoroethanone;
4-chloro-5-(4-(1-methylcyclopropyl)piperazin-1-ylsulfonyl)indoline;
1-chloro-4-(4-(1-methylcyclopropyl)piperazin-1-ylsulfonyl)isoquinoline;
4-(2-(4-(4-(1-methylcyclopropyl)piperazin-1-ylsulfonyl)isoquinolin-1-yloxy)ethyl)morpholine;
4-(4-(1-methylcyclopropyl)piperazin-1-ylsulfonyl)-N-(2-morpholinoethyl)isoquinolin-1-amine;
4-(4-cyclopropylpiperazin-1-ylsulfonyl)isoquinolin-1-ol;
1-(2-Chloro-benzenesulfonyl)-4-(1-fluoromethyl-cyclopropyl)-piperazine;
1-(2-Chloro-benzenesulfonyl)-4-(1-trifluoromethyl-cyclopropyl)-piperazine;
1-[4-(2-Chloro-benzenesulfonyl)-piperazin-1-yl]-cyclopropanecarboxylic acid amide;
2-[4-(2-Chloro-benzenesulfonyl)-piperazin-1-yl]-2-cyclopropyl-ethanol;
{1-[1-(2-Chloro-benzenesulfonyl)-piperidin-4-yl]-cyclopropyl}-methanol;
1-(2-Chloro-benzenesulfonyl)-4-(1-trifluoromethyl-cyclopropyl)-piperidine;
1-(2-Chloro-benzenesulfonyl)-4-(1-methyl-cyclopropyl)-piperidine;
1-[1-(2-Chloro-benzenesulfonyl)-piperidin-4-yl]-cyclopropanecarboxylic acid amide;
7-(2-Chloro-benzenesulfonyl)-4-(1-methyl-cyclopropyl)-4,7-diazaspiro[2.5]octane;
1-(2-Chloro-benzenesulfonyl)-2,5-dimethyl-4-(1-methyl-cyclopropyl)-piperazine;
2-(2-Chloro-benzenesulfonyl)-5-(1-methyl-cyclopropyl)-2,5-diaza-bicyclo[2.2.2]octane;
1-(2-Chloro-benzenesulfonyl)-4-fluoro-4-(1-methyl-cyclopropyl)-piperidine;
1-(2-Chloro-benzenesulfonyl)-4-(1-methyl-cyclopropyl)-4-trifluoromethyl-piperidine;
1-(2-Chloro-benzenesulfonyl)-4-fluoro-4-phenyl-piperidine;
1-(2-Chloro-benzenesulfonyl)-4-phenyl-4-trifluoromethyl-piperidine;
1-[4-(1-Methyl-cyclopropyl)-piperazine-1-sulfonyl]-1,2,3,4-tetrahydro-quinoline;
1-(4-Phenyl-piperazine-1-sulfonyl)-1,2,3,4-tetrahydro-quinoline;
1-[4-(1-Methyl-cyclopropyl)-piperazine-1-sulfonyl]-1,2,3,4-tetrahydro-quinoxaline;
1-(4-Phenyl-piperazine-1-sulfonyl)-1,2,3,4-tetrahydro-quinoxaline;
4-[4-(1-Methyl-cyclopropyl)-piperazine-1-sulfonyl]-3,4-dihydro-2H-benzo[1,4]oxazine;
4-(4-Phenyl-piperazine-1-sulfonyl)-3,4-dihydro-2H-benzo[1,4]oxazine;
4-[4-(1-Methyl-cyclopropyl)-piperazine-1-sulfonyl]-3,4-dihydro-2H-benzo[1,4]thiazine;
4-(4-Phenyl-piperazine-1-sulfonyl)-3,4-dihydro-2H-benzo[1,4]thiazine;
1-[4-(1-Methyl-cyclopropyl)-piperazine-1-sulfonyl]-1,2,3,4-tetrahydro-quinoline;
1-(Naphthalen-1-ylsulfonyl)piperazine;
1-(2-Methoxy-phenyl)-4-(naphthalene-2-sulfonyl)-piperazine;
1-(5-Chloro-2-methyl-phenyl)-4-(naphthalene-2-sulfonyl)-piperazine;
Furan-2-yl-[4-(naphthalene-2-sulfonyl)-piperazin-1-yl]-methanone;
1-(4-Chlorophenylsulfonyl)-4-phenylpiperazine;

tert-Butyl 4-(2-chlorophenylsulfonyl)piperazine-1-carboxylate; and 1-(2-Chlorophenylsulfonyl)-4-methylpiperazine.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as a hydrogen.

It is further noted that the compound may be present in a mixture of stereoisomers, or the compound can comprise a single stereoisomer.

The present invention also provides a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

In another of its aspects, there is provided a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting HSD comprising contacting HSD with a compound of any one of the above embodiments and variations.

In yet another of its aspects, there is provided a method of inhibiting HSD comprising causing a compound of any one of the above embodiments and variations to be present in a subject in order to inhibit HSD in vivo.

In a further of its aspects, there is provided a method of inhibiting HSD comprising administering a first compound to a subject that is converted in vivo to a second compound wherein the second compound inhibits HSD in vivo, the second compound being a compound according to any one of the above embodiments and variations.

In another of its aspects, there is provided a method of treating a disease state for which HSD possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which HSD possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which HSD possesses activity that contributes to the pathology and/or symptomology of the disease state, the method comprising administering a first compound to a subject that is converted in vivo to a second compound wherein the second compound inhibits HSD in vivo, the second compound being a compound according to any one of the above embodiments and variations.

In one variation of each of the above methods the disease state is selected from the group consisting of type-2 diabetes, osteoporosis, hypertension, ocular disorders, cognitive disorders, and the metabolic syndrome.

In another variation of each of the above methods, the HSD is an 11b-HSD1.

Salts, Hydrates, and Prodrugs of Hydroxysteroid Dehydrogenase Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g. potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine(benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine(tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as ($C_{1-4}$) alkyl halides, e.g., methyl, ethyl, iso-propyl and tert-butyl chlorides, bromides and iodides; di ($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in T. W. Greene, Protecting *Groups in Organic Synthesis*, $3^{rd}$ edition, John Wiley & Sons, Inc. 1999.

Compounds of the present invention may also be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Preparation Of Hydroxysteroid Dehydrogenase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compositions Comprising Hydroxysteroid Dehydrogenase Inhibitors

A wide variety of compositions and administration methods may be used in conjunction with the hydroxysteroid dehydrogenase inhibitors of the present invention. Such compositions may include, in addition to the hydroxysteroid dehydrogenase inhibitors of the present invention, conventional pharmaceutical excipients, and other conventional, pharmaceutically inactive agents. Additionally, the compositions may include active agents in addition to the hydroxysteroid dehydrogenase inhibitors of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising hydroxysteroid dehydrogenase inhibitors of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The hydroxysteroid dehydrogenase inhibitors and compositions comprising them may be administered or coadministered in any conventional dosage form. Co-administration in the context of this invention is intended to mean the administration of more than one therapeutic agent, one of which includes a hydroxysteroid dehydrogenase inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When hydroxysteroid dehydrogenase inhibitors according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding hydroxysteroid dehydrogenase inhibitors according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more hydroxysteroid dehydrogenase inhibitors according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a hydroxysteroid dehydrogenase inhibitor of the present invention to reduce hydroxysteroid dehydrogenase activity in vivo, thereby treating the disease state of the subject.

Dosage forms or compositions may optionally comprise one or more hydroxysteroid dehydrogenase inhibitors according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more hydroxysteroid dehydrogenase inhibitors, optionally 0.1-95%, and optionally 1-95%.

Salts, preferably sodium salts, of the hydroxysteroid dehydrogenase inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, hydroxysteroid dehydrogenase inhibitors according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The hydroxysteroid dehydrogenase inhibitors of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising hydroxysteroid dehydrogenase inhibitors of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the hydroxysteroid dehydrogenase inhibitors of the present invention by parenteral administration, generally characterized by injection, either subcutaneously, intramuscularly or intravenously. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions include EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of a hydroxysteroid dehydrogenase inhibitor in the parenteral formulation may be adjusted so that an injection administers a pharmaceutically effective amount sufficient to produce the desired pharmacological effect. The exact concentration of a hydroxysteroid dehydrogenase inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the hydroxysteroid dehydrogenase inhibitor to the treated tissue(s). The hydroxysteroid dehydrogenase inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The hydroxysteroid dehydrogenase inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The hydroxysteroid dehydrogenase inhibitors of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a hydroxysteroid dehydrogenase inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the hydroxysteroid dehydrogenase inhibitor.

Topical Administration

The hydroxysteroid dehydrogenase inhibitors of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The hydroxysteroid dehydrogenase inhibitors may be formulated as aerosols for topical application, such as by inhalation (see, U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The hydroxysteroid dehydrogenase inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the hydroxysteroid dehydrogenase inhibitor alone or in combination with other pharmaceutically acceptable excipients can also be administered.

Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax, (polyoxyethylene glycol) and appropriate mixtures of mono-, di-and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Kits Comprising Hydroxysteroid Dehydrogenase Inhibitors

The invention is also directed to kits and other articles of manufacture for treating diseases associated with hydroxysteroid dehydrogenases. It is noted that diseases are intended to cover all conditions for which the hydroxysteroid dehydrogenases possess activity that contributes to the pathology and/or symptomology of the condition.

In one embodiment, a kit is provided that comprises a composition comprising at least one hydroxysteroid dehydrogenase inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one hydroxysteroid dehydrogenase inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Combination Therapy

A wide variety therapeutic agents may have a therapeutic additive or synergistic effect with HSD inhibitors according to the present invention. Accordingly, the present invention also relates to combination therapies wherein one or more compounds according to the present invention are administered to a subject in combination with one or more other therapeutic agents. For example, in one particular embodiment, a method is provided for treating a disease state for which HSD possesses activity comprising administering a compound according to the present invention to a subject in combination with an anti-hypertensive agent. In another particular embodiment, a method is provided for treating a disease state for which HSD possesses activity comprising administering a compound according to the present invention to a subject in combination with a glucocorticoid receptor (GR) agonist. Combination therapy as used herein is intended to cover when agents are administered before or after each other (sequential therapy), as well as when agents are administered at the same time. It is noted that treatment of one agent before another is referred to herein as sequential therapy, even if the agents are also administered together.

EXAMPLES

Preparation of Hydroxysteroid Dehydrogenase Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (enantiomers, diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) that they can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, *Protecting Groups in Organic Synthesis*, $3^{rd}$ edition, John Wiley & Sons, Inc. 1999.

Compounds according to the present invention may be conveniently prepared, or formed during the process of the invention, as solvates (e.g. hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams);
mg (milligrams);
L (liters);
mL (milliliters);
µL (microliters);
psi (pounds per square inch);
M (molar);
mM (millimolar);
i.v. (intravenous);
Hz (Hertz);
MHz (megahertz);
mol (moles);
mmol (millimoles);
RT (ambient temperature);
min (minutes);
h (hours);
mp (melting point);
TLC (thin layer chromatography);
Tr (retention time);
RP (reverse phase);
MeOH (methanol);
i-PrOH (isopropanol);
TEA (triethylamine);
TFA (trifluoroacetic acid);
TFAA (trifluoroacetic anhydride);
THF (tetrahydrofuran);
DMSO (dimethylsulfoxide);
EtOAc (ethyl acetate);
DME (1,2-dimethoxyethane);

-continued

DCM (dichloromethane);
DCE (dichloroethane);
DMF (N,N-dimethylformamide);
DMPU (N,N'-dimethylpropyleneurea);
CDI (1,1-carbonyidiimidazole);
IBCF (isobutyl chloroformate);
HOAc (acetic acid);
HOSu (N-hydroxysuccinimide);
HOBT (1-hydroxybenzotriazole);
Et$_2$O (diethyl ether);
EDCI (ethylcarbodiimide hydrochloride);
BOC (tert-butyloxycarbonyl);
FMOC (9-fluorenylmethoxycarbonyl);
DCC (dicyclohexylcarbodiimide);
CBZ (benzyloxycarbonyl);
Ac (acetyl);
atm (atmosphere);
TMSE (2-(trimethylsilyl)ethyl);
TMS (trimethylsilyl);
TIPS (triisopropylsilyl);
TBS (t-butyldimethylsilyl);
DMAP (4-dimethylaminopyridine);
Me (methyl);
OMe (methoxy);
Et (ethyl);
Et (ethyl);
tBu (tert-butyl);
HPLC (high pressure liquid chromatography);
BOP (bis(2-oxo-3-oxazolidinyl)phosphinic chloride);
TBAF (tetra-n-butylammonium fluoride);
mCPBA (meta-chloroperbenzoic acid).

All references to ether or Et$_2$O are to diethyl ether; brine refers to a saturated aqueous solution of NaCl. Unless otherwise indicated, all temperatures are expressed in ° C. (degrees Centigrade). All reactions conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The entire disclosures of all documents cited throughout this application are incorporated herein by reference.

Synthetic Schemes for Hydroxysteroid Dehydrogenase Inhibitors of the Present Invention Hydroxysteroid dehydrogenase inhibitors according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Scheme 1

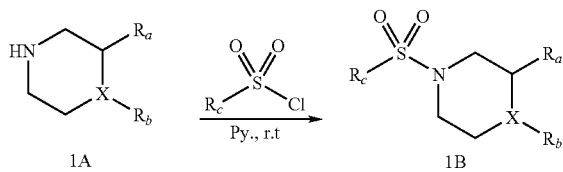

Compound IA (0.10 mmol) is dissolved in pyridine (1.0 mL). A sulfonyl chloride (1 to 3 equivalents) is added, followed by DMAP. The reaction mixture can be stirred at room temperature until no further progression is observed, the solvent can be evaporated in vacuo and the resulting crude mixture can be purified by HPLC to afford Compound 1B (yield 30-90%).

Scheme 2:
Step A-Hydrogenation of aromatic nitro to aniline:

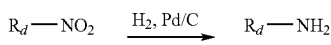

The aromatic nitro compound (0.05 mmole) is dissolved or suspended in EtOH, followed by addition of a catalytic amount of palladium on active carbon. The reaction flask is then charged with hydrogen in a balloon. The nitro group can be converted to the amino group within 15 hours. The reaction mixture can then be filtered to remove the catalyst. The desired product can be obtained in >90% yield and ready to use.

Step B—Piperazine Formation from N,N-bis(2-chloroethyl)arylsulfonamide

Step B - Piperazine formation from N,N-bis(2-chloroethyl)arylsulfonamide:

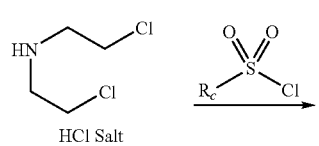

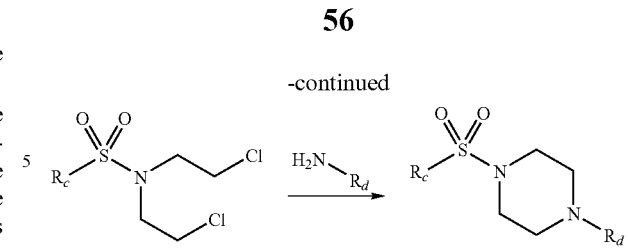

N,N-bis(2-chloroethyl)arylsulfonamide can be prepared from bis(2-chloroethyl)amine (10 mmol) and the corresponding sulfonyl chloride (10 mmole) in 50 ml dry pyridine at ambient temperature for 2 hours. Pyridine can be removed and the mixture can be extracted with EtOAc and water. The organic layer can be acidified with 0.1 N HCl, washed with water and dried. The desired N,N-bis(2-chloroethyl)sulfonamide is obtained in the form of an oil.

The N,N-bis(2-chloroethyl)sulfonamide (1.0 mmole) and the corresponding amine (1.0 mmol) are dissolved in n-BuOH (2.0 ml). The mixture can be heated at 85° C. for 3 hours. Potassium carbonate (1.0 mmol) is added and the mixture heated to 85° C. for an additional 24 h. The crude product can be purified by preparative HPLC to give the desired product (yield 15-75%).

Scheme 3:

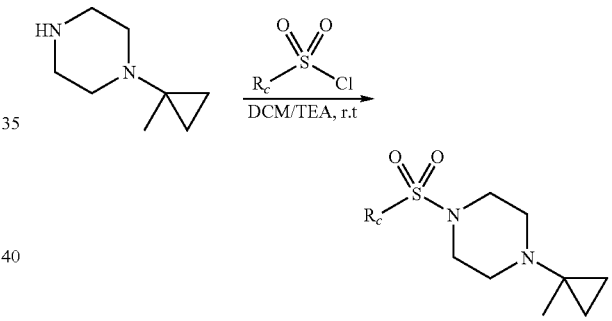

1-(1-Methylcyclopropyl)piperazine (TFA salt) (50.9 mg, 0.20 mmol) is dissolved in dichloromethane (1.0 mL) and NEt$_3$ (0.3 mL) is added. To this mixture, a sulfonyl chloride (0.300 mmol) is added and the reaction mixture stirred at room temperature for 1 h. The solvent is evaporated in vacuo and the resulting crude mixture purified by HPLC with acetonitrile in water (0.05 TFA buffer). The product containing fractions are concentrated in vacuo until only water is left, basified with NaHCO$_3$ (sat. aq., 20 mL) and extracted with dichloromethane (3×7 mL). The combined organic extracts are dried (MgSO$_4$), filtered and concentrated in vacuo to afford the desired product.

Scheme 4:

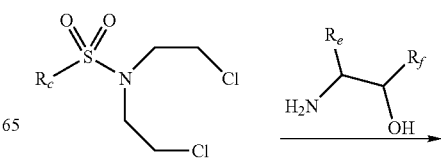

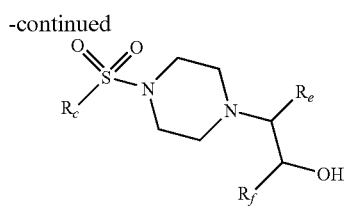

The N,N-bis(2-chloroethyl)sulfonamide and the corresponding amino alcohol (1.0 equivalent) are dissolved in n-BuOH (2.0 ml). The mixture can be heated at 85° C. for 3 hours. Potassium carbonate (1.0 mmol) is added and the mixture heated to 85° C. for an additional 24 h. The crude product can be purified by preparative HPLC to give the desired product (yield 15-75%).

Scheme 5:

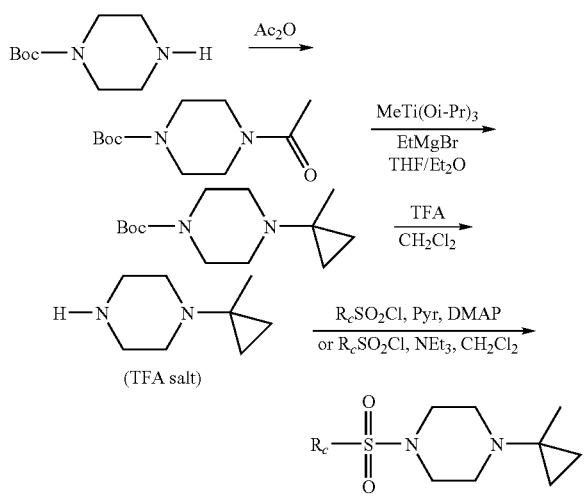

The key cyclopropyl-containing amine can be prepared from the corresponding N-Boc-piperazine by acylation and Kulinkovich cyclopropanation, followed by removal of the Boc moiety. The resulting amine (as a TFA salt) can then be used in the preparation of the desired sulfonamides using sulfonyl chlorides and either pyridine-DMAP or NEt$_3$-CH$_2$Cl$_2$.

Tert-Butyl piperazine-1-carboxylate (4.00 g, 21.4 mmol) is dissolved in dichloromethane (40 mL), cooled to 0° C. and treated with acetic anhydride (2.23 mL, 23.6 mmol) over a period of 2 min. The reaction mixture is stirred at 0° C. for 30 min, LCMS analysis used to indicate completion of the reaction and the volatiles evacuated in vacuo. The residue is treated carefully with NaHCO$_3$ (sat. aq., 50 mL), stirred vigorously for 30 min and the resulting mixture extracted with diethyl ether (4×20 mL). The combined organic extracts are dried (MgSO$_4$), filtered and concentrated in vacuo to afford tert-Butyl-4-acetylpiperazine-1-carboxylate as a white solid (4.53 g, 93%). $^1$H NMR (400 MHz, DMSO-D6) δ ppm 1.39 (s, 9H), 1.99 (s, 3H), 3.22-3.29 (m, 2H), 3.30-3.34 (m, 2H), 3.36-3.41 (m, 4H); ESI-MS: m/z 229.3 (M+H)$^+$.

Tert-Butyl-4-acetylpiperazine-1-carboxylate (3.90 g, 17.1 mmol) is dissolved in anhydrous THF and cooled to −78° C. in nitrogen atmosphere. To this solution is added MeTi(O-iPr)$_3$ (1.0 M in THF, 20.5 mL, 20.5 mmol) over a period of 3 min, followed by EtMgBr (3.0 M in Et$_2$O, 22.0 mL, 66.0 mmol) over a period of 7 min. The reaction mixture is allowed to warm to room temperature during which time it changes from a clear red to a viscous black liquid and gas evolution is observed. The flask can be shaken intermittingly to ensure continuous stirring and LCMS analysis can be used to show the absence of the starting amide. Typically, the reaction is complete after 30 min of stirring. The reaction mixture is then carefully diluted with water (20 mL) and a Rochelle salt solution (20% aq., 50 mL). The mixture is stirred vigorously for 15 min, the upper layer liquid decanted off and the precipitate triturated with EtOAc (3×50 mL). The precipitate is then filtered off using a celite plug (10 g) that has been washed well with EtOAc (20 mL). The initially decanted liquid, the triturates and the filtrate are then combined and extracted with EtOAc (4×50 mL). The combined extracts are dried (MgSO$_4$), filtered and concentrated in vacuo to afford the crude product as a clear oil (4.0 g). Column chromatography (250 g SiO$_2$, hexanes-ethyl acetate 4:1, 2 L) affords tert-butyl-4-(1-methylcyclopropyl)piperazine-1-carboxylate as a white solid (2.46 g, 60%). $^1$H NMR (400 MHz, DMSO-D6) δ ppm 0.29-0.33 (m, 2H), 0.43-0.47 (m, 2H), 0.97 (s, 3H), 1.38 (s, 9H), 2.44-2.48 (m, 4H), 3.17-3.27 (m, 4H); ESI-MS: m/z 229.2 (M+H)$^+$.

Tert-Butyl-4-(1-methylcyclopropyl)piperazine-1-carboxylate (2.22 g, 9.24 mmol) is dissolved in dichloromethane (50 mL) and treated with TFA (6 mL). The reaction mixture can be stirred at room temperature for 12 h and the volatiles evaporated in vacuo. The residue is treated with NaHCO$_3$ (sat. aq., 150 mL), stirred for 15 min and extracted with EtOAc (8×60 mL). The combined organic extracts are dried (MgSO$_4$), filtered and concentrated in vacuo to afford 1-(1-methylcyclopropyl)piperazine, TFA salt, as an off-white solid (1.54 g, 65%). $^1$H NMR (400 MHz, DMSO-D6) δ ppm 0.31-0.39 (m, 2H), 0.41-0.48 (m, 2H), 1.01 (s, 3H), 2.61-2.70 (m, 4H), 2.89-3.00 (m, 4H), 8.11 (br s, 2H); ESI-MS: m/z 141.1 (M+H)$^+$.

An additional batch of 1-(1-methylcyclopropyl)piperazine, TFA salt, can be obtained as follows: the water layer left after EtOAc extraction is basified to pH 14 with NaOH (19M, 5 mL) and extracted with EtOAc (2×100 mL). The combined organic extracts are dried (MgSO$_4$), filtered and concentrated in vacuo to afford the title compound as an off-white solid (0.692 g, 30%).

Scheme 6:

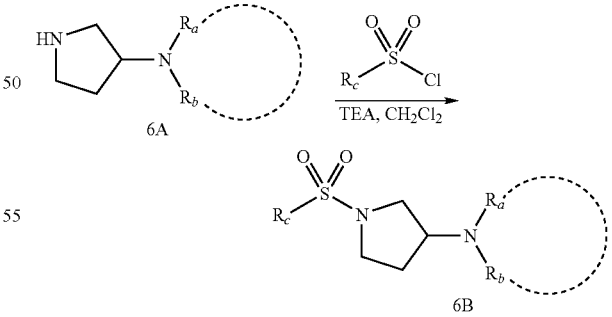

Compound 6A (0.10 mmol) and triethylamine (1 to 3 equivalents) are dissolved in CH$_2$Cl$_2$ (0.5 mL). A sulfonyl chloride (1 to 3 equivalents) is added, and the mixture is stirred at room temperature until no further progression is observed. Volatiles can be evaporated in vacuo and the resulting crude mixture can be purified by chromatography to afford Compound 6B (yield 30 to 90%).

Scheme 7:

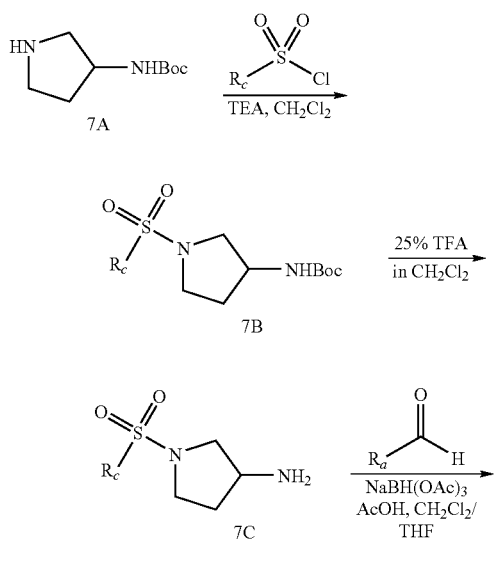

ride (1 to 3 equivalents) is added, and the mixture is stirred at room temperature until no further progression is observed. Volatiles can be evaporated in vacuo and the resulting crude mixture can be purified by chromatography to afford Compound 7B. An ice-cooled 25% TFA solution in $CH_2Cl_2$ is added to Compound 7B, and the mixture is stirred at 0° C. to room temperature for 0.5 to 18 h. Volatiles are evaporated in vacuo and the resulting crude mixture is triturated with ether to give Compound 7C as the TFA salt. Compound 7C and an aldehyde (1 equivalent) are dissolved in a 1:1 mixture of $CH_2Cl_2$ and THF. Sodium triacetoxyborohydride (1 to 2 equivalents) is added to the reaction mixture at 0° C. and the mixture is stirred at room temperature until no further progression is observed. The reaction is quenched with a saturated solution of sodium bicarbonate, and is extracted 3 times with EtOAc. Combined organic layers are dried over $MgSO_4$, filtered and concentrated in vacuo to give the crude product, which can be purified by chromatography to give Compound 7D (yield 80 to 85%). Alternatively, Compound 7C and a dihaloalkane (1 equivalent) are stirred in a DMF in the presence of $Et_3N$ (1 to 3 equivalents) at 60 to 150° C. until no further progression is observed. Brine is added to the cooled mixture, which is then extracted with EtOAc three times. Combined organic layers are dried over $MgSO_4$, filtered and concentrated in vacuo to give the crude product, which can be purified by chromatography to give Compound 7E.

Scheme 8:

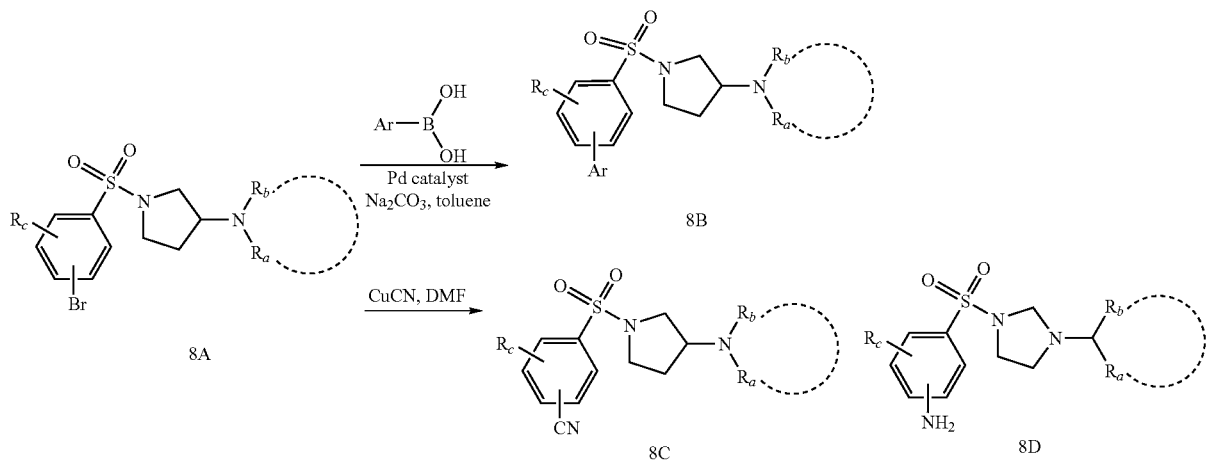

-continued

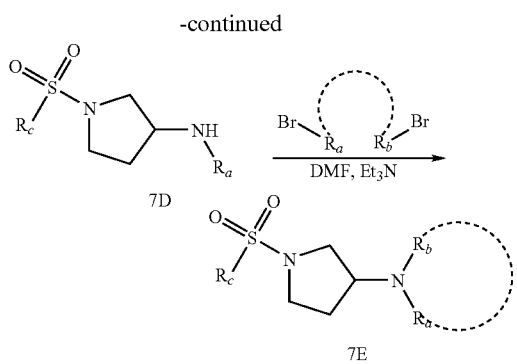

Compound 7A (1.0 mmol) and triethylamine (1 to 3 equivalents) are dissolved in $CH_2Cl_2$ (5 mL). A sulfonyl chlo- Compound 8A (1.0 mmol), an aryl or heteroaryl boronic acid (1 to 3 equivalents), a catalyst such as tetrakis(triphenylphosphine)palladium (1 to 10 mol %), and a 2N aqueous solution of $Na_2CO_3$ are mixed in toluene (5 mL). The mixture is heated to 85 to 120° C. for 8 to 18 h. After mixture is cooled, a saturated solution of sodium bicarbonate is added, and the mixture is extracted 3 times with EtOAc. Combined organic layers are dried over $MgSO_4$, filtered and concentrated in vacuo to give the crude product, which can be purified by chromatography to give Compound 8B. Alternatively, Compound 8A and copper(I) cyanide are mixed in DMF and are heated to 100-150° C. for 10-20 h. After mixture is cooled, a saturated solution of sodium bicarbonate is added, and the mixture is extracted 3 times with EtOAc. Combined organic layers are dried over $MgSO_4$, filtered and concentrated in vacuo to give the crude product, which can be purified by chromatography to give Compound 8C, along with by-product Compound 8D.

Scheme 9:

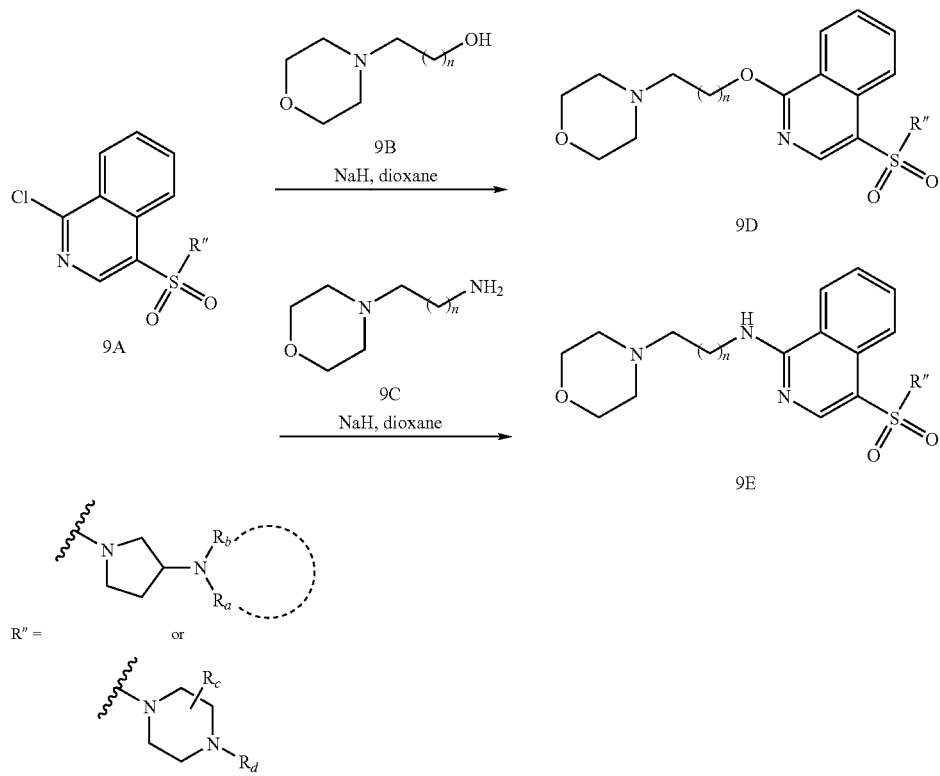

Sodium hydride (1 to 2 equivalents) is added to a solution of Compound 9B (1.0 mmol) in dioxane. The mixture was stirred until no more gas evolution is observed. Compound 9A (0.6 equivalent) is added to the reaction mixture and the mixture is heated to 80-120° C. for 2-18 hours. The cooled mixture is extracted into EtOAc from saturated $NaHCO_3$. Combined organic layers are dried over $MgSO_4$, filtered and concentrated in vacuo to give the crude product, which can be purified by chromatography to give Compound 9D (yield 60 to 70%). Alternatively, Compound 9A (1.0 mmol) and Compound 9C (1 equivalent) are stirred in EtOH (10 ml) at 80 to 180° C. in a sealed tube for 10 to 60 minutes. Solvents can be removed in vacuo, and the crude product can be purified be purified by chromatography to give Compound 9E (yield 50 to 60%).

Scheme 10:

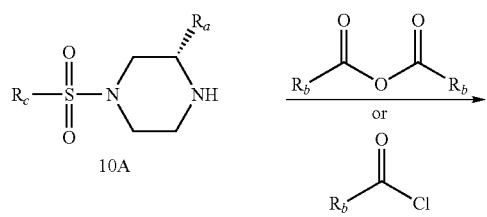

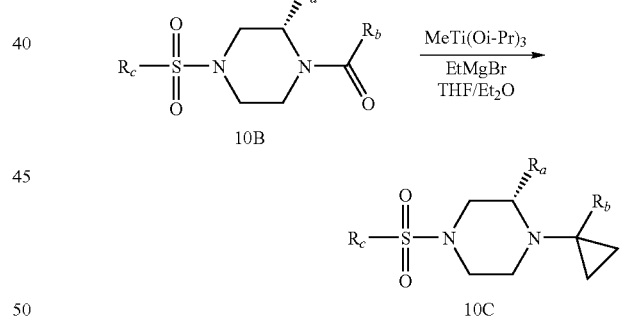

Compound 10A (20 mmol) is dissolved in dichloromethane (40 mL), cooled to 0° C. and treated with an acid anhydride or an acid chloride (1 to 2 equivalent). The reaction mixture is stirred at 0° C. for 30 min to 3 h, LCMS analysis used to indicate completion of the reaction and the volatiles evacuated in vacuo. The residue is treated carefully with $NaHCO_3$, stirred vigorously for 30 min and the resulting mixture extracted with diethyl ether 4 times. The combined organic extracts are dried ($MgSO_4$), filtered and concentrated in vacuo to afford Compound 10B (yield 90 to 99%). Compound 10B is dissolved in anhydrous THF and cooled to −78° C. in nitrogen atmosphere. To this solution is added MeTi $(OiPr)_3$ (1.2 equivalents) over a period of 5 to 10 minutes, followed by EtMgBr (1.3 equivalents) over 5 to 10 min. The reaction mixture is allowed to warm to room temperature and is stirred continuously for 30 min to 3 h. The reaction mixture is then carefully diluted with water and a Rochelle salt solution (20% aq.) The mixture is stirred vigorously for 15 to 30 min, the upper layer liquid decanted off and the precipitate triturated three times with EtOAc. The precipitate is removed by filtration through a pad of Celite that has been washed well with EtOAc. The initially decanted liquid, the triturates and the filtrate are then combined and extracted four times with EtOAc. The combined extracts are dried over MgSO$_4$, filtered and concentrated to afford the crude product. Column chromatography affords Compound 10C (yield 50 to 70%).

Scheme 11:

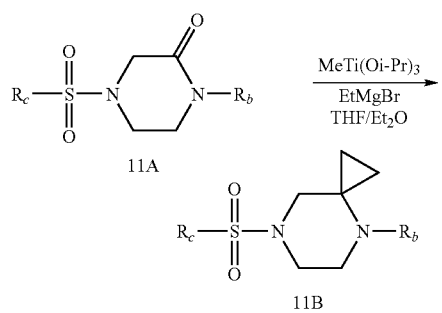

11A

11B

Compound 11A is dissolved in anhydrous THF and cooled to −78° C. in nitrogen atmosphere. To this solution is added MeTi(OiPr)$_3$ (1.2 equivalents) over a period of 5 to 10 minutes, followed by EtMgBr (1.3 equivalents) over 5 to 10 min. The reaction mixture is allowed to warm to room temperature and is stirred continuously for 30 min to 3 h. The reaction mixture is then carefully diluted with water and a Rochelle salt solution (20% aq.) The mixture is stirred vigorously for 15 to 30 min, the upper layer liquid decanted off and the precipitate triturated three times with EtOAc. The precipitate is removed by filtration through a pad of Celite that has been washed well with EtOAc. The initially decanted liquid, the triturates and the filtrate are then combined and extracted four times with EtOAc. The combined extracts are dried over MgSO$_4$, filtered and concentrated to afford the crude product. Column chromatography affords Compound 11C (yield 50 to 70%).

For example, the above reaction schemes, and variations thereof, can be used to prepare the following:

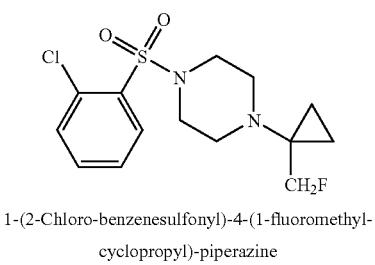

1-(2-Chloro-benzenesulfonyl)-4-(1-fluoromethyl-cyclopropyl)-piperazine

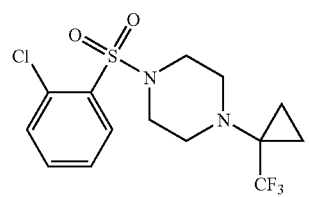

1-(2-Chloro-benzenesulfonyl)-4-(1-trifluoromethyl-cyclopropyl)-piperazine

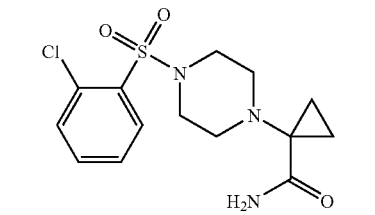

1-[4-(2-Chloro-benzenesulfonyl)-piperazin-1-yl]-cyclopropanecarboxylic acid amide

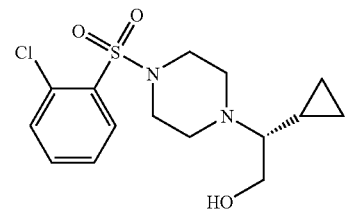

2-[4-(2-Chloro-benzenesulfonyl)-piperazin-1-yl]-2-cyclopropyl-ethanol

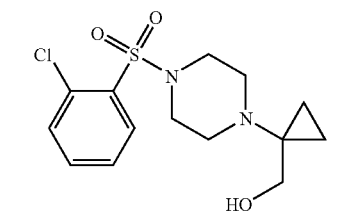

{1-[1-(2-Chloro-benzenesulfonyl)-piperidin-4-yl]-cyclopropyl}-methanol

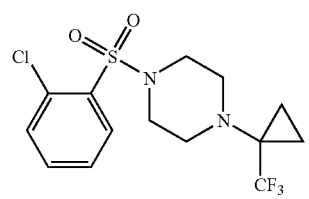

1-(2-Chloro-benzenesulfonyl)-4-(1-trifluoromethyl-cyclopropyl)-piperidine

-continued

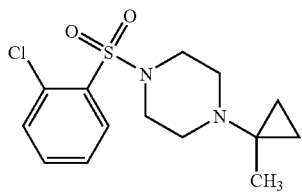

1-(2-Chloro-benzenesulfonyl)-4-(1-methyl-cyclopropyl)-piperidine

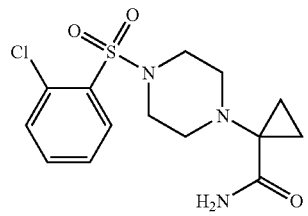

1-[1-(2-Chloro-benzenesulfonyl)-piperidin-4-yl]-cyclopropanecarboxylic acid amide

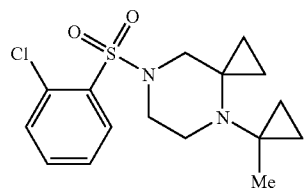

7-(2-Chloro-benzenesulfonyl)-4-(1-methyl-cyclopropyl)-4,7-diaza-spiro[2.5]octane

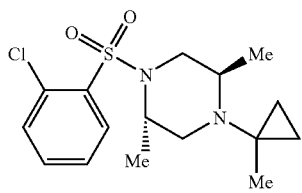

1-(2-Chloro-benzenesulfonyl)-2,5-dimethyl-4-(1-methyl-cyclopropyl)-piperazine

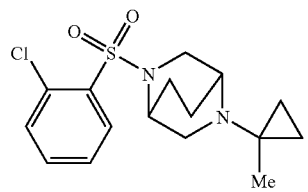

2-(2-Chloro-benzenesulfonyl)-5-(1-methyl-cyclopropyl)-2,5-diaza-bicyclo[2.2.2]octane

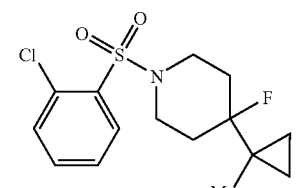

1-(2-Chloro-benzenesulfonyl)-4-fluoro-4-(1-methyl-cyclopropyl)-piperidine

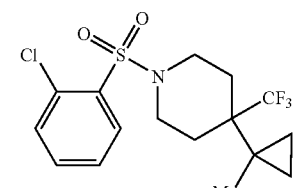

1-(2-Chloro-benzenesulfonyl)-4-(1-methyl-cyclopropyl)-4-trifluoromethyl-piperidine

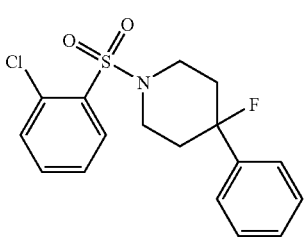

1-(2-Chloro-benzenesulfonyl)-4-fluoro-4-phenyl-piperidine

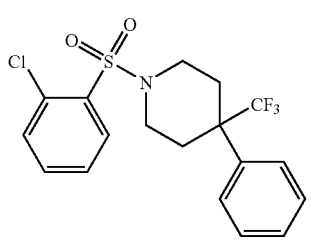

1-(2-Chloro-benzenesulfonyl)-4-phenyl-4-trifluoromethyl-piperidine

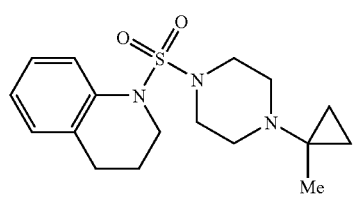

1-[4-(1-Methyl-cyclopropyl)-piperazine-1-sulfonyl]-1,2,3,4-tetrahydro-quinoline

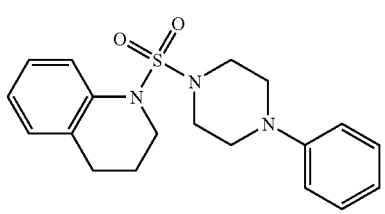

1-(4-Phenyl-piperazine-1-sulfonyl)-1,2,3,4-tetrahydro-quinoline

-continued

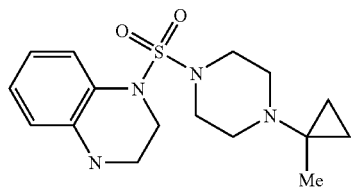

1-[4-(1-Methyl-cyclopropyl)-piperazine-1-sulfonyl]-1,2,3,4-tetrahydro-quinoxaline

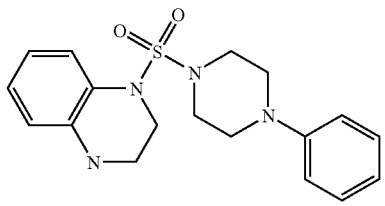

1-(4-Phenyl-piperazine-1-sulfonyl)-1,2,3,4-tetrahydro-quinoxaline

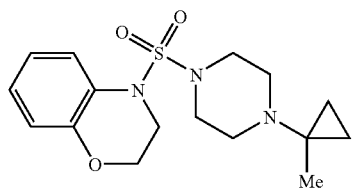

4-[4-(1-Methyl-cyclopropyl)-piperazine-1-sulfonyl]-3,4-dihydro-2H-benzo[1,4]oxazine

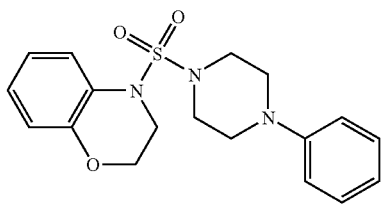

4-(4-Phenyl-piperazine-1-sulfonyl)-3,4-dihydro-2H-benzo[1,4]oxazine

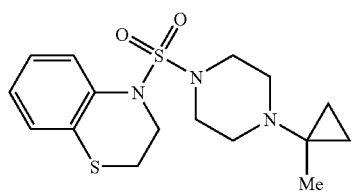

4-[4-(1-Methyl-cyclopropyl)-piperazine-1-sulfonyl]-3,4-dihydro-2H-benzo[1,4]thiazine

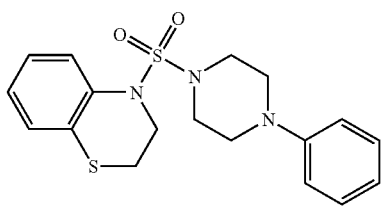

4-(4-Phenyl-piperazine-1-sulfonyl)-3,4-dihydro-2H-benzo[1,4]thiazine

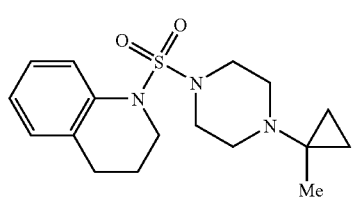

1-[4-(1-Methyl-cyclopropyl)-piperazine-1-sulfonyl]-1,2,3,4-tetrahydro-quinoline

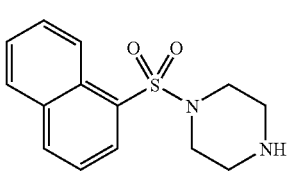

1-(Naphthalen-1-ylsulfonyl)piperazine

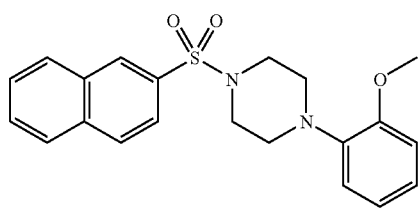

1-(2-Methoxy-phenyl)-4-(naphthalene-2-sulfonyl)-piperazine

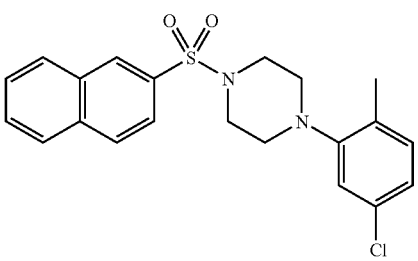

1-(5-Chloro-2-methyl-phenyl)-4-(naphthalene-2-sulfonyl)-piperazine

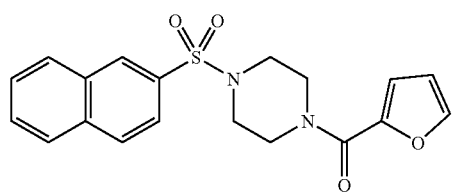

Furan-2-yl-[4-(naphthalene-2-sulfonyl)-piperazin-1-yl]-methanone

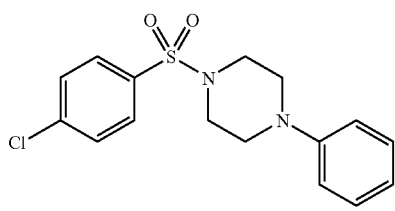

1-(4-Chlorophenylsulfonyl)-4-phenylpiperazine

-continued

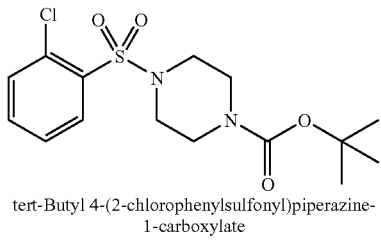
tert-Butyl 4-(2-chlorophenylsulfonyl)piperazine-1-carboxylate

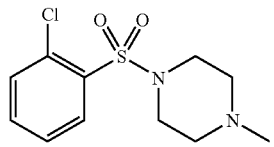
1-(2-Chlorophenylsulfonyl)-4-methylpiperazine

In each of the above reaction procedures or schemes, the various substituents may be selected from among the various substituents otherwise taught herein.

Descriptions of the syntheses of particular compounds according to the present invention based on the above reaction scheme are set forth herein.

Examples of Hydroxysteroid Dehydrogenase Inhibitors

The present invention is further exemplified, but not limited by, the following examples that describe the synthesis of particular compounds according to the invention.

Example 1

1-Phenyl-4-(m-tolylsulfonyl)piperazine

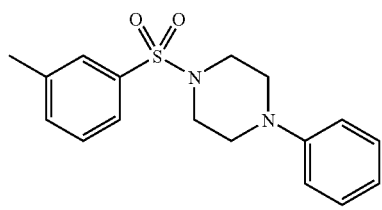

The title compound was prepared as described in the Scheme 1. $^1$H NMR (400 MHz, DMSO-D6) δ ppm 2.41 (s, 3H), 2.96-3.01 (m, 4H), 3.16-3.21 (m, 4H), 6.76-6.81 (m, 1H), 6.88 (d, J=8.84 Hz, 2H), 7.18 (t, J=7.71 Hz, 2H), 7.55 (s, 3H), 7.57 (s, 1H); ESI-MS: m/z 317.1 (M+H)$^+$.

Example 2

1-(3-Methoxyphenylsulfonyl)-4-phenylpiperazine

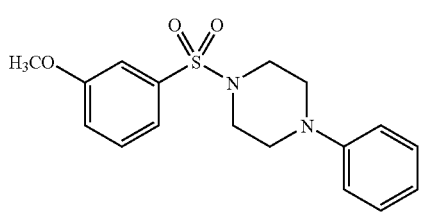

The title compound was prepared as described in the Scheme 1. $^1$H NMR (400 MHz, DMSO-D6) δ ppm 3.00 (s, 1H), 3.02 (d, J=5.31 Hz, 3H), 3.18 (d, J=5.05 Hz, 3H), 3.20 (s, 1H), 3.84 (s, 3H), 6.78 (t, J=6.95 Hz, 1H), 6.89 (d, J=8.59 Hz, 2H), 7.16-7.21 (m, 3H), 7.28-7.34 (m, 2H), 7.58 (t, J=7.96 Hz, 1H); ESI-MS: m/z 333.1 (M+H)$^+$.

Example 3

1-(3-Phenoxyphenylsulfonyl)-4-phenylpiperazine

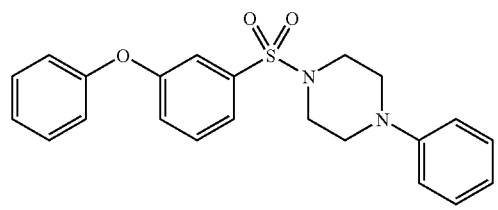

The title compound was prepared as described in the Scheme 1. $^1$H NMR (400 MHz, DMSO-D6) δ ppm 2.99-3.03 (m, 4H), 3.16-3.21 (m, 4H), 6.80 (t, J=7.07 Hz, 1H), 6.90 (d, J=8.34 Hz, 2H), 7.12 (d, J=7.83 Hz, 2H), 7.21 (ddd, J=10.74, 7.71, 7.58 Hz, 4H), 7.35 (dd, J=8.21, 2.65 Hz, 1H), 7.41-7.47 (m, 2H), 7.51 (d, J=7.83 Hz, 1H), 7.67 (t, J=7.96 Hz, 1H); ESI-MS: m/z 395.1 (M+H)$^+$.

Example 4

1-(3-Chloro-2-methylphenylsulfonyl)-4-phenylpiperazine

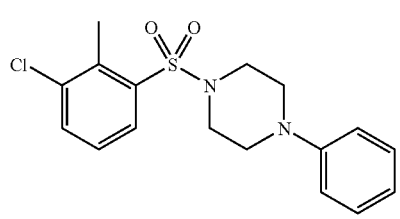

The title compound was prepared as described in the Scheme 1. $^1$H NMR (400 MHz, DMSO-D6) δ ppm 2.63 (s, 3H), 3.19 (q, J=5.98 Hz, 8H), 6.80 (t, J=7.20 Hz, 1H), 6.92 (d, J=8.08 Hz, 2H), 7.18-7.23 (m, 2H), 7.47 (t, J=7.96 Hz, 1H), 7.80 (d, J=7.33 Hz, 1H), 7.86 (d, J=7.83 Hz, 1H); ESI-MS: m/z 351.1 (M+H)⁺.

Example 5

1-(naphthalen-1-ylsulfonyl)-4-phenylpiperazine

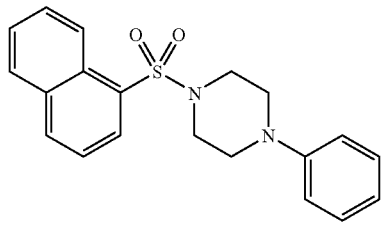

The title compound was prepared as described in the Scheme 1. ¹H NMR (400 MHz, DMSO-D6) δ ppm 3.12 (d, J=3.28 Hz, 4H), 3.16-3.21 (m, 4H), 6.77 (t, J=7.20 Hz, 1H), 6.85 (d, J=7.83 Hz, 2H), 7.16 (t, J=7.96 Hz, 2H), 7.65-7.77 (m, 3H), 8.11 (d, J=8.08 Hz, 1H), 8.15-8.20 (m, 1H), 8.31 (d, J=8.08 Hz, 1H), 8.70 (d, J=8.59 Hz, 1H); ESI-MS: m/z 353.1 (M+H)⁺.

Example 6

1-(2,3-dihydrobenzo[b][1,4]dioxin-6-ylsulfonyl)-4-phenylpiperazine

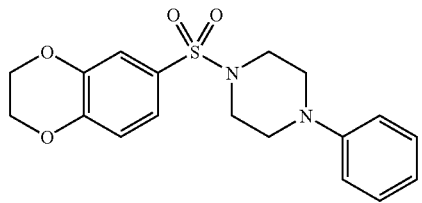

The title compound was prepared as described in the Scheme 1. ¹H NMR (400 MHz, DMSO-D6) δ ppm 2.94-2.99 (m, 4H), 3.18 (d, J=5.31 Hz, 3H), 3.20 (s, 1H), 4.32 (q, J=5.05 Hz, 4H), 6.79 (t, J=7.20 Hz, 1H), 6.89 (d, J=8.34 Hz, 2H), 7.10 (d, J=8.34 Hz, 1H), 7.17-7.24 (m, 4H); ESI-MS: m/z 361.1 (M+H)⁺.

Example 7

1-(4-Phenoxyphenylsulfonyl)-4-phenylpiperazine

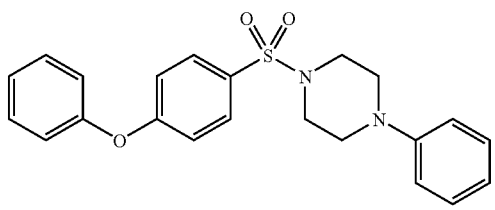

The title compound was prepared as described in the Scheme 1. ¹H NMR (400 MHz, DMSO-D6) δ ppm 2.94-3.02 (m, 4H), 3.13-3.22 (m, 4H), 6.80 (t, J=6.95 Hz, 1H), 6.90 (d, J=8.59 Hz, 2H), 7.14-7.22 (m, 6H), 7.24-7.28 (m, 1H), 7.46 (t, J=7.71 Hz, 2H), 7.74-7.78 (m, 2H); ESI-MS: m/z 395.1 (M+H)⁺.

Example 8

1-(4-Methoxyphenylsulfonyl)-4-phenylpiperazine

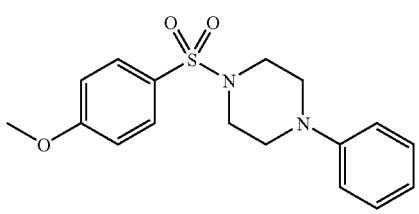

The title compound was prepared as described in the Scheme 1. ¹H NMR (400 MHz, DMSO-D6) δ ppm 2.92-2.99 (m, 4H), 3.18 (d, J=5.31 Hz, 3H), 3.20 (s, 1H), 3.84 (s, 3H), 6.78 (s, 1H), 6.88 (s, 2H), 7.18 (s, 4H), 7.69 (s, 2H); ESI-MS: m/z 333.1 (M+H)⁺.

Example 9

1-(2,4-Dimethoxy-benzenesulfonyl)-4-phenyl-piperazine

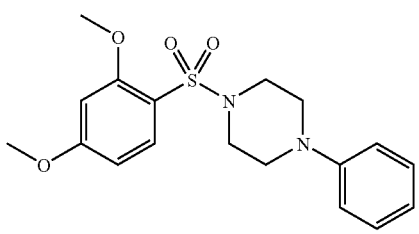

The title compound was prepared as described in the Scheme 1. ESI-MS: m/z 363.1 (M+H)⁺.

Example 10

N-[4-(4-Phenyl-piperazine-1-sulfonyl)-phenyl]-acetamide

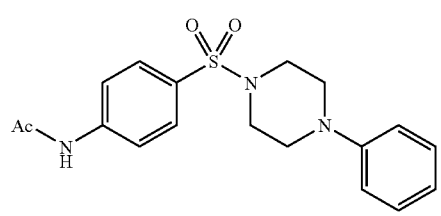

The title compound was prepared as described in the Scheme 1. ESI-MS: m/z 360.1 (M+H)$^+$.

Example 11

1-(2-Chloro-6-methyl-benzenesulfonyl)-4-phenyl-piperazine

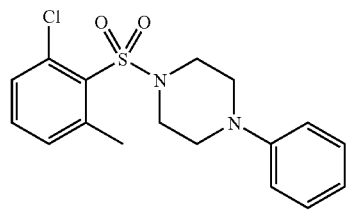

The title compound was prepared as described in the Scheme 1. ESI-MS: m/z 351.1 (M+H)$^+$.

Example 12

1-(2,6-Dichloro-benzenesulfonyl)-4-phenyl-piperazine

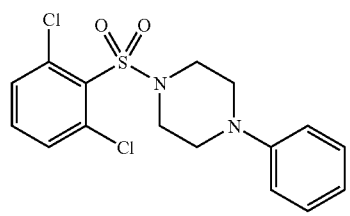

The title compound was prepared as described in the Scheme 1. ESI-MS: m/z 371.0 (M+H)$^+$.

Example 13

1-(2-Chloro-4-fluoro-benzenesulfonyl)-4-phenyl-piperazine

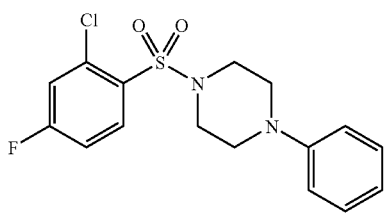

The title compound was prepared as described in the Scheme 1. ESI-MS: m/z 354.1 (M+H)$^+$.

Example 14

1-(2,3-Dichloro-benzenesulfonyl)-4-phenyl-piperazine

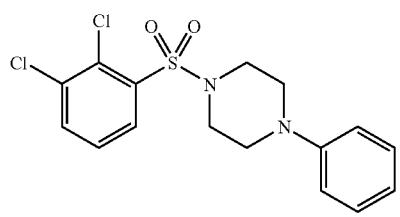

The title compound was prepared as described in the Scheme 1. ESI-MS: m/z 371.0 (M+H)$^+$.

Example 15

1-(2,4-Dichloro-benzenesulfonyl)-4-phenyl-piperazine

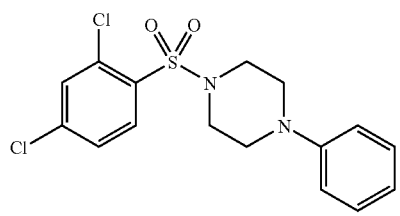

The title compound was prepared as described in the Scheme 1. ESI-MS: m/z 371.0 (M+H)$^+$.

Example 16

1-(3,4-Dimethyl-isoxazole-5-sulfonyl)-4-phenyl-piperazine

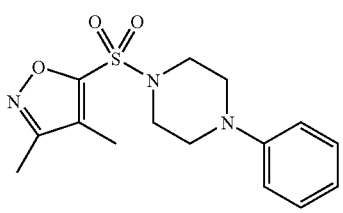

The title compound was prepared as described in the Scheme 1. ESI-MS: m/z 322.1 (M+H)$^+$.

Example 17

1-(1,2-Dimethyl-¹H-imidazole-4-sulfonyl)-4-phenyl-piperazine

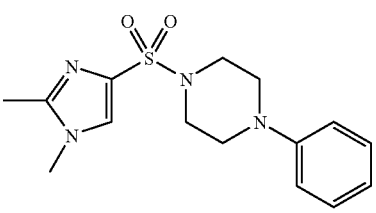

The title compound was prepared as described in the Scheme 1. ESI-MS: m/z 321.1 (M+H)$^+$.

Example 18

1-(Benzofuran-2-sulfonyl)-4-phenyl-piperazine

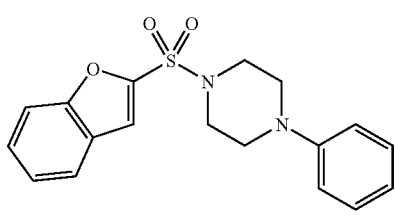

The title compound was prepared as described in the Scheme 1. ESI-MS: m/z 343.1 (M+H)$^+$.

Example 19

6-Methyl-5-(4-phenyl-piperazine-1-sulfonyl)-imidazo[2,1-b]thiazole

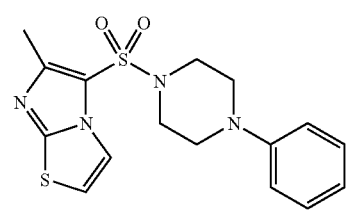

The title compund was prepared as described in the Scheme 1. ESI-MS: m/z 363.1 (M+H)$^+$.

Example 20

5-(4-Phenyl-piperazine-1-sulfonyl)-benzothiazole

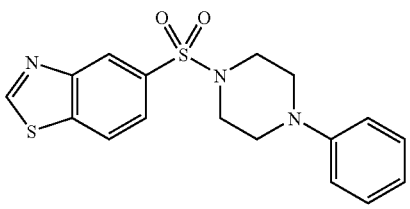

The title compound was prepared as described in the Scheme 1. ESI-MS: m/z 360.1 (M+H)$^+$.

Example 21

2-(4-phenylpiperazin-1-ylsulfonyl)benzonitrile

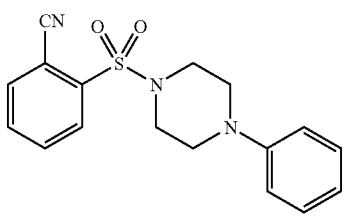

The title compound was prepared as described in the Scheme 1. $^1$H NMR (400 MHz, CHLOROFORM-D) δ ppm 3.25 (s, 4H), 3.41 (s, 4H), 6.91 (t, J=7.96 Hz, 3H), 7.23-7.29 (m, 2H), 7.71 (td, J=7.58, 1.01 Hz, 1H), 7.78 (td, J=7.83, 1.26 Hz, 1H), 7.90 (dd, J=7.58, 1.52 Hz, 1H), 8.06 (dd, J=7.83, 1.26 Hz, 1H); ESI-MS: m/z 328.1 (M+H)$^+$.

Example 22

4-(4-phenylpiperazin-1-ylsulfonyl)benzonitrile

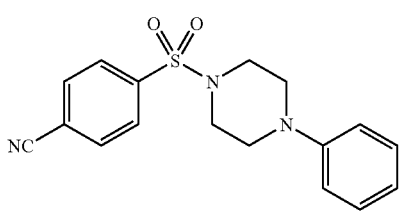

The title compound was prepared as described in the Scheme 1. $^1$H NMR (400 MHz, CHLOROFORM-D) δ ppm 3.23 (d, J=5.56 Hz, 8H), 6.85-6.94 (m, 3H), 7.22-7.29 (m, 2H), 7.84-7.92 (m, 4H); ESI-MS: m/z 328.1 (M+H)+

Example 23

1-(2-chlorophenylsulfonyl)-4-phenylpiperazine

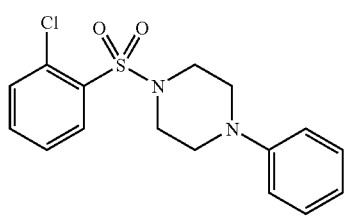

The title compound was prepared as described in the Scheme 1. ¹H NMR (400 MHz, CHLOROFORM-D) δ ppm 3.19 (s, 1H), 3.20-3.23 (m, 3H), 3.42-3.45 (m, 3H), 3.46 (s, 1H), 6.87-6.92 (m, 3H), 7.23-7.30 (m, 2H), 7.41 (td, J=7.45, 1.77 Hz, 1H), 7.47-7.55 (m, 2H), 8.07 (dd, J=7.83, 1.52 Hz, 1H); ESI-MS: m/z 337.1 (M+H)$^+$.

Example 24

1-(3-chlorophenylsulfonyl)-4-phenylpiperazine

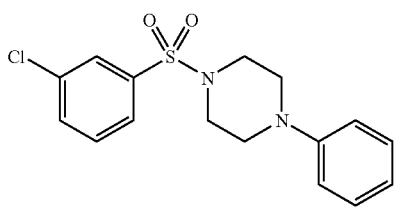

The title compound was prepared as described in the Scheme 1. ¹H NMR (400 MHz, CHLOROFORM-D) δ ppm 3.18-3.22 (m, 4H), 3.23-3.27 (m, 4H), 6.85-6.94 (m, 3H), 7.23-7.28 (m, 3H), 7.50 (t, J=7.96 Hz, 1H), 7.57-7.61 (m, 1H), 7.67 (dt, J=7.83, 1.39 Hz, 1H), 7.77 (t, J=1.89 Hz, 1H); ESI-MS: m/z 337.1 (M+H)$^+$.

Example 25

1-Phenyl-4-(o-tolylsulfonyl)piperazine

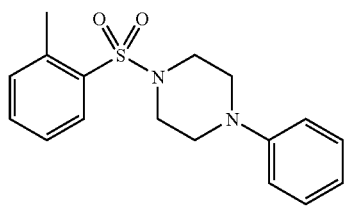

The title compound was prepared as described in the Scheme 1. ¹H NMR (400 MHz, CHLOROFORM-D) δ ppm 2.65 (s, 3H), 3.25 (s, 4H), 3.39 (s, 3H), 7.26-7.36 (m, 4H), 7.47 (t, J=7.45 Hz, 1H), 7.90-7.94 (m, 1H); ESI-MS: m/z 317.1 (M+H)$^+$.

Example 26

1-(2,5-Difluorophenylsulfonyl)-4-phenylpiperazine

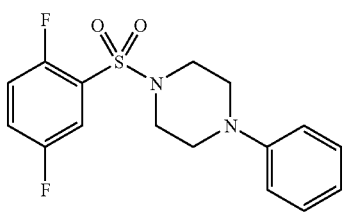

The title compound was prepared as described in the Scheme 1. ¹H NMR (400 MHz, CHLOROFORM-D) δ ppm 3.28 (s, 4H), 3.44 (s, 4H), 6.92-7.04 (m, 3H), 7.19-7.31 (m, 4H), 7.57 (ddd, J=7.71, 4.93, 3.03 Hz, 1H); ESI-MS: m/z 339.1 (M+H)$^+$.

Example 27

8-(4-Phenylpiperazin-1-ylsulfonyl)quinoline

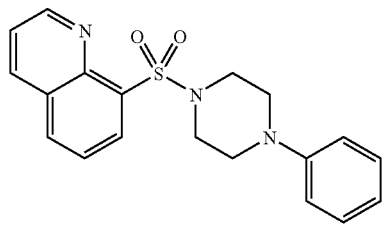

The title compound was prepared as described in the Scheme 1. ¹H NMR (400 MHz, CHLOROFORM-D) δ ppm 3.17-3.27 (m, 4H), 3.64 (s, 4H), 6.90 (d, J=6.06 Hz, 3H), 7.24 (t, J=7.96 Hz, 2H), 7.52 (dd, J=8.34, 4.04 Hz, 1H), 7.63 (t, J=7.71 Hz, 1H), 8.04 (dd, J=8.08, 1.26 Hz, 1H), 8.23 (dd, J=8.34, 1.77 Hz, 1H), 8.50 (dd, J=7.33, 1.52 Hz, 1H), 9.07 (dd, J=4.29, 1.77 Hz, 1H); ESI-MS: m/z 354.1 (M+H)$^+$.

Example 28

1-(3-Chloro-2-fluorophenylsulfonyl)-4-phenylpiperazine

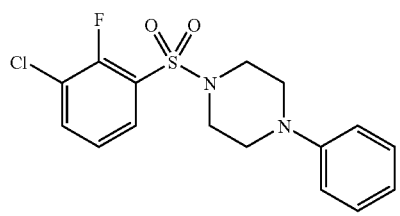

The title compound was prepared as described in the Scheme D. ¹H NMR (400 MHz, CHLOROFORM-D) δ ppm 3.31 (d, J=4.55 Hz, 4H), 3.48 (s, 3H), 6.96-7.08 (m, 3H), 7.25 (t, J=7.58 Hz, 2H), 7.30 (t, J=7.83 Hz, 2H), 7.65 (ddd, J=8.15, 6.63, 1.64 Hz, 1H), 7.76 (ddd, J=7.83, 6.06, 1.77 Hz, 1H); ESI-MS: m/z 355.1 (M+H)⁺.

Example 29

4-(4-Phenylpiperazin-1-ylsulfonyl)benzo[c][1,2,5]thiadiazole

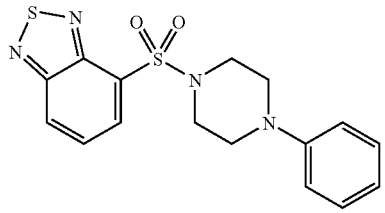

The title compound was prepared as described in the Scheme 1. ¹H NMR (400 MHz, CHLOROFORM-D) δ ppm 3.33 (s, 4H), 3.68 (s, 4H), 7.04 (br, s, 3H), 7.26-7.36 (m, 2H), 7.70-7.75 (m, 1H), 8.26 (d, J=7.83 Hz, 2H); ESI-MS: m/z 361.1 (M+H)⁺.

Example 30

1-(5-Bromo-6-chloropyridin-3-ylsulfonyl)-4-phenylpiperazine

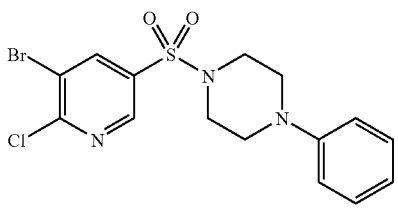

The title compound was prepared as described in the Scheme 1. ¹H NMR (400 MHz, CHLOROFORM-D) δ ppm 3.37 (d, J=5.05 Hz, 4H), 3.44 (s, 3H), 7.12 (s, 3H), 7.34 (t, J=8.08 Hz, 2H), 8.26 (d, J=2.27 Hz, 1H), 8.70 (d, J=2.02 Hz, 1H); ESI-MS: m/z 415.9 (M+H)⁺.

Example 31

1-(6-Morpholinopyridin-3-ylsulfonyl)-4-phenylpiperazine

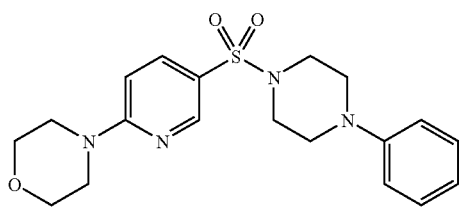

The title compound was prepared as described in the Scheme 1. ¹H NMR (400 MHz, DMSO-D6) δ ppm 3.32 (s, 8H), 4.25-4.31 (m, 4H), 4.51 (s, 4H), 7.04 (d, J=8.34 Hz, 1H), 7.23 (s, 4H), 7.31 (td, J=8.59, 1.77 Hz, 3H); ESI-MS: m/z 389.1 (M+H)⁺.

Example 32

3-(4-Phenylpiperazin-1-ylsulfonyl)benzonitrile

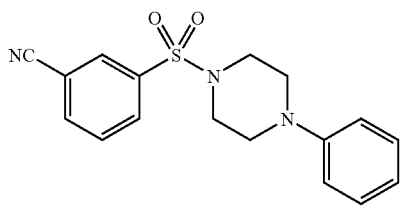

The title compound was prepared as described in the Scheme 1. ¹H NMR (400 MHz, DMSO-D6) δ ppm 4.66 (s, 4H), 7.25 (s, 5H), 7.86 (t, J=7.83 Hz, 1H), 8.38 (d, J=7.33 Hz, 1H), 8.47 (d, J=8.34 Hz, 1H), 8.53 (d, J=6.32 Hz, 1H), 8.71 (d, J=6.32 Hz, 1H), 9.47 (s, 1H); ESI-MS: m/z 328.1 (M+H)⁺.

Example 33

1-(2-Fluorophenylsulfonyl)-4-phenylpiperazine

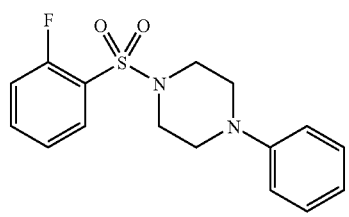

The title compound was prepared as described in the Scheme 1. ¹H NMR (400 MHz, DMSO-D6) δ ppm 3.17 (d, J=5.56 Hz, 6H), 3.19 (s, 2H), 6.79 (t, J=7.20 Hz, 1H), 6.90 (d, J=8.84 Hz, 2H), 7.19 (t, J=7.71 Hz, 2H), 7.45 (t, J=7.71 Hz, 1H), 7.51 (dd, J=10.86, 8.34 Hz, 1H), 7.75-7.83 (m, 2H); ESI-MS: m/z 321.1 (M+H)⁺.

Example 34

1-(2-Bromophenylsulfonyl)-4-phenylpiperazine

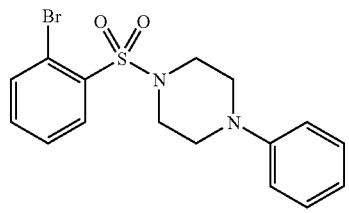

The title compound was prepared as described in the Scheme 1. ¹H NMR (400 MHz, DMSO-D6) δ ppm 3.14-3.20 (m, 4H), 3.30 (d, J=5.31 Hz, 4H), 6.80 (t, J=7.20 Hz, 1H), 6.92 (d, J=8.59 Hz, 2H), 7.17-7.23 (m, 2H), 7.56-7.65 (m, 2H), 7.90 (d, J=6.57 Hz, 1H), 8.03 (dd, J=7.45, 2.15 Hz, 1H); ESI-MS: m/z 381.2, 383.2 (M+H)+.

Example 35

5-(4-Phenylpiperazin-1-ylsulfonyl)benzo[c][1,2,5]thiadiazole

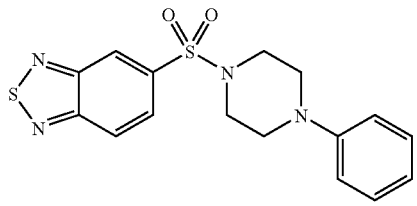

The title compound was prepared as described in the Scheme 1. $^1$H NMR (400 MHz, DMSO-D6) δ ppm 3.18 (d, J=5.56 Hz, 6H), 3.20 (s, 2H), 6.77 (t, J=7.20 Hz, 1H), 6.88 (d, J=8.59 Hz, 2H), 7.14-7.22 (m, 2H), 7.98 (dd, J=9.22, 1.14 Hz, 1H), 8.35 (d, J=9.09. Hz, 1H), 8.56 (d, J=1.77 Hz, 1H); ESI-MS: m/z 361.1 (M+H)+.

Example 36

4-Methyl-7-(4-phenylpiperazin-1-ylsulfonyl)-3,4-dihydro-2 H-benzo[b][1,4]oxazine

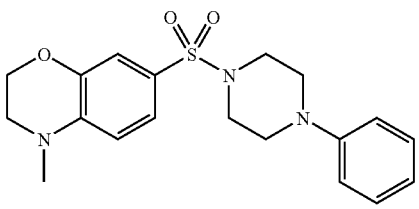

The title compound was prepared as described in the Scheme 1. $^1$H NMR (400 MHz, DMSO-D6) δ ppm 2.89 (s, 3 H), 2.94-3.01 (m, 4 H), 3.18 (M, 4 H), 3.28-3.32 (m, 2 H), 4.27-4.33 (m, 2 H), 6.79 (t, J=7.33 Hz, 1 H), 6.86-6.91 (m, 4 H), 6.93-6.97 (m, 1 H), 7.16-7.22 (m, 2 H); ESI-MS: m/z 374.1 (M+H)+.

Example 37

5-(4-Phenylpiperazin-1-ylsulfonyl)Isoquinoline

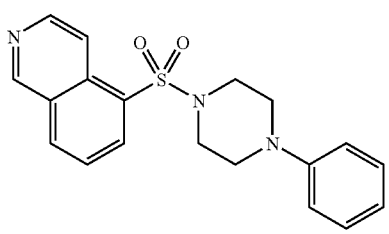

The title compound was prepared as described in the Scheme 1. ESI-MS: m/z 354.1 (M+H)+.

Example 38

1-Phenyl-4-(pyridin-2-ylsulfonyl)piperazine

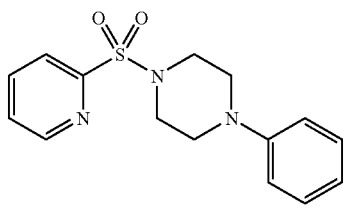

The title compound was prepared as described in the Scheme 1. ESI-MS: m/z 304.1 (M+H)+.

Example 39

4-(4-Phenylpiperazin-1-ylsulfonyl)benzo[c][1,2,5]oxadiazole

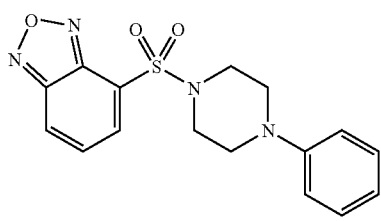

The title compound was prepared as described in the Scheme 1. ESI-MS: m/z 345.1 (M+H)+.

Example 40

1-(3,5-Dimethyl-1 H-pyrazol-4-ylsulfonyl)-4-phenylpiperazine

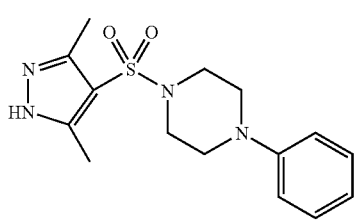

The title compound was prepared as described in the Scheme 1. ESI-MS: m/z 321.1 (M+H)⁺.

Example 41

2-(4-(2-Chlorophenylsulfonyl)piperazin-1-yl)phenol

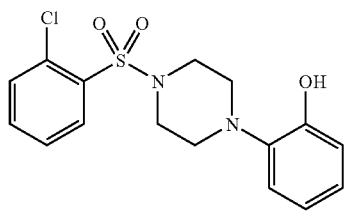

The title compound was prepared as described in the Scheme 1. ESI-MS: m/z 353.1 (M+H)⁺.

Example 42

2-(4-(3-Chlorophenylsulfonyl)piperazin-1-yl)phenol

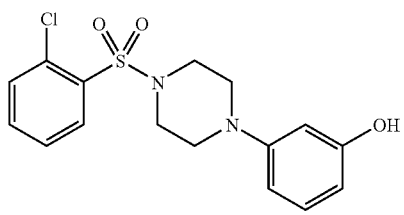

The title compound was prepared as described in the Scheme 1. ESI-MS: m/z 353.1 (M+H)⁺.

Example 43

2-(4-Naphthalen-1-ylsulfonyl)piperazin-1-yl)phenol

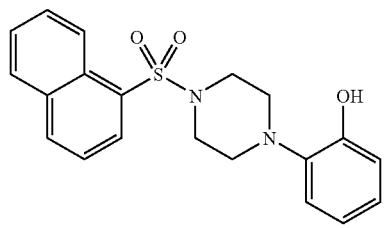

The title compound was prepared as described in the Scheme 1. ¹H NMR (400 MHz, DMSO-D6) δ ppm 2.86-2.96 (m, 4 H), 3.20 (d, J=4.29 Hz, 4 H), 6.67-6.74 (m, 2 H), 6.82 (t, J=8.08 Hz, 2 H), 7.67-7.77 (m, 3 H), 8.13 (d, J=7.83 Hz, 1 H), 8.17 (d, J=7.33 Hz, 1 H), 8.32 (d, J=8.34 Hz, 1 H), 8.74 (d, J=8.59 Hz, 1 H), 8.86 (br, s, 1 H); ESI-MS: m/z 369.1 (M+H)⁺.

Example 44

1-(2-Chlorophenyl)-4-(2-chlorophenylsulfonyl)piperazine

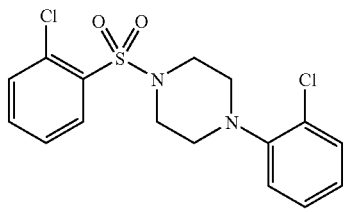

The title compound was prepared as described in the Scheme 1. ESI-MS: m/z 371.1 (M+H)⁺.

Example 45

1-(3-Chlorophenyl)-4-(2-chlorophenylsulfonyl)piperazine

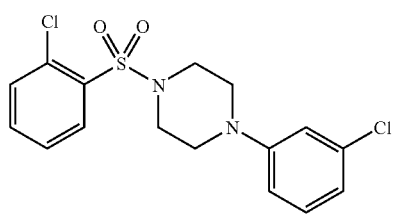

The title compound was prepared as described in the Scheme 1. ESI-MS: m/z 371.1 (M+H)⁺.

Example 46

1-(4-Chlorophenyl)-4-(2-chlorophenylsulfonyl)piperazine

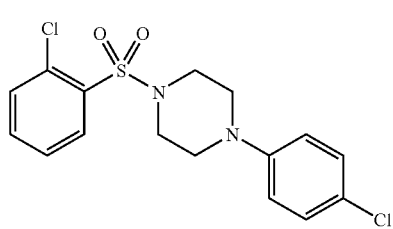

The title compound was prepared as described in the Scheme 1. ESI-MS: m/z 371.1 (M+H)⁺.

Example 47

1-(2-Chlorophenylsulfonyl)-4-(2-methoxyphenyl)piperazine

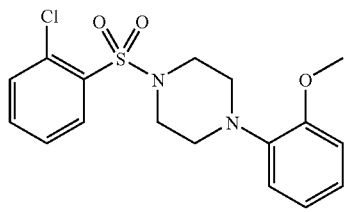

The title compound was prepared as described in the Scheme 1. $^1$H NMR (400 MHz, DMSO-D6) δ ppm 2.95-3.02 (m, 4 H), 3.25-3.32 (m, 4 H), 3.73 (s, 3 H), 6.85-6.89 (m, 2 H), 6.90-6.99 (m, 2 H), 7.60 (dd, J=7.83, 1.77 Hz, 1 H), 7.68-7.75 (m, 2 H), 7.99 (dd, J=7.96, 1.39 Hz, 1 H); ESI-MS: m/z 367.1 (M+H)$^+$.

Example 48

(1R,4S)-2-(4-Chlorophenyl)-5-(2-chlorophenylsulfonyl)-2,5-diaza-bicyclo[2.2.1]heptane

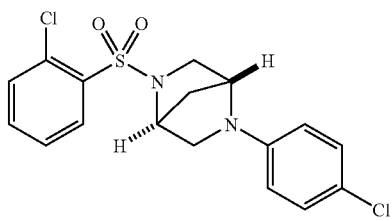

The title compound was prepared as described in the Scheme 1. $^1$H NMR (400 MHz, DMSO-D6) δ ppm 1.73 (s, 1 H), 1.97 (s, 1 H), 3.08 (d, J=9.09 Hz, 1 H), 3.26-3.35 (m, 2 H), 3.52 (dd, J=9.35, 1.77 Hz, 1 H), 4.58 (d, J=10.36 Hz, 2 H), 6.56-6.62 (m, 2 H), 7.14-7.19 (m, 2H), 7.53 (td, J=7.26, 2.15 Hz, 1 H), 7.63-7.70 (m, 2 H), 7.94-7.99 (m, 1 H); ESI-MS: m/z 383.2 (M+H)$^+$.

Example 49

4-(4-(2-Chlorophenylsulfonyl)piperazin-1-yl)benzaldehyde

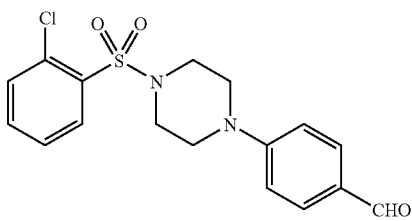

The title compound was prepared as described in the Scheme 1. $^1$H NMR (400 MHz, DMSO-D6) δ ppm 3.27-3.32 (m, 4 H), 3.43-3.49 (m, 4 H), 7.03 (d, J=8.84 Hz, 2 H), 7.57 (d, J=1.01 Hz, 1 H), 7.67-7.73 (m, 4 H), 7.98-8.02 (m, 1 H), 9.71 (s, 1 H); ESI-MS: m/z 364.9 (M+H)$^+$.

Example 50

4-(4-(2-Chlorophenylsulfonyl)piperazin-1-yl)phenol

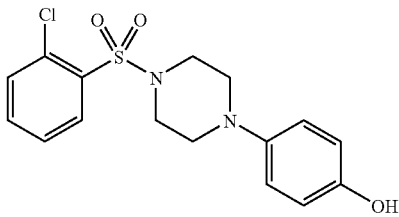

The title compound was prepared as described in the Scheme 1. $^1$H NMR (400 MHz, DMSO-D6) δ ppm 2.95-3.03 (m, 4 H), 3.28 (m, 4 H), 3.81 (br. s, 1 H), 6.61-6.66 (m, 2 H), 6.78 (d, J=8.84 Hz, 2 H), 7.55-7.61 (m, 1 H), 7.70 (ddd, J=17.49, 7.89, 1.64 Hz, 2 H), 7.98-8.01 (m, 1 H); ESI-MS: m/z 353.1 (M+H)$^+$.

Example 51

1-(4-(4-(2-Chlorophenylsulfonyl)piperazin-1-yl)phenyl)ethanone

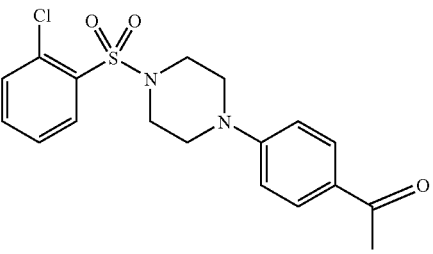

The title compound was prepared as described in the Scheme 1. $^1$H NMR (400 MHz, DMSO-D6) δ ppm 2.42-2.46 (m, 3 H), 3.26-3.31 (m, 4 H), 3.38-3.42 (m, 4 H), 6.96 (d, J=8.84 Hz, 2H), 7.58 (td, J=7.33, 1.26 Hz, 1 H), 7.66-7.73 (m, J=8.21, 8.21, 7.96, 1.39 Hz, 2H), 7.79 (d, J=8.84 Hz, 2 H), 7.98-8.03 (m, 1 H); ESI-MS: m/z 379.1 (M+H)$^+$.

Example 52

1-(2-Chlorophenylsulfonyl)-4-(2-nitrophenyl)piperazine

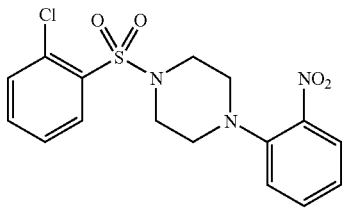

The title compound was prepared as described in the Scheme 1. $^1$H NMR (400 MHz, DMSO-D6) δ ppm 3.03-3.05

(m, 4 H), 3.26-3.28 (m, 4 H), 7.19 (t, J=7.71 Hz, 1 H), 7.37 (d, J=8.08 Hz, 1 H), 7.57-7.62 (m, 2 H), 7.72 (ddd, J=18.13, 8.15, 1.52 Hz, 2 H), 7.82 (dd, J=8.08, 1.26 Hz, 1 H), 7.99 (dd, J=7.96, 1.64 Hz, 1 H); ESI-MS: m/z 382.1 (M+H)⁺.

Example 53

1-(2-Chlorophenylsulfonyl)-4-(3-nitrophenyl)piperazine

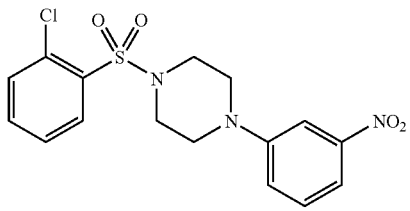

The title compound was prepared as described in the Scheme 1. ¹H NMR (400 MHz, DMSO-D6) δ ppm 3.33 (m, 8 H), 7.36-7.41 (m, 1 H), 7.47 (t, J=8.08 Hz, 1 H), 7.55-7.62 (m, 2 H), 7.65-7.73 (m, 3 H), 7.99-8.03 (m, 1 H); ESI-MS: m/z 382.1 (M+H)⁺.

Example 54

1-(2-Chlorophenylsulfonyl)-4-(4-nitrophenyl)piperazine

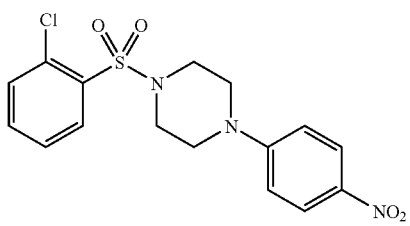

The title compound was prepared as described in the Scheme 1. ¹H NMR (400 MHz, DMSO-D6) δ ppm 3.03-3.05 (m, 4 H), 3.26-3.28 (m, 4 H), 7.17-7.22 (m, 1 H), 7.35-7.39 (m, 1 H), 7.57-7.63 (m, 2 H), 7.68-7.75 (m, 2 H), 7.82 (dd, J=8.08, 1.26 Hz, 1 H), 7.99 (dd, J=7.96, 1.14 Hz, 1 H); ESI-MS: m/z 382.1 (M+H)⁺.

Example 55

2-(4-(2-Chlorophenylsulfonyl)piperazin-1-yl)benzenamine

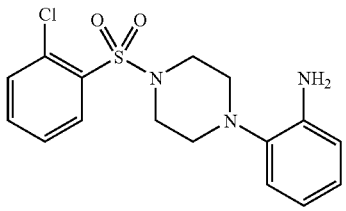

The title compound was prepared as described in the Scheme 2. ¹H NMR (400 MHz, DMSO-D6) δ ppm 2.86 (s, 4 H), 3.27 (m, 4 H), 6.84 (br. S, 2 H), 6.94-7.06 (m, 3 H), 7.15 (d, J=7.83 Hz, 1 H), 7.57-7.65 (m, 1 H), 7.69-7.78 (m, 2 H), 8.01 (d, J=7.83 Hz, 1 H); ESI-MS: m/z 352.1 (M+H)⁺.

Example 56

2-(4-(2-Chlorophenylsulfonyl)piperazin-2-yl)benzenamine

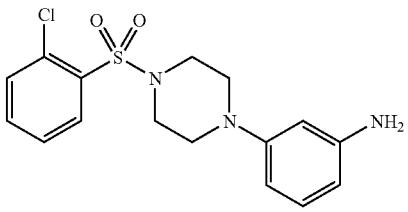

The title compound was prepared as described in the Scheme 2. ¹H NMR (400 MHz, DMSO-D6) δ ppm 2.95-3.02 (m, 4 H), 3.32-3.39 (m, 4 H), 4.88 (br. s, 1 H), 7.08-7.16 (m, 2H), 7.37-7.44 (m, 2 H), 7.57-7.63 (m, 2 H), 7.67-7.76 (m, 2 H), 8.01 (d, J=8.08 Hz, 1 H), 8.08 (s, 1 H); ESI-MS: m/z 352.1 (M+H)⁺.

Example 57

2-(4-(2-Chlorophenylsulfonyl)piperazin-1-yl)benzoic acid

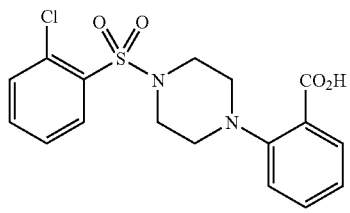

The title compound was prepared as described in the Scheme 1. ¹H NMR (400 MHz, DMSO-D6) δ ppm 3.29-3.31 (m, 4 H), 3.53-3.55 (m, 4 H), 6.99-7.04 (m, 2 H), 7.55-7.60 (m, 1 H), 7.66-7.73 (m, J=8.31, 8.31, 8.02, 1.64 Hz, 2 H), 7.98-8.02 (m, 1 H), 8.02-8.07 (m, 2 H); ESI-MS: m/z 381.1 (M+H)⁺.

Example 58

2-(4-(2-Chlorophenylsulfonyl)piperazin-1-yl)benzamide

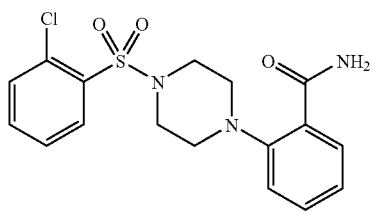

2-(4-(2-Chlorophenylsulfonyl)piperazin-1-yl)benzoic acid (76 mg, 0.02 mmole), EDCI (39 mg, 0.02 mmole), HOBt (31 mg, 0.02 mmole) and ammonium formate (13 mg, 0.02 mmole) were combined in 1 ml of dry DMF. The mixture was treated with 1 equivalent of TEA and stirred at room temperature overnight. The title compound was obtained in yield of 37% after purification on preparative HPLC. $^1$H NMR (400 MHz, DMSO-D6) δ ppm 3.21 (s, 4 H), 3.31 (s, 4 H), 5.87 (br, s, 2 H), 6.68 (s, 1 H), 6.75 (s, 1 H), 6.90 (s, 1 H), 7.26 (s, 1 H), 7.59 (s, 1 H), 7.72 (s, 2 H), 8.02 (s, 1 H); ESI-MS: m/z 380.1 (M+H)$^+$.

Example 59

1-(2-Chlorophenylsulfonyl)-4-(pyridin-2-yl)piperazine

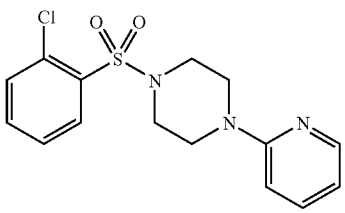

The title compound was prepared as described in the Scheme 1. $^1$H NMR (400 MHz, DMSO-D6) δ ppm 3.23-3.27 (m, 4 H), 3.53-3.57 (m, 4 H), 6.65 (dd, J=7.07, 4.80 Hz, 1 H), 6.82 (d, J=8.59 Hz, 1 H), 7.50-7.59 (m, 2 H), 7.65-7.72 (m, J=8.40, 8.40, 8.21, 1.77 Hz, 2 H), 7.99 (dd, J=7.83, 1.52 Hz, 1 H), 8.09 (dd, J=4.93, 1.89 Hz, 1 H); ESI-MS: m/z 338.1 (M+H)$^+$.

Example 60

1-(Naphthalen-1-ylsulfonyl)-4-(pyridin-2-yl)piperazine

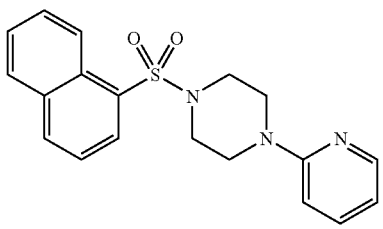

The title compound was prepared as described in the Scheme 1. $^1$H NMR (400 MHz, DMSO-D6) δ ppm 3.12-3.17 (m, 4 H), 3.48-3.54 (m, 4 H), 6.61 (dd, J=7.07, 5.05 Hz, 1 H), 6.75 (d, J=8.59 Hz, 1 H), 7.47 (ddd, J=8.72, 6.95, 2.02 Hz, 1 H), 7.64-7.76 (m, 3 H), 8.04 (dd, J=4.93, 1.39 Hz, 1 H), 8.10 (d, J=7.33 Hz, 1 H), 8.16 (dd, J=7.33, 1.26 Hz, 1 H), 8.29 (d, J=8.34 Hz, 1 H), 8.69 (d, J=8.84 Hz, 1 H); ESI-MS: m/z 354.1 (M+H)$^+$.

Example 61

1-(2-Chlorophenylsulfonyl)-4-(5-chloropyridin-2-yl)piperazine

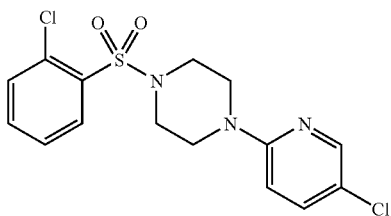

The title compound was prepared as described in the Scheme 1. $^1$H NMR (400 MHz, CHLOROFORM-D) δ ppm 3.24 (s, 1 H), 3.25 (d, J=5.05 Hz, 3 H), 3.53-3.58 (m, 4 H), 6.87 (d, J=9.09 Hz, 1 H), 7.57 (td, J=7.33, 2.02 Hz, 1 H), 7.61 (dd, J=9.09, 2.78 Hz, 1 H), 7.65-7.72 (m, 2 H), 7.99 (dd, J=7.96, 1.39 Hz, 1 H), 8.09 (d, J=2.78 Hz, 1 H); ESI-MS: m/z 373.2 (M+H)$^+$.

Example 62

1-(2-Chlorophenylsulfonyl)-4-(3-nitropyridin-2-yl)piperazine

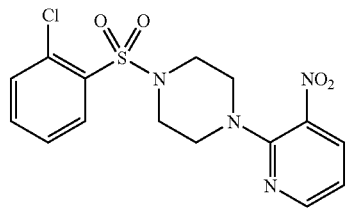

The title compound was prepared as described in the Scheme 1. $^1$H NMR (400 MHz, DMSO-D6) δ ppm 3.25-3.31 (m, 4 H), 3.36-3.44 (m, 4 H), 6.96 (ddd, J=8.08, 4.55, 1.26 Hz, 1H), 7.55-7.62 (m, 1 H), 7.66-7.75 (m, 2 H), 7.98 (d, J=7.83 Hz, 1 H), 8.26 (ddd, J=7.96, 1.64, 1.52 Hz, 1 H), 8.40 (td, J=3.03, 1.52 Hz, 1 H); ESI-MS: m/z 383.1 (M+H)$^+$.

Example 63

3-[4-(2-Chloro-benzenesulfonyl)-piperazin-1-yl]-pyridin-2-ol

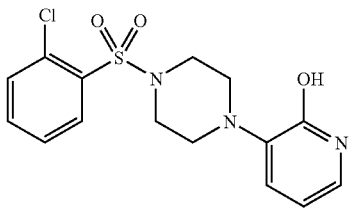

The title compound was prepared as described in the Scheme 1. ¹H NMR (400 MHz, CHLOROFORM-D) δ ppm 3.34-3.35 (m, 4 H) 3.52-3.63 (m, 4 H) 6.59 (d, J=7.58 Hz, 1 H) 7.19 (d, J=8.34 Hz, 1 H) 7.33 (t, J=7.96 Hz, 1 H) 7.39-7.47 (m, 1 H) 7.49-7.60 (m, 2 H) 8.10 (br, s, 2 H); ESI-MS: m/z 354.2 (M+H)+

Example 64

2-(4-(2-Chlorophenylsulfonyl)piperazin-1-yl)pyrimidine

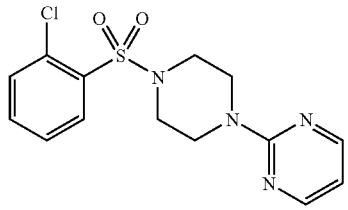

The title compound was prepared as described in the Scheme 1. ¹H NMR (400 MHz, DMSO-D6) δ ppm 3.21-3.27 (m, 4 H), 3.76-3.82 (m, 4 H), 6.63-6.67 (m, 1 H), 7.53-7.59 (m, 1 H), 7.64-7.71 (m, 2 H), 7.98 (d, J=7.83 Hz, 1 H), 8.35 (s, 1 H), 8.36 (d, J=1.01 Hz, 1 H); ESI-MS: m/z 339.1 (M+H)+.

Example 65

2-(4-(Naphthalen-1-ylsulfonyl)piperazin-1-yl)pyrimidine

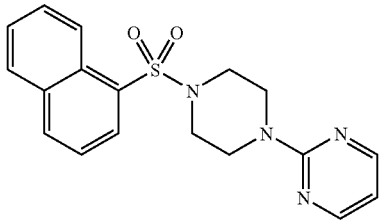

The title compound was prepared as described in the Scheme 1. ¹H NMR (400 MHz, DMSO-D6) δ ppm 3.12-3.18 (m, 4 H), 3.73-3.79 (m, 4 H), 6.60 (t, J=4.80 Hz, 1 H), 7.64-7.70 (m, 2 H), 7.73 (t, J=7.71 Hz, 1 H), 8.09 (d, J=8.34 Hz, 1 H), 8.15 (d, J=7.58 Hz, 1 H), 8.26-8.31 (m, 3 H), 8.67 (d, J=8.59 Hz, 1 H); ESI-MS: m/z 354.1 (M+H)+.

Example 66

2-(4-(Naphthalen-2-ylsulfonyl)piperazin-1-yl)pyrimidine

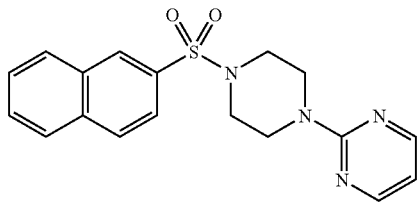

The title compound was prepared as described in the Scheme 1. ¹H NMR (400 MHz, DMSO-D6) δ ppm 2.99-3.05 (m, 4 H), 3.77-3.85 (m, 4 H), 6.59 (t, J=4.80 Hz, 1 H), 8.05 (d, J=7.58 Hz, 1 H), 8.15 (d, J=8.59 Hz, 1 H), 8.20 (d, J=7.83 Hz, 1 H), 8.29 (d, J=4.80 Hz, 2 H), 8.44 (s, 1 H); ESI-MS: m/z 354.1 (M+H)+.

Example 67

1-(2-Chlorophenylsulfonyl)-4-(5-nitrothiazol-2-yl)piperazine

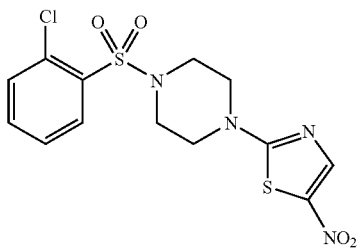

The title compound was prepared as described in the Scheme 1. ESI-MS: m/z 389.1 (M+H)+.

Example 68

2-(4-(2-chlorophenylsulfonyl)piperazin-1-yl)thiazole-4-carboxylic acid

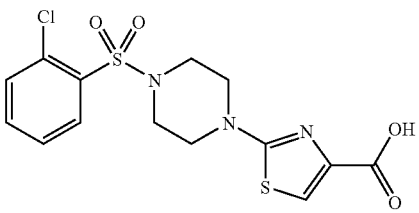

The title compound was prepared as described in the Scheme 1. ESI-MS: m/z 388.1 (M+H)+.

Example 69

2-(4-(2-Chlorophenylsulfonyl)piperazin-1-yl)thiazole-4-carboxamide

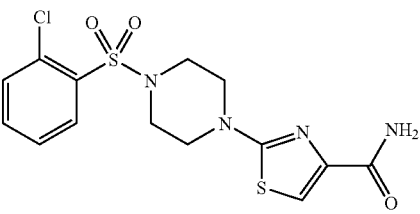

2-(4-(2-chlorophenylsulfonyl)piperazin-1-yl)thiazole-4-carboxylic acid (77 mg, 0.02 mmole), EDCI (39 mg, 0.02 mmole), HOBt (31 mg, 0.02 mmole) and ammonium formate (13 mg, 0.02 mmole) were combined in 1 ml of dry DMF. The mixture was treated with 1 equivalent of TEA and stirred at room temperature overnight. The title compound was obtained in yield of 37% after purification on preparative HPLC. ¹H NMR (400 MHz, CHLOROFORM-D) δ ppm 3.41 (s, 1 H), 3.42-3.44 (m, 3 H), 3.53-3.56 (m, 3 H), 3.57 (s, 1 H), 6.02 (s, 1 H), 6.95 (s, 1 H), 7.38-7.44 (m, 2 H), 7.50-7.53 (m, 2 H), 8.02-8.07 (m, 1 H); ESI-MS: m/z 387.1 (M+H)+.

Example 70

(2-(4-(2-Chlorophenylsulfonyl)piperazin-1-yl)thiazol-4-yl)methanol

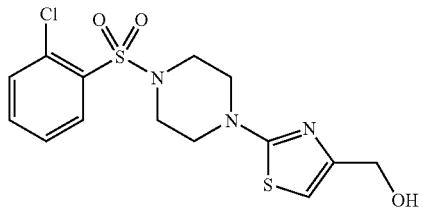

2-(4-(2-chlorophenylsulfonyl)piperazin-1-yl)thiazole-4-carboxylic acid (77 mg, 0.02 mmole) was dissolved in 1 mL of anhydrous THF under nitrogen protection. 0.4 mL of LiAlH$_4$ (1.0M solution in THF) was added to the solution through a syringe at −78° C. After 30 minutes, the reaction mixture was quenched with MeOH, evaporated to dryness, and extracted with EtOAc and 0.1 N tartaric acid solution in water. The organic layer was then dried over Na$_2$SO$_4$, and the solvent was removed. The title compound was obtained in 77% yield after purification using preparative HPLC. $^1$H NMR (400 MHz, DMSO-D6) δ ppm 3.33 (M, 4 H), 3.47 (dd, J=6.19, 3.92 Hz, 4 H), 4.31 (s, 2 H), 6.63 (s, 1 H), 7.54-7.62 (m, 1 H), 7.65-7.75 (m, 2 H), 7.95-8.02 (m, 1H); ESI-MS: m/z 374.1 (M+H)$^+$.

Example 71

1-(Naphthalen-1-ylsulfonyl)-4-(thiazol-2-yl)piperazine

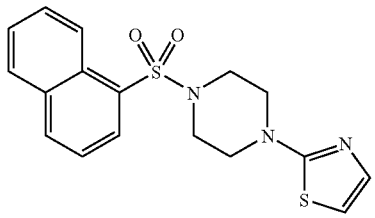

The title compound was prepared as described in the Scheme 1. $^1$H NMR (400 MHz, DMSO-D6) δ ppm 3.20-3.25 (m, 4 H), 3.38-3.44 (m, 4 H), 6.83 (d, J=3.54 Hz, 1 H), 7.11 (d, J=3.54 Hz, 1 H), 7.65-7.76 (m, 3 H), 8.11 (d, J=8.08 Hz, 1 H), 8.17 (d, J=7.33 Hz, 1 H), 8.30 (d, J=8.34 Hz, 1 H), 8.66 (d, J=8.59 Hz, 1 H); ESI-MS: m/z 360.1 (M+H)$^+$.

Example 72

1-(2-Chlorophenylsulfonyl)-4-1'-adamantylpiperazine

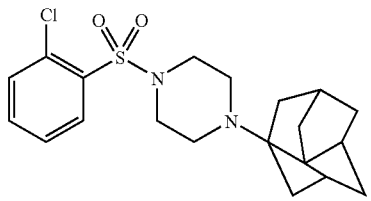

The title compound was prepared as described in the Scheme 1. $^1$H NMR (400 MHz, DMSO-D6) δ ppm 1.55 (s, 12H), 2.00 (s, 3 H), 2.58 (d, J=4.29 Hz, 4 H), 3.02-3.10 (m, 4 H), 7.53-7.60 (m, 1 H), 7.64-7.73 (m, 2 H), 7.90-7.96 (m, 1 H); ESI-MS: m/z 395.1 (M+H)$^+$.

Example 73 tert-Butyl 2-(4-(4-chlorophenylsulfonyl)-2-oxopiperazin-1-yl)acetate

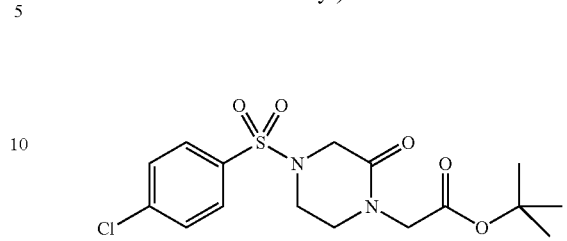

The title compound was prepared as described in the Scheme 1. $^1$H NMR (400 MHz, DMSO-D6) δ ppm 1.43 (s, 5 H), 3.35-3.39 (m, 1 H), 3.45-3.50 (m, 1 H), 3.75 (s, 1 H), 3.99 (s, 1H), 7.54 (d, J=8.34 Hz, 1 H), 7.72 (d, J=8.34 Hz, 1 H); ESI-MS: m/z 389.2 (M+H)$^+$.

Example 74

1-(2-Chlorophenylsulfonyl)-4-cyclopentylpiperazine

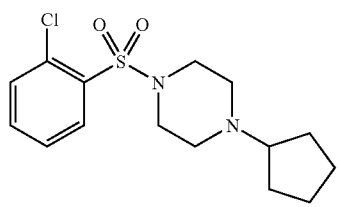

The title compound was prepared as described in the Scheme 1. $^1$H NMR (400 MHz, DMSO-D6) δ ppm 1.26 (s, 2 H), 1.45 (dd, J=7.71, 4.67 Hz, 2 H), 1.50-1.60 (m, 2 H), 1.71 (s, 2H), 2.42 (s, 5 H), 3.14 (s, 4 H), 7.54-7.59 (m, 1 H), 7.69 (td, J=8.15, 6.44 Hz, 2 H), 7.93-7.97 (m, 1 H); ESI-MS: m/z 329.1 (M+H)$^+$.

Example 75

1-(2-chlorophenylsulfonyl)-4-cyclohexylpiperazine

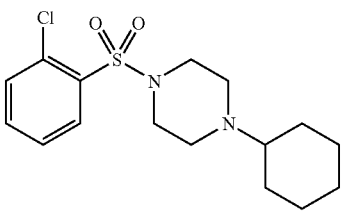

The title compound was prepared as described in the Scheme 1. $^1$H NMR (400 MHz, DMSO-D6) δ ppm 0.89-1.25 (m, 5 H), 1.51-1.52 (m, 1 H), 1.67 (broad s, 4 H), 2.20-2.22 (m, 1H), 2.98-3.20 (m, 4 H), 3.45 (m, 4 H), 7.47-7.61 (m, 1 H), 7.62-7.74 (m, 2 H), 7.94 (d, J=8.08 Hz, 1 H); ESI-MS: m/z 334 (m+H),$^+$

Example 76

1-Cyclopentyl-4-(naphthalen-1-ylsulfonyl)piperazine

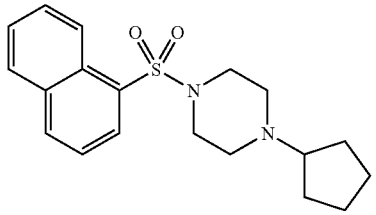

The title compound was prepared as described in the Scheme 1. ¹H NMR (400 MHz, DMSO-D6) δ ppm 1.12-1.23 (m, 2 H) 1.35-1.45 (m, 2 H) 1.50 (dt, J=7.77, 3.82 Hz, 2 H) 1.66 (d, J=6.82 Hz, 2 H) 2.33-2.43 (m, 5 H) 3.02 (s, 4 H) 7.65-7.75 (m, 3 H) 8.11 (dd, J=7.71, 3.66 Hz, 2 H) 8.30 (d, J=7.83 Hz, 1 H) 8.67 (d, J=8.59 Hz, 1 H); ESI-MS: m/z 345.2 (M+H)$^+$.

Example 77

8-(4-Cyclopentylpiperazin-1-ylsulfonyl)quinoline

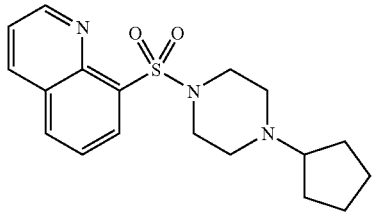

The title compound was prepared as described in the Scheme 1. ¹H NMR (400 MHz, DMSO-D6) δ ppm 1.20 (s, 2 H) 1.42 (s, 2 H) 1.52 (s, 2 H) 1.69 (s, 2 H) 2.38 (s, 4 H) 3.24 (s, 4 H) 7.69 (ddd, J=8.34, 4.04, 2.53 Hz, 1 H) 7.72-7.77 (m, 1 H) 8.30 (d, J=8.08 Hz, 1 H) 8.35 (d, J=7.58 Hz, 1 H) 8.50-8.56 (m, 1 H) 9.06 (ddd, J=4.17, 2.27, 2.15 Hz, 1 H); ESI-MS: m/z 346.2 (M+H)$^+$.

Example 78

1-Cyclopentyl-4-(4-methylnaphthalen-1-ylsulfonyl) piperazine

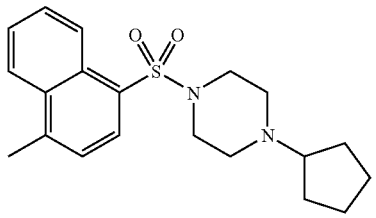

The title compound was prepared as described in the Scheme 1. ¹H NMR (400 MHz, DMSO-D6) δ ppm 1.16 (dd, J=11.75, 8.21 Hz, 2 H) 1.41 (dd, J=7.58, 4.80 Hz, 2 H) 1.45-1.54 (m, 2 H) 1.62-1.69 (m, 2 H) 2.33-2.41 (m, 5 H) 2.74 (s, 3 H) 2.97-3.03 (m, 4 H) 7.55 (d, J=7.83 Hz, 1 H) 7.68-7.74 (m, 2 H) 8.02 (d, J=7.58 Hz, 1 H) 8.16-8.20 (m, 1 H) 8.67-8.71 (m, 1 H); ESI-MS: m/z 359.2 (M+H)$^+$.

Example 79

5-(4-Cyclopentylpiperazin-1-ylsulfonyl)-N,N-dimethylnaphthalen-1-amine

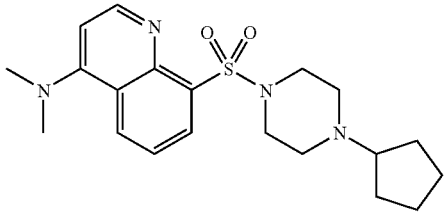

The title compound was prepared as described in the Scheme 1. ¹H NMR (400 MHz, DMSO-D6) δ ppm 1.18 (s, 2 H) 1.43 (s, 2 H) 1.51 (s, 2 H) 1.66 (s, 2 H) 2.37 (s, 4 H) 2.82 (s, 6 H) 3.02 (s, 3 H) 7.26 (d, J=7.33 Hz, 1 H) 7.57-7.62 (m, 1 H) 7.64-7.69 (m, 1 H) 8.11 (d, J=7.33 Hz, 1 H) 8.31 (d, J=8.84 Hz, 1 H) 8.52 (d, J=8.34 Hz, 1 H); ESI-MS: m/z 346.2 (M+H)$^+$.

Example 80

5-(4-Cyclopentylpiperazin-1-ylsulfonyl)Isoquinoline

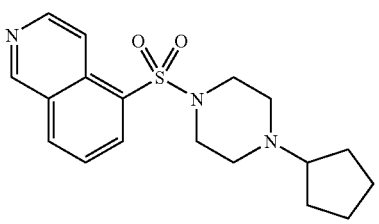

The title compound was prepared as described in the Scheme 1. ¹H NMR (400 MHz, DMSO-D6) δ ppm 1.18 (dd, J=11.62, 8.08 Hz, 2 H), 1.40-1.46 (m, 2 H), 1.48-1.54 (m, 2 H), 1.67 (s, 2 H), 2.39 (d, J=5.05 Hz, 5 H), 3.04 (s, 4 H), 7.89 (t, J=7.83 Hz, 1 H), 8.35 (d, J=6.82 Hz, 1 H), 8.45 (d, J=5.56 Hz, 1 H), 8.52 (d, J=8.08 Hz, 1 H), 8.70 (d, J=6.06 Hz, 1 H), 9.51 (s, 1 H); ESI-MS: m/z 346.2 (M+H)$^+$.

Example 81

1-(5-Chloronaphthalen-1-ylsulfonyl)-4-cyclopentylpiperazine

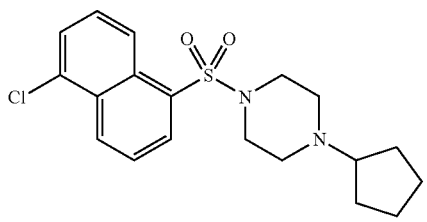

The title compound was prepared as described in the Scheme 1. $^1$H NMR (400 MHz, DMSO-D6) δ ppm 1.18-1.52 (m, 8 H) 2.37 (s, 4 H) 3.04 (s, 4 H) 3.47 (s, 1 H) 7.73 (t, J=8.08 Hz, 1 H) 7.90 (d, J=7.07 Hz, 2 H) 8.26 (s, 1 H) 8.60 (s, 1 H) 8.67 (d, J=8.84 Hz 1 H); ESI-MS: m/z 379.2 (M+H)$^+$.

Example 82

1-(2-Chlorophenylsulfonyl)piperazine

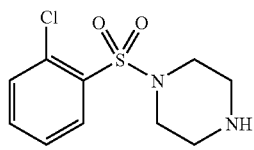

The title compound was prepared as described in the Scheme 1. $^1$H NMR (400 MHz, DMSO-D6) δ ppm 3.17 (d, J=5.05 Hz, 4 H), 3.32-3.42 (m, 4 H), 7.58-7.64 (m, 1 H), 7.70-7.77 (m, 2 H), 7.99 (dd, J=7.83, 1.52 Hz, 1 H), 8.86 (s, 2 H); ESI-MS: m/z 261.1 (M+H)$^+$.

Example 83

1-Benzyl-4-(2-chlorophenylsulfonyl)piperazin-2-one

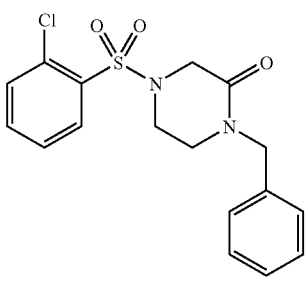

The title compound was prepared as described in the Scheme 1. ESI-MS: m/z 301.1 (M+H)$^+$.

Example 84

(R)-N-(1-Benzylpyrrolidin-3-yl)-2-chlorobenzenesulfonamide

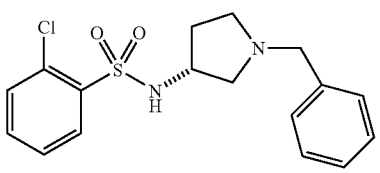

The title compound was prepared as described in the Scheme 1. ESI-MS: m/z 351.1 (M+H)$^+$.

Example 85

2-(2-Chlorophenylsulfonyl)-octahydropyrrolo[1,2-a]pyrazine

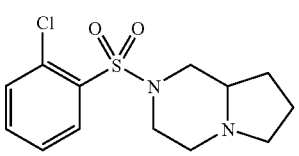

The title compound was prepared as described in the Scheme 1. $^1$H NMR (400 MHz, DMSO-D6) δ ppm 1.96 (s, 3 H), 3.07 (s, 3 H), 3.22 (s, 1 H), 3.38 (s, 3 H), 3.58 (s, 1 H), 3.94 (s, 1H), 4.13 (s, 1 H), 7.54-7.63 (m, 1 H), 7.69-7.76 (m, 2 H), 7.98-8.05 (m, 1 H); ESI-MS: m/z 301.1 (M+H)$^+$.

Example 86

2-(2-Chlorophenylsulfonyl)-octahydro-1H-pyrido[1,2-a]pyrazine

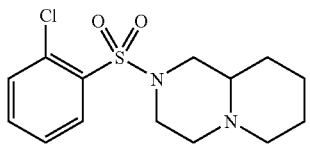

The title compound was prepared as described in the Scheme 1. $^1$H NMR (400 MHz, DMSO-D6) δ ppm 1.32-1.86 (m, 9 H), 2.76-3.87 (M, m, H), 7.58-7.64 (m, 1 H), 7.70-7.77 (m, 2 H), 7.98-8.02 (m, 1 H); ESI-MS: m/z 313.1 (M+H)$^+$.

Example 87

4-(4-(2-Chlorophenylsulfonyl)piperazin-1-yl)-1 H-indole

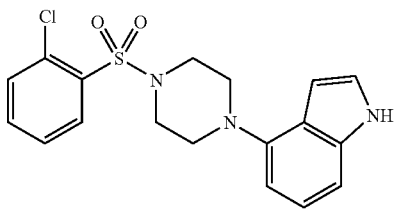

The title compound was prepared as described in the Scheme 1. ¹H NMR (400 MHz, DMSO-D6) δ ppm 3.14 (m, 4 H), 3.39 (m, 4 H), 6.37 (s, 1 H), 6.44 (d, J=7.07 Hz, 1 H), 6.95 (t, J=7.71 Hz, 1 H), 7.04 (d, J=8.08 Hz, 1 H), 7.22 (s, 1 H), 7.60 (s, 1 H), 7.67-7.76 (m, 2 H), 8.02 (d, J=7.58 Hz, 1 H); ESI-MS: m/z 376.1 (M+H)⁺.

Example 88

7-(4-(2-Chlorophenylsulfonyl)piperazin-1-yl)-1 H-indazole

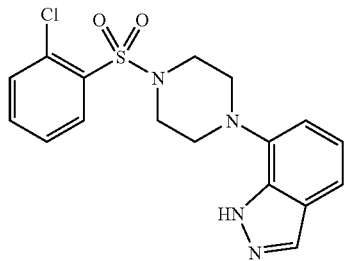

The title compound was prepared as described in the Scheme 2, step B. ¹H NMR (400 MHz, CHLOROFORM-D) δ ppm 3.27-3.38 (m, 4 H) 3.69-3.70-2.76 (m, 4 H) 7.00 (d, J=7.33 Hz, 1 H) 7.15 (t, J=7.83 Hz, 1 H) 7.38-7.47 (m, 1 H) 7.48-7.58 (m, 3 H) 8.06-8.15 (m, 2 H); ESI-MS: m/z 377.2 (M+H)⁺.

Example 89

4-(4-(2-Chlorophenylsulfonyl)piperazin-1-yl)-1 H-indazole

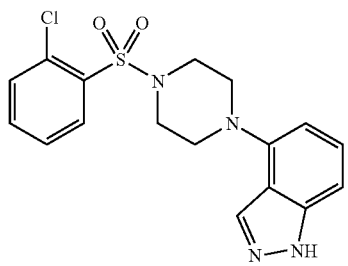

The title compound was prepared as described in the Scheme 2, step B. ¹H NMR (400 MHz, CHLOROFORM-D) δ ppm 3.22 (s, 3 H) 3.48 (s, 4 H) 6.48 (t, J=6.82 Hz, 1 H) 7.02 (d, J=7.33 Hz, 1 H) 7.17 (d, J=5.31 Hz, 1 H) 7.41 (t, J=7.58 Hz, 1 H) 7.47-7.57 (m, 2 H) 8.04 (d, J=8.08 Hz, 1 H); ESI-MS: m/z 377.2 (M+H)⁺.

Example 90

1-(1-(Naphthalen-1-ylsulfonyl)piperidin-4-yl)-1 H-benzo[d]imidazol-2(3 H)-one

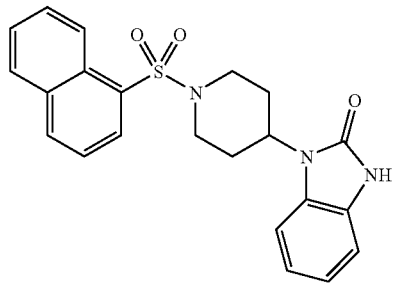

The title compound was prepared as described in the Scheme 1. ¹H NMR (400 MHz, DMSO-D6) δ ppm 1.64 (d, J=10.11 Hz, 2 H), 2.11 (td, J=12.63, 8.59 Hz, 2 H), 2.87 (t, J=11.87 Hz, 2 H), 3.96 (d, J=12.63 Hz, 2 H), 4.20-4.29 (m, 1 H), 6.50 (d, J=7.83 Hz, 1 H), 6.80-6.86 (m, 1 H), 6.92 (d, J=4.29 Hz, 2 H), 7.70-7.81 (m, 3 H), 8.19 (d, J=8.08 Hz, 1 H), 8.24 (d, J=7.33 Hz, 1 H), 8.36 (d, J=8.34 Hz, 1 H), 8.74 (d, J=8.34 Hz, 1 H), 10.81 (s, 1 H); ESI-MS: m/z 408.1 (M+H)⁺.

Example 91

1-(1-(2-Chlorophenylsulfonyl)piperidin-4-yl)piperidin-2-one

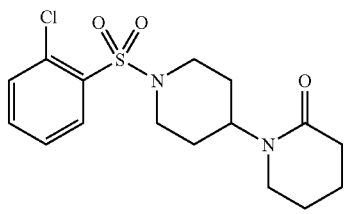

The title compound was prepared as described in the Scheme 1. ¹H NMR (400 MHz, DMSO-D6) δ ppm 1.55 (d, J=2.53 Hz, 2 H), 1.64 (td, J=12.19, 3.92 Hz, 6 H), 2.19 (t, J=6.57 Hz, 2 H), 2.80 (td, J=12.44, 2.40 Hz, 2 H), 3.08 (t, J=5.68 Hz, 2 H), 3.77 (d, J=12.63 Hz, 2 H), 4.30-4.39 (m, 1 H), 7.55 (td, J=7.45, 1.77 Hz, 1 H), 7.64-7.72 (m, 2 H), 7.97 (dd, J=7.71, 1.64 Hz, 1H); ESI-MS: m/z 357.1 (M+H)⁺.

Example 92

1-(2-chlorophenylsulfonyl)-4-(piperidin-1-yl)piperidine

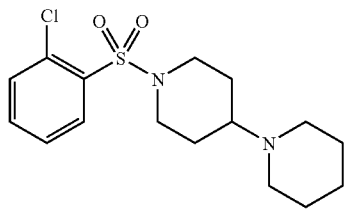

The title compound was prepared as described in the Scheme 1. $^1$H NMR (400 MHz, DMSO-D6) δ ppm 1.32-1.45 (m, 8 H) 1.71 (d, J=11.87 Hz, 2 H) 2.29-2.40 (m, 5 H) 2.68 (t, J=11.75 Hz, 2 H) 3.71 (d, J=12.38 Hz, 2 H) 7.52-7.60 (m, 1 H) 7.63-7.72 (m, 2 H) 7.95 (d, J=7.83 Hz, 1 H); ESI-MS: m/z 343 (m+H)$^+$.

Example 93

1-(2-chlorophenylsulfonyl)-4-phenyl-1,2,3,6-tetrahydropyridine

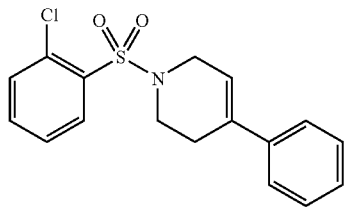

The title compound was prepared as described in the Scheme 1. $^1$H NMR (400 MHz, DMSO-D6) δ ppm 3.34 (broad and overlapped with water peak, 2 H) 3.50 (t, J=5.56 Hz, 2 H) 3.92 (broad s, 2 H) 6.15 (broad s, 1 H) 7.23-7.28 (m, 1 H) 7.30-7.36 (m, 2 H) 7.36-7.40 (m, 2H) 7.55-7.60 (m, 1 H) 7.64-7.71 (m, 2 H) 8.03 (d, J=7.83 Hz, 1 H); ESI-MS: m/z 334.2 (m+H)$^+$.

Example 94

1-(2-chlorophenylsulfonyl)-4-phenylpiperidine

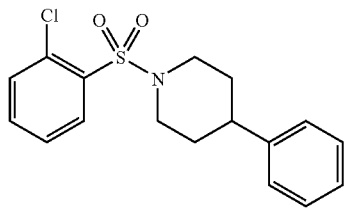

The title compound was prepared as described in the Scheme 1. $^1$H NMR (400 MHz, DMSO-D6) δ ppm 1.59 (qd, J=12.55, 4.04 Hz, 2 H) 1.81 (d, J=12.13 Hz, 2 H) 2.58-2.67 (m, 1H) 2.75-2.84 (m, 2 H) 3.82 (d, J=12.63 Hz, 2 H) 7.15-7.21 (m, 3 H) 7.26-7.30 (m, 2 H) 7.57 (t, J=7.45 Hz, 1 H) 7.65-7.74 (m, 2 H) 7.99 (d, J=8.08 Hz, 1 H); ESI-MS: m/z 336.2 (m+H)$^+$

Example 95

1-(2-Chlorophenylsulfonyl)-4-(pyrrolidin-1-yl)piperidine

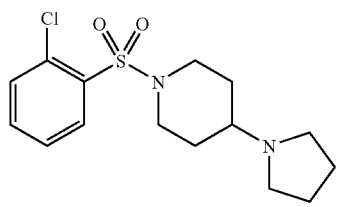

The title compound was prepared as described in the Scheme 1. $^1$H NMR (400 MHz, DMSO-D6) δ ppm 1.32-1.42 (m, 2 H) 1.63 (broad s, 4 H) 1.78-1.87 (m, 2 H) 2.03-2.12 (m, 1H) 2.42 (broad s, 4 H) 2.81-2.89 (m, 2 H) 3.53-3.61 (m, 2 H) 7.54-7.59 (m, 1 H) 7.64-7.72 (m, 2 H) 7.97 (dd, J=7.83, 1.52 Hz, 1 H); ESI-MS: m/z 329.1 (M+H)$^+$

Example 96

4-(1-(2-Chlorophenylsulfonyl)piperidin-4-yl)morpholine

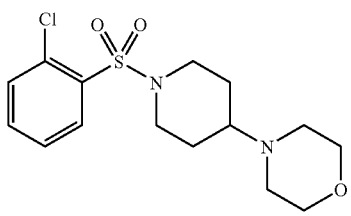

The title compound was prepared as described in the Scheme 1. ESI-MS: m/z 345.1 (M+H)$^+$.

Example 97

1-(2-Chlorophenylsulfonyl)-4-(2-methoxyphenyl)piperidine

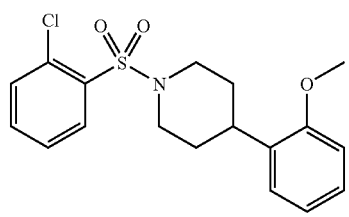

The title compound was prepared as described in the Scheme 1. $^1$H NMR (400 MHz, DMSO-D6) δ ppm 1.58 (qd, J=12.55, 4.04 Hz, 2 H), 1.73 (s, 2 H), 2.80 (td, J=12.44, 2.15 Hz, 2H), 2.91-3.00 (m, 1 H), 3.74 (s, 3 H), 3.79-3.86 (m, 2 H), 6.88 (t, J=7.45 Hz, 1 H), 6.93 (d, J=7.33 Hz, 1 H), 7.10 (dd, J=7.58, 1.77 Hz, 1 H), 7.15-7.21 (m, 1 H), 7.55-7.60 (m, 1 H), 7.66-7.74 (m, 2 H), 7.99 (dd, J=7.83, 1.52 Hz, 1 H); ESI-MS: m/z 366.1 (M+H)+.

Example 98

1-(2-Chlorophenylsulfonyl)-4-o-tolylpiperidine

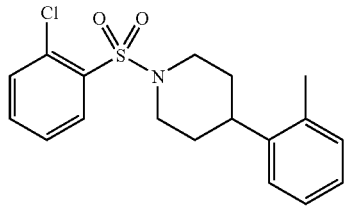

The title compound was prepared as described in the Scheme 1. ¹H NMR (400 MHz, DMSO-D6) δ ppm 1.60 (td, J=12.44, 3.92 Hz, 2 H), 1.73 (d, J=11.12 Hz, 2 H), 2.25 (s, 3 H), 2.78-2.88 (m, 3 H), 3.80-3.89 (m, 2 H), 7.04-7.15 (m, 4 H), 7.58 (td, J=7.45, 1.52 Hz, 1 H), 7.66-7.75 (m, 2 H), 8.00 (dd, J=7.71, 1.64 Hz, 1 H); ESI-MS: m/z 350.1 (M+H)+.

Example 99

Methyl 2-(1-(naphthalen-1-ylsulfonyl)piperidin-4-yl)benzoate

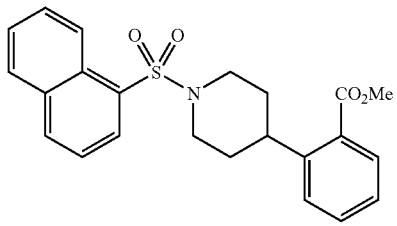

The title compound was prepared as described in the Scheme 1. ¹H NMR (400 MHz, DMSO-D6) δ ppm 1.65 (s, 2 H), 1.76 (s, 2 H), 2.56 (t, J=12.13 Hz, 2 H), 3.16 (s, 1 H), 3.73-3.76 (m, 3 H), 3.91 (d, J=11.62 Hz, 2 H), 7.27-7.35 (m, 2 H), 7.47-7.53 (m, 1 H), 7.65 (dd, J=7.83, 1.52 Hz, 1 H), 7.68-7.79 (m, 3 H), 8.10-8.20 (m, 2 H), 8.32 (d, J=8.08 Hz, 1 H), 8.74 (d, J=8.84 Hz, 1 H); ESI-MS: m/z 410.1 (M+H)+.

Example 100

(2-(1-(Naphthalen-1-ylsulfonyl)piperidin-4-yl)phenyl)methanol

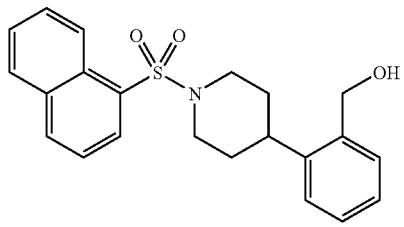

Methyl 2-(1-(naphthalen-1-ylsulfonyl)piperidin-4-yl)benzoate (80 mg, 0.02 mmol) was dissolved in 1 mL of anhydrous THF under nitrogen protection. 0.4 mL of LiAlH₄ (1.0M solution in THF) was added to the solution through a syringe at −78° C. After 30 minutes, the reaction mixture was quenched with MeOH, evaporated to dryness, and extracted with EtOAc and 0.1 N tartaric acid solution in water. The organic layer was then dried over Na₂SO₄, and the solvent was removed. The title compound was obtained in 60% yield after purification using preparative HPLC. ¹H NMR (400 MHz, DMSO-D6) δ ppm 1.58 (dd, J=12.38, 3.54 Hz, 2 H) 1.67-1.74 (m, 2 H) 2.52-2.61 (m, 2 H) 2.73-2.81 (m, 2 H) 3.88 (d, J=12.13 Hz, 2 H) 4.42 (d, J=3.79 Hz, 2 H) 4.96 (s, 1 H) 7.08-7.19 (m, 3 H) 7.24-7.29 (m, 1 H) 7.66-7.78 (m, 4 H) 8.13 (d, J=8.84 Hz, 1H) 8.17 (d, J=7.33 Hz, 1 H) 8.31 (d, J=8.08 Hz, 1 H) 8.75 (d, J=8.59 Hz, 1 H); ESI-MS: m/z 382.1 (M+H)+.

Example 101

(4aR,8aS)-2-(2-Chlorophenylsulfonyl)-decahydroisoquinoline

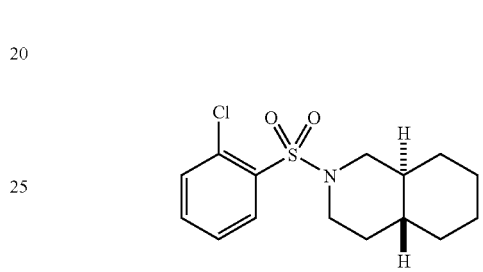

The title compound was prepared as described in the Scheme 1. ¹H NMR (400 MHz, DMSO-D6) δ ppm 0.86-0.97 (m, 2 H), 1.11-1.23 (m, 4 H), 1.48-1.59 (m, 4 H), 1.61-1.70 (m, 2 H), 2.32 (t, J=11.49 Hz, 1 H), 2.68 (td, J=12.51, 2.78 Hz, 1 H), 3.55 (ddd, J=12.19, 3.85, 1.64 Hz, 1 H), 3.72 (dt, J=12.44, 2.24 Hz, 1 H), 7.54 (td, J=7.58, 1.52 Hz, 1 H), 7.66 (ddd, J=17.81, 8.08, 1.39 Hz, 2 H), 7.95 (dd, J=7.83, 1.52 Hz, 1 H); ESI-MS: m/z 314.1 (M+H)+.

Example 102

3-(1-(2-Chlorophenylsulfonyl)piperidin-4-yl)-6-fluorobenzo[d]isoxazole

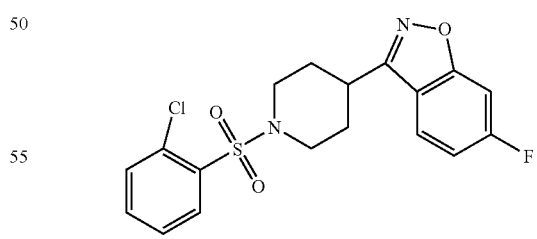

The title compound was prepared as described in the Scheme 1. ¹H NMR (400 MHz, DMSO-D6) δ ppm 1.71-1.82 (m, 2 H), 2.09-2.14 (m, 2 H), 2.96 (td, J=12.25, 2.53 Hz, 2 H), 3.32-3.40 (m, 1 H), 3.78-3.86 (m, 2 H), 7.28 (td, J=8.97, 2.27 Hz, 1 H), 7.59 (ddd, J=8.08, 7.33, 1.52 Hz, 1 H), 7.67-7.75 (m, 3 H), 7.94 (dd, J=8.72, 5.43 Hz, 1 H), 8.02 (dd, J=7.71, 1.39 Hz, 1H); ESI-MS: m/z 395.2 (M+H)+.

Example 103

1-(4-(Naphthalen-1-ylsulfonyl)piperazin-1-yl)butan-2-ol

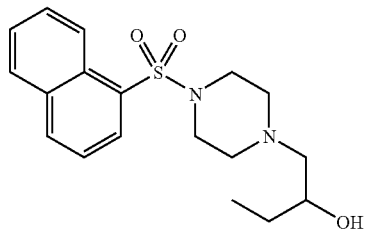

The title compound was prepared as described in the Scheme 4. $^1$H NMR (400 MHz, DMSO-D6) δ ppm 0.74-0.81 (m, 3 H) 1.12-1.20 (m, 1 H) 1.27-1.35 (m, 1 H) 2.14 (d, J=6.06 Hz, 2 H) 2.35-2.44 (m, 4 H) 3.03 (t, J=4.42 Hz, 4 H) 4.16 (d, J=3.79 Hz, 1 H) 7.65-7.75 (m, 3H) 8.12 (t, J=6.69 Hz, 2 H) 8.30 (d, J=8.08 Hz, 1 H) 8.67 (d, J=8.59 Hz, 1 H); ESI-MS: m/z 349.2 (M+H)$^+$.

Example 104

(R)-3-Methyl-2-(4-(naphthalen-1-ylsulfonyl)piperazin-1-yl)butan-1-ol

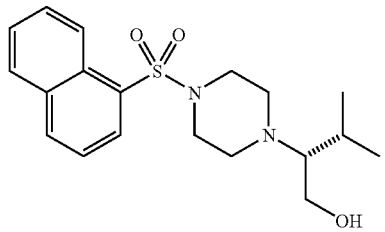

The title compound was prepared as described in the Scheme 4. $^1$H NMR (400 MHz, DMSO-D6) δ ppm 0.77-0.86 (m, 6 H) 1.54 (m, 1 H) 2.98-3.48 (m, 12H) 7.67-7.78 (m, 3 H) 8.11-8.19 (m, 2 H) 8.35 (d, J=8.34 Hz, 1 H) 8.66 (d, J=8.34 Hz, 1 H); ESI-MS: m/z 362.2 (M+H)$^+$.

Example 105

(S)-3-Methyl-2-(4-(naphthalen-1-ylsulfonyl)piperazin-1-yl)butan-1-ol

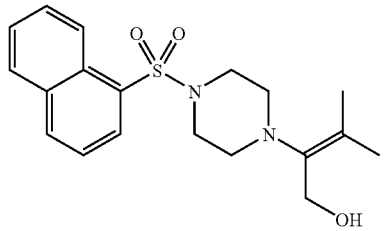

The title compound was prepared as described in the Scheme 4. $^1$H NMR (400 MHz, DMSO-D6) δ ppm 0.77-0.86 (m, 6 H) 1.54 (m, 1 H) 2.98-3.48 (m, 12H) 7.67-7.78 (m, 3 H) 8.11-8.19 (m, 2 H) 8.35 (d, J=8.34 Hz, 1 H) 8.66 (d, J=8.34 Hz, 1 H); ESI-MS: m/z 362.2 (M+H)$^+$.

Example 106

Methyl 2-methyl-2-(4-(naphthalen-1-ylsulfonyl)piperazin-1-yl)propanoate

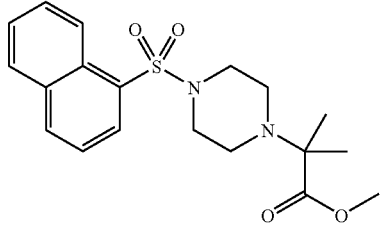

The title compound was prepared as described in the Scheme 4. $^1$H NMR (400 MHz, DMSO-D6) δ ppm 1.24-1.34 (m, 5 H) 2.94 (s, 2 H) 3.12 (s, 2 H) 3.64 (s, 2 H) 7.67-7.78 (m, 3H) 8.12-8.18 (m, 2 H) 8.35 (d, J=8.34 Hz, 1 H) 8.71 (d, J=8.59 Hz, 1 H); ESI-MS: m/z 377.2 (M+H)$^+$.

Example 107

(R)-4-Methyl-2-(4-(naphthalen-1-ylsulfonyl)piperazin-1-yl)pentan-1-ol

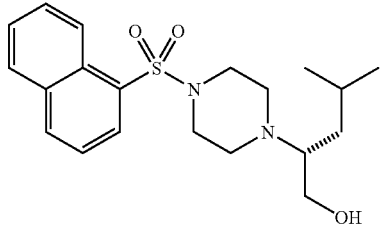

The title compound was prepared as described in the Scheme 4. $^1$H NMR (400 MHz, DMSO-D6) δ ppm 0.77-0.88 (m, 6 H) 1.05 (ddd, J=13.33, 8.91, 4.04 Hz, 1 H) 1.21 (s, 1 H) 1.62-1.74 (m, 1 H) 2.98 (s, 2 H) 3.60 (m, 4 H) 3.75 (m, 4 H) 7.67-7.78 (m, 3 H) 8.15 (t, J=7.07 Hz, 2 H) 8.34 (s, 1 H) 8.66 (d, J=8.84 Hz, 1 H); ESI-MS: m/z 377.2 (M+H)$^+$.

Example 108

(R)-2-(4-(Naphthalen-1-ylsulfonyl)piperazin-1-yl)pentan-1-ol

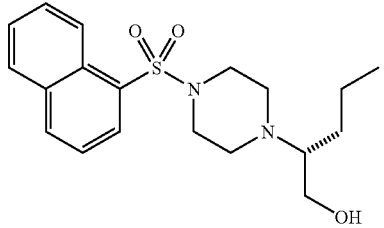

The title compound was prepared as described in the Scheme 4. $^1$H NMR (400 MHz, DMSO-D6) δ ppm 0.83 (t, J=6.95 Hz, 3 H) 1.20-1.30 (m, 2 H) 1.35 (m, 2 H) 2.87 (s, 1 H) 3.07 (m, 2 H) 3.49 (s, 4 H) 3.74 (s, 4 H) 7.68-7.78 (m, 3 H) 8.11-8.19 (m, 2 H) 8.36 (d, J=8.34 Hz, 1H) 8.67 (t, J=9.47 Hz, 1 H); ESI-MS: m/z 362.2 (M+H)$^+$.

Example 109

(1-(4-(Naphthalen-1-ylsulfonyl)piperazin-1-yl)cyclopentyl)methanol

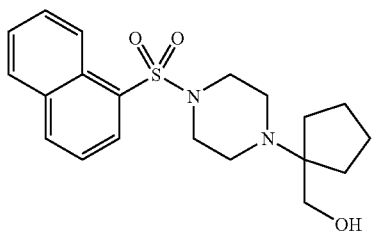

The title compound was prepared as described in the Scheme 4. ESI-MS: m/z 375.2 (M+H)⁺.

Example 110

(R)-2-(4-(Naphthalen-1-ylsulfonyl)piperazin-1-yl)-3-phenylpropan-1-ol

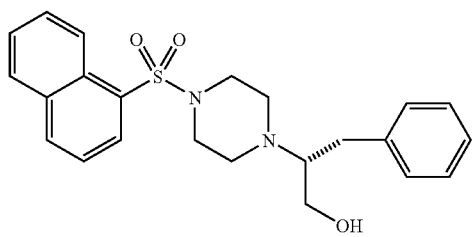

The title compound was prepared as described in the Scheme 4. $^1$H NMR (400 MHz, DMSO-D6) δ ppm 2.77 (m, 2 H) 2.91 (m, 1 H) 3.08 (s, 2 H) 3.34-3.44 (m, 4 H) 3.48 (s, 5 H) 7.22-7.33 (m, 6 H) 7.69-7.80 (m, 2 H) 8.13-8.21 (m, 1 H) 8.68-8.72 (d, 2 H); ESI-MS: m/z 411.2 (M+H)⁺.

Example 111

(R)-2-(4-(Naphthalen-1-ylsulfonyl)piperazin-1-yl)-2-phenylethanol

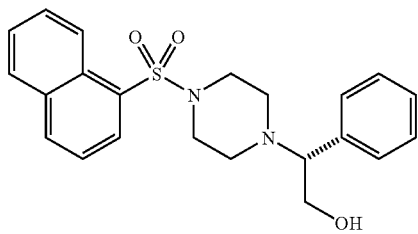

The title compound was prepared as described in the Scheme 4. $^1$H NMR (400 MHz, DMSO-D6) δ ppm 3.20 (s, 2 H) 3.47 (s, 5 H) 4.94 (s, 4 H) 7.33 (s, 5 H) 7.73 (s, 3 H) 8.17 (s, 2 H) 8.36 (s, 1 H) 8.64 (s, 1 H); ESI-MS: m/z 397.2 (M+H)⁺.

Example 112

(R)-1-(4-(Naphthalen-1-ylsulfonyl)piperazin-1-yl)propan-2-ol

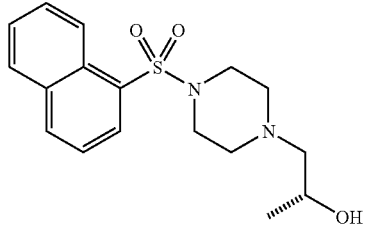

The title compound was prepared as described in the Scheme 4. $^1$H NMR (400 MHz, DMSO-D6) δ ppm 1.04 (d, J=6.32 Hz, 3 H) 2.83 (s, 1 H) 2.89-2.99 (m, 2 H) 3.07 (m, 4 H) 3.49-3.83 (m, 2 H) 3.97 (d, J=6.57 Hz, 1 H) 7.69-7.78 (m, 3 H) 8.13-8.20 (m, 2 H) 8.37 (d, J=8.34 Hz, 1 H) 8.66 (d, J=8.08 Hz, 1 H); ESI-MS: m/z 335.2 (M+H)⁺.

Example 113

(S)-1-(4-(Naphthalen-1-ylsulfonyl)piperazin-1-yl)propan-2-ol

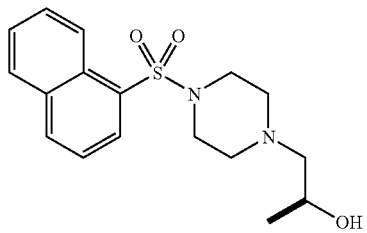

The title compound was prepared as described in the Scheme 4. $^1$H NMR (400 MHz, DMSO-D6) δ ppm 1.04 (d, J=6.32 Hz, 3 H) 2.83 (s, 1 H) 2.89-2.99 (m, 2 H) 3.07 (m, 4 H) 3.49-3.83 (m, 2 H) 3.97 (d, J=6.57 Hz, 1 H) 7.69-7.78 (m, 3 H) 8.13-8.20 (m, 2 H) 8.37 (d, J=8.34 Hz, 1 H) 8.66 (d, J=8.08 Hz, 1 H); ESI-MS: m/z 335.2 (M+H)⁺.

Example 114

Trans-2-(4-(2-chlorophenylsulfonyl)piperazin-1-yl)cyclopentanol

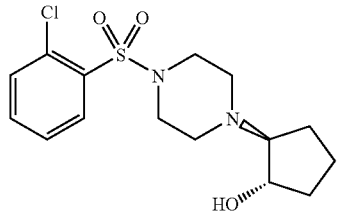

1-(2-Chlorophenylsulfonyl)piperizine (1 eq, 0.19 mmol) was dissolved in ethyl alcohol (2 ml), then treated with 6-oxabicyclo[3,1,0]hexane (2eq, 0.38 mmol), the reaction solution was heated to 80° C. for 8 hour. The reaction mixture was purified by prep-HPLC. $^1$H NMR (400 MHz, CHLOROFORM-D) δ ppm 1.36-1.48 (m, 1 H), 1.49-1.74 (m, 3 H), 1.81-2.03 (m, 2 H), 2.52-2.67 (m, 3 H), 2.68-2.78 (m, 2 H), 3.28-3.37 (m, 4 H), 3.99-4.18 (m, 1 H), 7.33-7.42 (m, 1 H), 7.44-7.58 (m, 2 H), 7.98 (d, J=8.21, 1.14 Hz, 1 H); ESI-MS: m/z 345 (m+H)+.

Example 115

Trans-2-(4-(2-chlorophenylsulfonyl)piperazin-1-yl)cyclohexanol

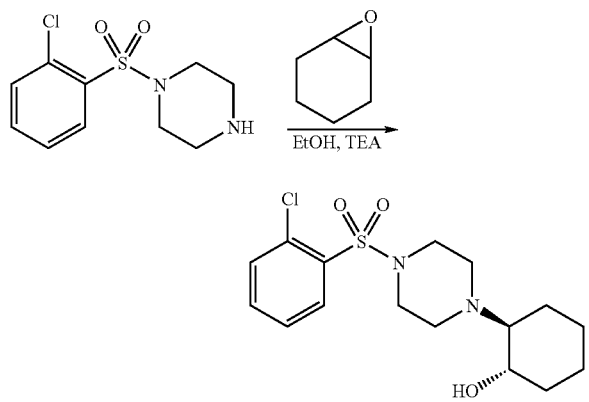

The title compound was prepared by a process analogous to that described for Example 114. ¹H NMR (400 MHz, CHLOROFORM-D) δ ppm 1.14-1.33 (m, 3 H), 1.66-1.94 (m, 3 H), 2.07-2.32 (m, 2 H), 2.41-2.59 (m, 2 H), 2.72-2.90 (m, 2 H), 3.25-3.46 (m, 5 H), 3.58-3.74 (m, 1 H), 7.36-7.43 (m, 1 H), 7.45-7.64 (m, 2 H), 8.03 (dd, J=7.83, 1.52 Hz, 1 H); ESI-MS: m/z 359 (m+H)+.

Example 116

4-(4-cyclopentylpiperazin-1-ylsulfonyl)isoquinolin-1-ol

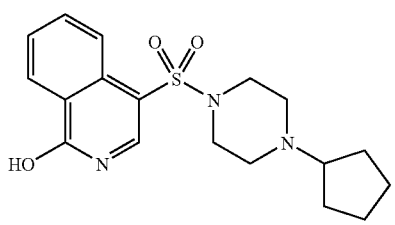

Isoquinolin-1-ol (10 mmole) was treated with sulfurochloridic acid at 80° C. over night. ¹H NMR (400 MHz, DMSO-D6) δ ppm 1.50-1.66 (m, 6 H), 1.89-1.97 (m, 2 H), 2.83-2.92 (m, 2H), 2.99-3.09 (m, 2 H), 3.48-3.58 (m, 3 H), 3.80-3.90 (m, 2 H), 7.65 (t, J=7.58 Hz, 1 H), 7.84-7.91 (m, 2 H), 8.16 (d, J=8.34 Hz, 1 H), 8.29 (d, J=8.08 Hz, 1 H), 9.37 (s, 1 H), 12.21 (d, J=5.05 Hz, 1 H); ESI-MS: m/z 362 (m+H)+.

Example 117

Methyl 1-(naphthalen-1-ylsulfonyl)piperidine-4-carboxylate

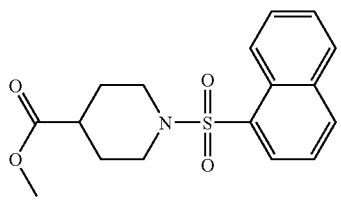

Methyl isonipecotate (1.0 g, 6.9 mmol), 1-naphthalenesulfonyl chloride (1.58 g, 6.9 mmol) and DMAP (0.17 g, 1.4 mmol) were dissolved in pyridine (10 mL). After stirring overnight, the reaction mixture was concentrated in vacuo, diluted with water (15 mL) and extracted into methylene chloride (3×10 mL). The combined organic extracts were dried over anhydrous sodium sulfate and concentrated in vacuo. The resulting yellow oil was purified by column chromatography on SiO₂ eluted with hexanes/ethyl acetate (1:1) to yield 1.7 g (73%) of the title compound as a white foam. ¹H NMR (400 MHz, Chloroform-d) δ, ppm: 1.67-1.77 (m, 2 H), 1.93 (dd, J=13.64, 3.79 Hz, 2 H), 2.25-2.34 (m, 1 H), 2.68-2.77 (m, 2 H), 3.63 (s, 3 H), 3.74 (ddd, J=12.51, 3.66, 3.54 Hz, 2 H), 7.56-7.66 (m, 3 H), 7.92 (d, J=9.35 Hz, 1 H), 8.07 (d, J=8.34 Hz, 1 H), 8.21 (d, J=7.33 Hz, 1 H), 8.71 (d, J=8.08 Hz, 1 H); ESI-MS: m/z 334.3 (M+H)+.

Example 118

2-(1-(Naphthalen-1-ylsulfonyl)piperidin-4-yl)propan-2-ol

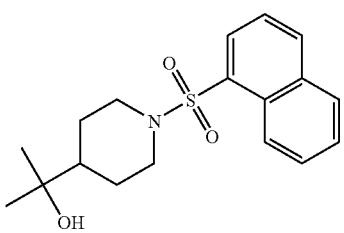

Commercially available methylmagnesium bromide (0.300 mL, 3.0M in Et₂O 0.90 mmol) was added dropwise to a stirring solution of methyl 1-(naphthalen-1-ylsulfonyl)piperidine-4-carboxylate (0.100 g, 0.30 mmol) in tetrahydrofuran (5 mL) and allowed to stir for 1 h. The reaction mixture was quenched by addition to a cold solution of saturated ammonium chloride (3 mL). The resulting solution was extracted with ethyl acetate (2×3 mL). The combined organic fractions were dried over anhydrous sodium sulfate and concentrated in vacuo. The resulting residue was purified by column chromatography on SiO₂ eluted with hexanes/ethyl acetate (1:1) to yield 0.060 g (60%) of the title compound as a white foam. ¹H NMR (400 MHz, Chloroform-d) δ, ppm: 1.09 (s, 6 H), 1.32 (qd, J=12.38, 4.04 Hz, 3 H), 1.76 (d, J=12.88 Hz, 2 H), 2.47 (t, J=12.25 Hz, 2 H), 3.95 (d, J=12.13 Hz, 2 H), 7.54-7.66 (m, 3 H), 7.92 (d, J=8.84 Hz, 1 H), 8.06 (d, J=8.08 Hz, 1 H), 8.20 (d, J=6.32 Hz, 1 H), 8.77 (d, J=8.34 Hz, 1 H); ESI-MS: m/z 334.3 (M+H)⁺.

Example 119

1-(1-(Naphthalen-1-ylsulfonyl)piperidin-4-yl)cyclopropanol

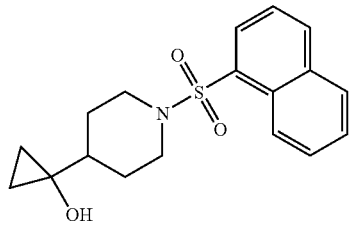

Ethylmagnesium bromide (0.110 mL, 3.0 M in THF, 0.330 mmol) was added dropwise to a stirring solution of methyl 1-(naphthalen-1-ylsulfonyl)piperidine-4-carboxylate (0.100 g, 0.30 mmol) and methyltitanium triisopropoxide (0.300 mL, 1.0 M in THF, 0.300 mmol) in tetrahydrofuran (3 mL) at 0° C. The reaction mixture was allowed to warm to ambient temperature over 2 h then quenched with water (15 mL). The resulting flocculent solution was diluted with ethyl acetate (15 mL) and filtered through Celite. The filtrate was extracted with ethyl acetate (2×10 mL). The combined organic extracts were dried over anhydrous sodium sulfate and concentrated in vacuo. The resulting residue was purified by column chromatography on SiO₂ eluted with hexanes/ethyl acetate (1:1) to yield 0.035 g (35%) of the title compound as a white foam. ¹H NMR (400 MHz, Chloroform-d) δ, ppm: 0.36-0.41 (m, 2 H), 0.67-0.71 (m, 2H), 0.90-0.98 (m, 1 H), 1.72 (dd, J=13.89, 1.26 Hz, 2 H), 2.49 (td, J=12.51, 2.53 Hz, 2 H), 3.91-4.02 (m, 2 H), 7.54-7.60 (m, 3 H), 7.92 (d, J=8.34 Hz, 1 H), 8.06 (d, J=8.08 Hz, 1 H), 8.21 (d, J=7.33 Hz, 1 H), 8.76 (s, 1 H); ESI-MS: m/z 332.3 (M+H)⁺.

Example 120

1-(4-(Naphthalen-1-ylsulfonyl)piperazin-1-yl)ethanone

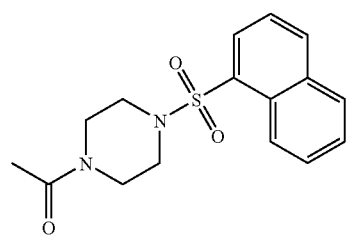

1-Acetylpiperazine (0.500 g, 3.9 mmol), 1-naphthalenesulfonyl chloride (0.884 g, 3.9 mmol) and DMAP (0.095 g, 0.70 mmol) were dissolved in pyridine (6 mL). After stirring overnight, the reaction mixture was concentrated in vacuo, and quenched with an ice cold solution of 1.0 M HCl (15 mL). The resulting precipitate was filtered and rinsed with water. Trituration with ether followed by filtration provided the 1.06 g (85%) of the title compound as a white solid. ¹H NMR (400 MHz, Chloroform-d) δ, ppm: 2.00 (s, 3 H), 3.12-3.21 (m, 4 H), 3.45-3.54 (m, 2 H), 3.57-3.67 (m, 2 H), 7.56-7.67 (m, 3 H), 7.94 (d, J=7.58 Hz, 1 H), 8.10 (d, J=8.08 Hz, 1 H), 8.20 (d, J=7.58 Hz, 1 H), 8.73 (d, J=9.09 Hz, 1 H); ESI-MS: m/z 319.4 (M+H)⁺.

Example 121

1-(1-Methylcyclopropyl)-4-(naphthalen-1-ylsulfonyl)piperazine

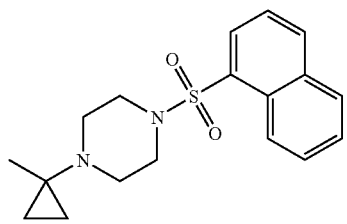

The title compound was prepared from commercially available ethylmagnesium bromide 1-(4-(naphthalen-1-ylsulfonyl)piperazin-1-yl)ethanone and methyltitanium triisopropoxide according to the procedure described in Scheme 5. ¹H NMR (400 MHz, Chloroform-d) δ, ppm: 0.24-0.30 (m, 2 H), 0.36-0.41 (m, 2 H), 0.98 (s, 3 H), 2.64 (t, J=4.93 Hz, 4 H), 3.10 (s, 4 H), 7.53-7.59 (m, 3 H), 7.91 (d, J=8.34 Hz, 1 H) 8.05 (d, J=7.83 Hz, 1 H), 8.17 (d, J=7.33 Hz, 1H), 8.80 (s, 1 H); ESI-MS: m/z 331.4 (M+H)⁺.

Example 122

1-(2-Chlorophenylsulfonyl)-4-(1-methylcyclopropyl)piperazine

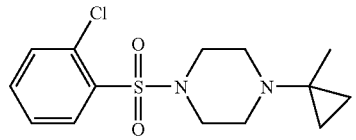

The title compound was prepared as described in the Scheme 5. ¹H NMR (400 MHz, DMSO-D6) δ ppm 0.26-0.31 (m, 2 H), 0.38-0.43 (m, 2 H), 0.96 (s, 3 H), 2.53-2.59 (m, 4 H), 3.08 (m, 4 H), 7.53-7.58 (m, 1 H), 7.65-7.73 (m, 2 H), 7.92-7.97 (m, 1 H); ESI-MS: m/z 315.3 (M+H)⁺.

Example 123

1-(3-Chloro-2-methylphenylsulfonyl)-4-(1-methylcyclopropyl)piperazine

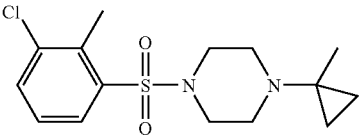

The title compound was prepared as described in the Scheme 5. ¹H NMR (400 MHz, DMSO-D6) δ ppm 0.27-0.32

(m, 2 H), 0.36-0.42 (m, 2 H), 0.98 (s, 3 H), 2.56-2.59 (m, 4 H), 2.59 (s, 3 H), 2.93-3.05 (m, 4 H), 7.44 (t, J=8.08 Hz, 1 H), 7.78 (dd, J=7.96, 1.39 Hz, 2 H); ESI-MS: m/z 329.3 (M+H)+.

Example 124

1-(2-Chloro-6-methylphenylsulfonyl-4-(1-methylcyclopropyl)piperazine

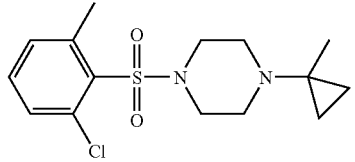

The title compound was prepared as described in the Scheme 5. ¹H NMR (400 MHz, DMSO-D6) δ ppm 0.28-0.32 (m, 2 H), 0.41-0.45 (m, 2 H), 0.96 (s, 3 H), 2.52-2.57 (m, 4 H), 2.62 (s, 3 H), 3.06-3.14 (m, 4 H), 7.39 (m, 1 H), 7.49 (t, J=7.58 Hz, 1 H), 7.51-7.54 (m, 1 H); ESI-MS: m/z 329.3 (M+H)+.

Example 125

1-(2-Chloro-4-fluorophenylsulfonyl)-4-(1-methylcyclopropyl)piperazine

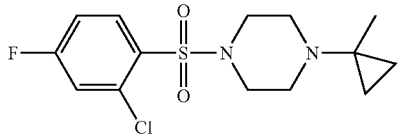

The title compound was prepared as described in the Scheme 5. ¹H NMR (400 MHz, DMSO-D6) δ ppm 0.30 (m, 2 H), 0.38-0.43 (m, 2 H), 0.97 (s, 3 H), 2.54-2.60 (m, 4 H), 3.03-3.12 (m, 4 H), 7.44 (ddd, J=8.97, 7.96, 2.78 Hz, 1 H), 7.75 (dd, J=8.84, 2.53 Hz, 1 H), 8.00 (dd, J=8.97, 5.94 Hz, 1 H); ESI-MS: m/z 333.2 (M+H)+.

Example 126

1-(4-Bromo-2-chlorophenylsulfonyl)-4-(1-methylcyclopropyl)piperazine

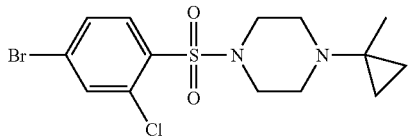

The title compound was prepared as described in the Scheme 5. ¹H NMR (400 MHz, DMSO-D6) δ ppm 0.27-0.32 (m, 2 H), 0.39-0.43 (m, 2 H), 0.97 (s, 3 H), 2.56 (t, J=4.80 Hz, 4H), 3.08 (m, 4 H), 7.75-7.79 (m, 1 H), 7.82-7.85 (m, 1 H), 8.02 (d, J=1.77 Hz, 1 H); ESI-MS: m/z 393.2 (M+H)+ (⁷⁹Br).

Example 127

1-(1-Methylcyclopropyl)-4-(2-(trifluoromethyl)phenylsulfonyl)piperazine

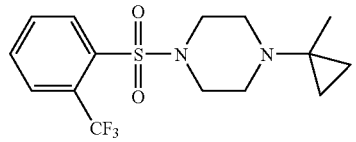

1-(1-Methylcyclopropyl)piperazine (TFA salt) (50.9 mg, 0.200 mmol) was dissolved in dichloromethane (1.0 mL) and NEt₃ (0.3 mL) was added. To this mixture, 2-trifluoromethylbenzenesulfonyl chloride (73.4 mg, 0.300 mmol) was added and the reaction mixture was stirred at room temperature for 1 h. The solvent was evaporated in vacuo and the resulting crude mixture was purified by HPLC (25-40% acetonitrile in water (0.05 TFA buffer). The product containing fractions were concentrated in vacuo until only water was left, basified with NaHCO₃ (sat. aq., 20 mL) and extracted with dichloromethane (3×7 mL). The combined organic extracts were dried (MgSO₄), filtered and concentrated in vacuo to afford the title compound as a white solid (56.6 mg, 81%). ¹H NMR (400 MHz, DMSO-D6) δ ppm 0.28-0.32 (m, 2 H), 0.39-0.44 (m, 2 H), 0.98 (s, 3 H), 2.59 (t, J=4.80 Hz, 4 H), 3.08 (m, 4 H), 7.84-7.93 (m, 2 H), 7.99-8.04 (m, 2 H); ESI-MS: m/z 349.3 (M+H)+.

Example 128

3-Chloro-4-(4-(1-methylcyclopropyl)piperazin-1-ylsulfonyl)benzonitrile

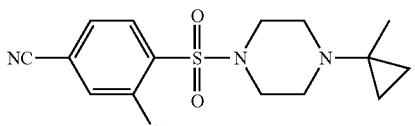

The title compound was prepared as described in the Scheme 5. ¹H NMR (400 MHz, DMSO-D6) δ ppm 0.27-0.32 (m, 2 H) 0.39-0.43 (m, 2 H), 0.97 (s, 3 H), 2.54-2.59 (m, 4 H), 3.09-3.17 (m, 4 H), 8.02 (dd, J=8.32, 1.52 Hz, 1 H), 8.07 (d, J=8.32 Hz, 1 H), 8.33 (d, J=1.52 Hz, 1 H); ESI-MS: m/z 340.2 (M+H)+.

Example 129

1-(4-Bromo-2-methylphenylsulfonyl)-4-(1-methyl-cyclopropyl)piperazine

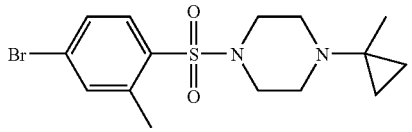

The title compound was prepared as described in the Sclheme 5. $^1$H NMR (400 MHz, DMSO-D6) δ ppm 0.25-0.31 (m, 2 H), 0.36-0.42 (m, 2 H), 0.97 (s, 3 H), 2.53 (s, 3 H), 2.57 (t, J=4.93 Hz, 4 H), 2.88-3.01 (m, 4 H), 7.63 (dd, J=8.60, 2.02 Hz, 1 H), 7.66 (d, J=8.60 Hz, 1 H), 7.73 (d, J=2.02 Hz, 1 H); ESI-MS: m/z 373.2 (M+H)$^+$ ($^{79}$Br).

Example 130

1-(4-Bromo-2-(trifluoromethyl)phenylsulfonyl)-4-(1-methylcyclopropyl) piperazine

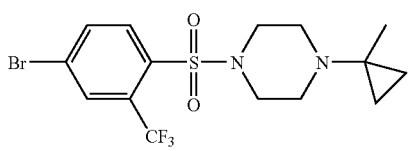

The title compound was prepared as described in the Scheme 5. $^1$H NMR (400 MHz, DMSO-D6) δ ppm 0.28-0.33 (m, 2 H), 0.38-0.43 (m, 2 H), 0.98 (s, 3 H), 2.59 (t, J=4.80 Hz, 4H), 3.08 (m, 4 H), 7.92 (d, J=8.34 Hz, 1 H), 8.12 (dd, J=8.59, 2.02 Hz, 1 H), 8.18 (d, J=1.77 Hz, 1 H); ESI-MS: m/z 427.2 (M+H)$^+$ ($^{79}$Br).

Example 131

1-(Benzo[b]thiophen-3-ylsulfonyl)-4-(1-methylcyclopropyl)piperazine

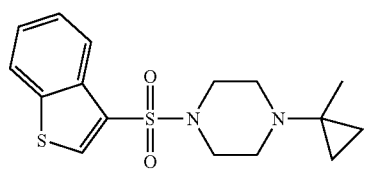

The title compound was prepared as described in the Scheme 5. $^1$H NMR (400 MHz, DMSO-D6) δ ppm 0.21-0.25 (m, 2 H), 0.30-0.36 (m, 2 H), 0.93 (s, 3 H), 2.56 (t, J=4.80 Hz, 4H), 2.93 (m, 4 H), 7.48-7.56 (m, 2 H), 8.13-8.18 (m, 2 H), 8.56 (s, 1 H); ESI-MS: m/z 337.3 (M+H)$^+$.

Example 132

5-(4-(1-Methylcyclopropyl)piperazin-1-ylsulfonyl) Isoquinoline

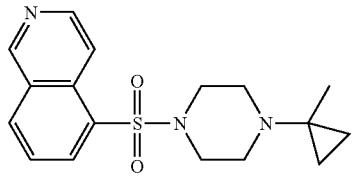

The title compound was prepared as described in the Scheme 5. $^1$H NMR (400 MHz, DMSO-D6) δ ppm 0.50-0.74 (m, 2 H), 0.75-1.03 (m, 2 H), 1.22 (s, 3 H), 2.57-2.94 (m, 2 H), 2.99-3.49 (m, 4 H), 3.52-4.19 (m, 2 H), 7.93 (t, J=7.83 Hz, 1 H), 8.40 (d, J=7.33 Hz, 1 H), 8.49 (d, J=6.32 Hz, 1 H), 8.57 (d, J=8.34 Hz, 1 H), 8.72 (d, J=5.81 Hz, 1 H), 9.54 (s, 1 H); ESI-MS: m/z 332.3 (M+H)$^+$.

Example 133

1-(Cyclopropylsulfonyl)-4-(1-methylcyclopropyl) piperazine

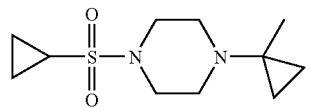

The title compound was prepared ad described in the Scheme 5, except that the desired product was obtained as a TFA salt by lyophilization. $^1$H NMR (400 MHz, DMSO-D6) δ ppm 0.54-0.83 (m, 2 H), 0.87-1.11 (m, 6 H), 1.26 (br s, 3 H), 2.64-2.77 (m, 1 H), 2.91-3.35 (m, 9 H); ESI-MS: m/z 245.3 (M+H)$^+$.

Example 134

4-(4-(1-Methylcyclopropyl)piperazin-1-ylsulfonyl) benzonitrile

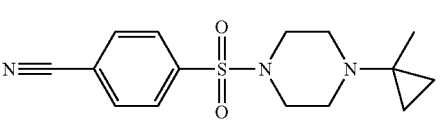

The title compound was prepared ad described in the Scheme 5. $^1$H NMR (400 MHz, DMSO-D6) δ ppm 0.25-0.30 (m, 2 H), 0.31-0.36 (m, 2 H), 0.96 (s, 3 H), 2.58 (t, J=4.93 Hz, 4 H), 2.84 (m, 4 H), 7.88 (d, J=8.08 Hz, 2 H), 8.12 (d, J=8.08 Hz, 2 H); ESI-MS: m/z 306.3 (M+H)$^+$.

Example 135

1-(4-Isopropoxyphenylsulfonyl)-4-(1-methylcyclopropyl)piperazine

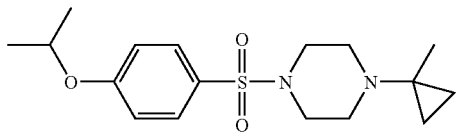

The title compound was prepared and described in the Scheme 5. $^1$H NMR (400 MHz, DMSO-D6) δ ppm 0.24-0.30 (m, 2 H), 0.32-0.37 (m, 2 H), 0.97 (s, 3 H), 1.28 (d, J=5.56 Hz, 6H), 2.58 (t, J=4.80 Hz, 4 H), 2.65-2.85 (m, 4 H), 4.67-4.79 (hept, J=6.01 Hz, 1 H), 7.10 (d, J=8.59 Hz, 2 H), 7.59 (d, J=8.59 Hz, 2 H); ESI-MS: m/z 339.4 (M+H)$^+$.

Example 136

1-(4-(Difluoromethyoxy)phenylsulfonyl)-4-(1-methylcyclopropyl)piperazine

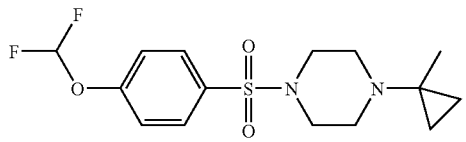

The title compound was prepared as described in the Scheme 5. $^1$H NMR (400 MHz, DMSO-D6) δ ppm 0.25-0.30 (m, 2 H), 0.31-0.37 (m, 2 H), 0.97 (s, 3 H), 2.58 (t, J=4.80 Hz, 4H), 2.79 (m, 4 H), 7.40 (d, J=8.84 Hz, 2 H), 7.41 (t, $J_{H-F}$=73.1 Hz, 1 H), 7.77 (d, J=8.84 Hz, 2 H); ESI-MS: m/z 347.3 (M+H)$^+$.

Example 137

1-(3-(Difluoromethoxy)phenylsulfonyl)-4-(1-methylcyclopropyl)piperazine

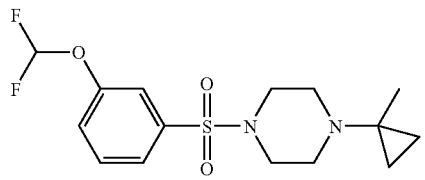

The title compound was prepared as described in the Scheme 5. $^1$H NMR (400 MHz, DMSO-D6) δ ppm 0.25-0.30 (m, 2 H), 0.31-0.38 (m, 2 H), 0.96 (s, 3 H), 2.58 (t, J=4.80 Hz, 4H), 2.83 (m, 4 H), 7.19-7.93 (m, 1 H), 7.38 (t, $J_{H-F}$=73.2 Hz, 1 H), 7.43 (m, 1 H), 7.54 (dd, J=8.08, 2.53 Hz, 1 H), 7.56-7.60 (m, 1 H), 7.71 (t, J=8.08 Hz, 1 H); ESI-MS: m/z 347.3 (M+H)$^+$.

Example 138

1-(1-Methylcyclopropyl)-4-(perfluorophenylsulfonyl)piperazine

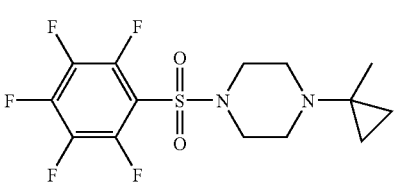

The title compound was prepared as described in the Scheme 5. $^1$H NMR (400 MHz, DMSO-D6) δ ppm 0.29-0.35 (m, 2 H), 0.35-0.42 (m, 2 H), 1.00 (s, 3 H), 2.65 (t, J=4.93 Hz, 4H), 3.07 (m, 4 H); ESI-MS: m/z 371.3 (M+H)$^+$.

Example 139

(1-(4-(2-chlorophenylsulfonyl)piperazin-1-yl)cyclobutyl)methanol

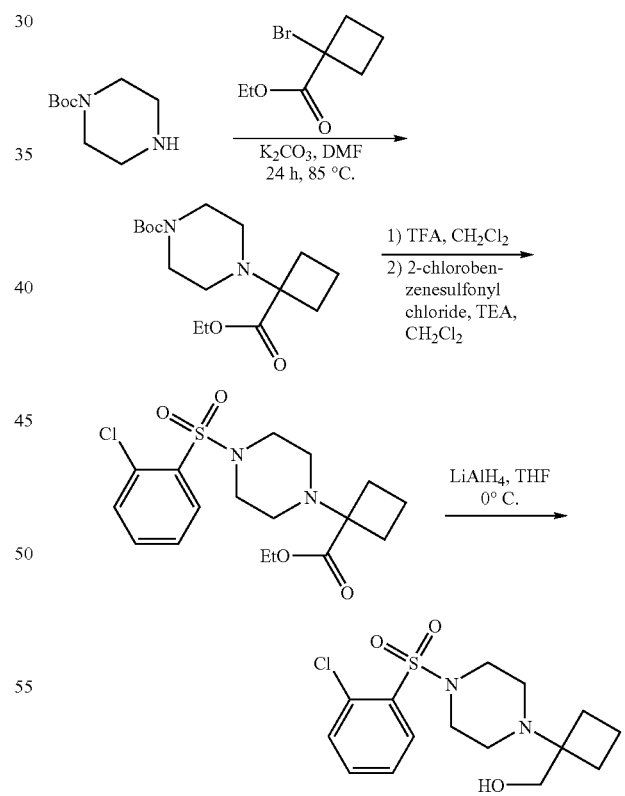

Tert-Butyl piperazine-1-carboxylate (0.50 g, 2.7 mmol) and ethyl 1-bromocyclobutanecarboxylate (0.52 ml, 3.2 mmol) were dissolved in DMF (5 ml). Potassium carbonate was added, and the mixture was heated to 85° C. for 24 h. The mixture was diluted with brine and then extracted twice with EtOAc. Combined organic layers were washed once with brine, dried over MgSO₄, filtered and concentrated. The crude product was purified by column chromatography (SiO₂, gradient, 45-55% EtOAc/hexanes) to give tert-butyl 4-(1-(ethoxycarbonyl)cyclobutyl)piperazine-1-carboxylate as a colorless oil (223 mg, 27%).

Ethyl 1-(piperazin-1-yl)cyclobutanecarboxylate (220 mg, 0.71 mmol) was dissolved in CH₂Cl₂ (4 ml), and TFA (1 ml) was added at room temperature. The mixture was stirred for 3 h. All volatiles were removed in vacuo. Residue was re-suspended in toluene and re-concentrated. After drying in vacuo, ethyl 1-(piperazin-1-yl)cyclobutanecarboxylate, trifluoroacetic acid salt, was obtained as an orange oil and was not further purified before the next reaction.

Ethyl 1-(piperazin-1-yl)cyclobutanecarboxylate (0.71 mmol) was dissolved in CH₂Cl₂ (5 ml). Triethylamine (0.30 ml, 2.1 mmol), followed by 2-chlorobenzenesulfonyl chloride (0.11 ml, 0.79 mmol), was added at room temperature. The orange-colored solution was stirred at room temperature for 6 h before saturated NaHCO₃ solution was added. The mixture was extracted twice with EtOAc. Combined organic layers were washed once with brine, dried over MgSO₄, filtered and concentrated. The crude product was purified by column chromatography (SiO₂, gradient 5-10% Et₂O/CH₂Cl₂) to give ethyl 1-(4-(2-chlorophenylsulfonyl)piperazin-1-yl)cyclobutanecarboxylate as a colorless oil.

Ethyl 1-(4-(2-chlorophenylsulfonyl)piperazin-1-yl)cyclobutanecarboxylate was dissolved in THF (1 ml). Lithium aluminum hydride (0.5 ml, 1.0 M in THF) was added at 0° C. The reaction mixture was stirred at 0° C. for 45 minutes. It was quenched by careful addition of H₂O at 0° C. The mixture was stirred for another 30 minutes before 1N NaOH and equal volume of brine were added. The mixture was extracted with EtOAc three times. Combined organic layers were dried over MgSO₄, filtered and concentrated in vacuo. The crude product was purified by column chromatography (SiO₂, 7% MeOH/CH₂Cl₂) to give the title compound (20 mg, 8% 3 steps) as a white solid. ¹H NMR (400 MHz, CHLOROFORM-D) δ ppm: 1.38-1.48 (m, 1 H), 1.67-1.78 (m, 1 H), 1.80-1.89 (m, 1 H), 1.91-2.00 (m, 1 H), 2.34-2.51 (m, 4 H), 2.56-2.68 (m, 2 H), 2.64 (bs, 1 H), 3.28-3.31 (m, 4 H), 3.57 (ddd, J=16.8, 10.9, 5.9 Hz, 2 H), 7.36-7.41 (m, 1 H), 7.45-7.53 (m, 2 H), 8.01 (dd, J=7.8, 1.5 Hz, 1 H); ESI-MS: m/z 345.3 (M+H)⁺.

Example 140

Ethyl 1-(4-(2-chlorophenylsulfonyl)piperazin-1-yl)cyclopropanecarboxylate

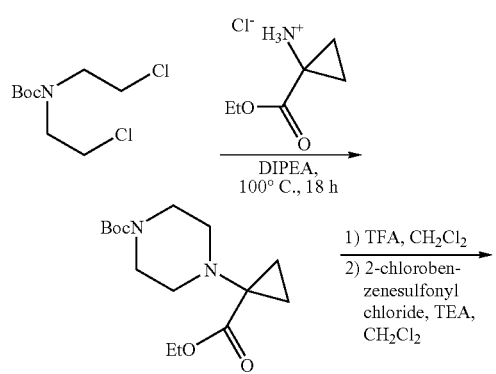

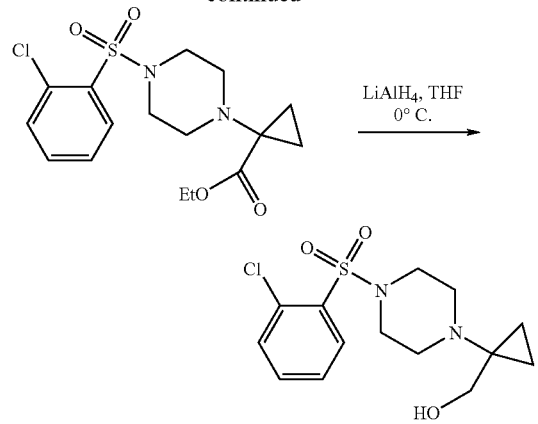

1-aminocyclopropane-1-carboxylic acid ethyl ester (440 mg, 2.6 mmol) was suspended in diisopropylethylamine (2 ml). Tert-Butyl bis(2-chloroethyl)carbamate (610 mg, 2.5 mmol, prepared according to Evans et al. *J. Med. Chem.* 1992, 35, 3919) was added at room temperature. The suspension was stirred at room temperature for 10 minutes before being heated to 100° C. for 18 h. The resulting biphasic mixture was cooled to room temperature. Brine was added and the mixture was extracted three times with EtOAc. Combined organic layers were dried over MgSO₄, filtered and concentrated in vacuo. The crude product was purified by column chromatography (SiO₂, 20% EtOAc/hexanes) to give tert-butyl 4-(1-(ethoxycarbonyl)cyclopropyl)piperazine-1-carboxylate as a colorless oil (60 mg, 8% 2 steps). ¹H NMR (400 MHz, CHLOROFORM-D) δ ppm: 0.91 (m, 2 H), 1.22 (t, J=7.2 Hz, 3 H), 1.25 (m, 2H), 1.43 (s, 9 H), 2.87 (bs, 4 H), 3.27 (bs, 4 H), 4.09 (q, J=7.2 Hz, 2 H); ¹³C NMR (100 MHz, CHLOROFORM-D) δ ppm 14.3, 19.0, 28.4, 45.7, 49.0, 60.2, 79.4, 154.8, 174.0; ESI-MS: m/z 299.4 (M+H)⁺.

Tert-butyl 4-(1-(ethoxycarbonyl)cyclopropyl)piperazine-1-carboxylate (60 mg, 0.20 mmol) was dissolved in CH₂Cl₂ (2 ml), and TFA (1 ml) was added at room temperature. The mixture was stirred for 2 h. All volatiles were removed in vacuo. Residue was re-suspended in toluene and re-concentrated. After drying in vacuo, ethyl 1-(piperazin-1-yl)cyclopropanecarboxylate, trifluoroacetic acid salt, was obtained as a colorless oil and was not further purified before the next reaction.

Ethyl 1-(piperazin-1-yl)cyclobutanecarboxylate (0.20 mmol) was dissolved in CH₂Cl₂ (1 ml). Triethylamine (0.30 ml, 2.2 mmol), followed by 2-chlorobenzenesulfonyl chloride (64 mg, 0.30 mmol), was added at room temperature. The orange-colored solution was stirred at room temperature for 18 h before saturated NaHCO₃ solution was added. The mixture was extracted twice with EtOAc. Combined organic layers were washed once with brine, dried over MgSO₄, filtered and concentrated. The crude product was purified by column chromatography (SiO₂, 25% EtOAc/hexanes) to give ethyl 1-(4-(2-chlorophenylsulfonyl)piperazin-1-yl)cyclopropanecarboxylate (47 mg, 63% 2 steps) as a white solid. ¹H NMR (400 MHz, CHLOROFORM-D) δ ppm: 0.85 (m, 2 H), 1.23 (t, J=7.5 Hz, 3 H), 1.23 (m, 2 H), 2.98 (bs, 4 H), 3.14 (bs, 4 H), 4.09 (q, J=7.2 Hz, 2 H), 7.37 (t, J=7.3 Hz, 1 H), 7.42-7.53 (m, 2 H), 8.00 (d, J=7.8 Hz, 1 H), $^{13}$C NMR (100 MHz, CHLOROFORM-D) δ ppm 14.3, 19.1, 45.7, 46.7, 48.8, 60.5, 126.9, 132.1, 132.2, 132.3, 133.6, 136.0, 173.8; ESI-MS: m/z 373.3 (M+H)$^+$.

Ethyl 1-(4-(2-chlorophenylsulfonyl)piperazin-1-yl)cyclobutanecarboxylate (47 mg, 0.13 mmol) was dissolved in THF (3 ml). Lithium aluminum hydride (0.32 ml, 1.0 M in THF) was added at 0° C. The reaction mixture was stirred at 0° C. for 45 minutes. It was quenched by careful addition of EtOAc at 0° C. The mixture was stirred for another 30 minutes before 1N NaOH and equal volume of brine were added. The mixture was extracted with EtOAc three times. Combined organic layers were dried over MgSO$_4$, filtered and concentrated in vacuo. The crude product was purified by column chromatography (SiO$_2$, 70% EtOAc/hexanes) to give the title compound (20 mg, 8% 3 steps) as a colorless oil. $^1$H NMR (400 MHz, CHLOROFORM-D) δ ppm: 0.51-0.54 (m, 2 H), 0.60-0.63 (m, 2 H), 1.74 (bs, 1 H), 2.80-2.84 (m, 4 H), 3.17-3.24 (m, 4 H), 3.56 (s, 2 H), 7.38 (td, J=7.4, 1.6 Hz, 1 H), 7.45-7.52 (m, 2 H), 8.00 (dd, J=7.7, 1.6 Hz, 1 H); $^{13}$C NMR (100 MHz, CHLOROFORM-D) δ ppm 12.2, 46.5, 46.6, 49.7, 64.7, 127.0, 132.1, 132.3, 132.4, 133.6, 135.9; ESI-MS: m/z 331.2 (M+H)$^+$.

Example 141

4-(2-chlorophenylsulfonyl)-1-cyclopentylpiperidine

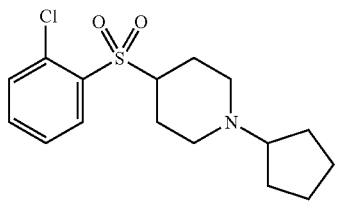

Step A: Tert-butyl 4-(2-chlorophenylthio)piperidine-1-carboxylate

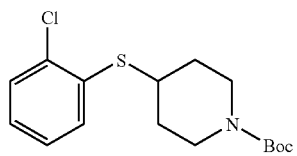

Tert-butyl 4-(methylsulfonyloxy)piperidine-1-carboxylate (2.00 g, 7.16 mmol, prepared according to Blurton et al., WO 00/43362), 2-chlorobenzenethiol (0.898 ml, 7.88 mmol), and potassium carbonate (1.58 g, 11.5 mmol) were stirred together in acetonitrile (15 ml). The reaction was heated to 75° C. and was stirred at that temperature for 15 h. After cooling to room temperature, brine was added, and the mixture was extracted with EtOAc three times. Combined organic layers were dried over MgSO$_4$, filtered and concentrated in vacuo.

Step B: Tert-butyl 4-(2-chlorophenylsulfonyl)piperidine-1-carboxylate

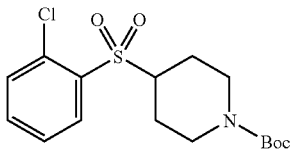

3-Chloroperoxybenzoic acid (70-75%, 1.94 g, 7.88 mmol) was added to tert-butyl 4-(2-chlorophenylthio)piperidine-1-carboxylate (7.61 mmol) from Step A in dichloromethane (30 ml) at 0° C. The mixture was stirred at 0° C. for 2 h. Additional 3-chloropeoxybenzoic acid (2.19 g, 8.85 mmol) was added at room temperature, and the mixture was stirred for another 2 h. Saturated NaHCO$_3$ solution was added and the mixture was extracted 3 times with EtOAc. Combined organic layers were dried over MgSO$_4$, filtered and concentrated in vacuo. Crude product was purified by column chromatography (SiO$_2$, 30% EtOAc/hexanes) to give the desired intermediate (1.28 g, 75% 2 steps). $^1$H NMR (400 MHz, CDCl$_3$) δ 1.43 (m, 9 H) 1.77 (td, J=12.1, 4.3 Hz, 2 H) 1.83 (bs, 2 H) 2.71 (bs, 2 H) 3.59-3.69 (m, 1 H) 4.23 (bs, 2 H) 7.43-7.51 (m, 1 H) 7.52-7.61 (m, 2 H) 8.07 (d, J=7.3 Hz, 1 H); ESI-MS: m/z 382.2 (M+Na)$^+$.

Step C: 4-(2-chlorophenylsulfonyl)-1-cyclopentylpiperidine

Tert-butyl 4-(2-chlorophenylsulfonyl)piperidine-1-carboxylate (1.23 g, 3.42 mmol) from Step B was dissolved in dichloromethane (15 ml). After TFA (5 ml) was added at room temperature, the mixture was stirred at room temperature for 2 h. The mixture was then concentrated to dryness, re-suspended in toluene and re-concentrated to dryness. The residue was triturated with Et$_2$O to give the deprotected product as a white solid. This TFA salt product (110 mg, 0.293 mmol) was dissolved in acetonitrile (3 ml). Potassium carbonate (243 mg, 1.76 mmol), followed by cyclopentylbromide (0.047 ml, 0.44 mmol), was added. The mixture was heated to 70° C. for 18 h. Brine was added, and the mixture was extracted three times with EtOAc. Combined organic layers were dried over MgSO$_4$, filtered and concentrated. The crude product was purified by column chromatography (SiO$_2$, 5% MeOH/CH$_2$Cl$_2$) to give the desired title product (56 mg, 58%). $^1$H NMR (400 MHz, CDCl$_3$) δ ppm 1.34-1.44 (m, 2 H) 1.46-1.56 (m, 2H) 1.60-1.71 (m, 2 H) 1.78-1.85 (m, 2 H) 1.87-2.02 (m, 6 H) 2.47-2.57 (m, 1 H) 3.12-3.14 (m, 2 H) 3.42-3.52 (m, 1 H) 7.45 (ddd, J=8.0, 6.1, 2.3 Hz, 1 H) 7.51-7.58 (m, 2 H) 8.07 (d, J=7.6 Hz, 1 H); ESI-MS: m/z 328.3 (M+Na)$^+$.

Example 142

(R)-4-(3-methyl-4-(1-methylcyclopropyl)piperazin-1-ylsulfonyl)isoquinolin-1-ol

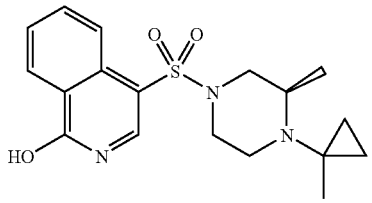

The title compound was prepared as described in Scheme 5 starting with commercially available (R)-tert-butyl 3-methylpiperazine-1-carboxylate. ¹H NMR (400 MHz, DMSO-D6) δ ppm 0.58-0.70 (m, 1 H) 0.71-0.89 (m, 2 H) 1.05-1.18 (m, 1 H) 1.20-1.30 (m, 6 H) 2.53-2.66 (m, 1 H) 2.76-2.91 (m, 1 H) 3.24-3.38 (m, 2 H) 3.75-3.92 (m, 3 H) 7.64 (t, J=7.07 Hz, 1H) 7.86 (td, J=7.83, 1.52 Hz, 1 H) 7.89 (d, J=6.57 Hz, 1 H) 8.18 (d, J=8.08 Hz, 1 H) 8.28 (dd, J=8.08, 1.52 Hz, 1 H) 8.86 (br s, 1 H) 12.19 (d, J=7.07 Hz, 1 H); ESI-MS: m/z 362.3 (M+H)⁺.

Example 143

(S)-4-(3-methyl-4-(1-methylcyclopropyl)piperazin-1-ylsulfonyl)isoquinolin-1-ol

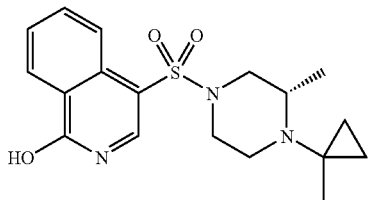

The title compound was prepared as described in Scheme 5 starting with commercially available (S)-tert-butyl 3-methylpiperazine-1-carboxylate. ¹H NMR (400 MHz, DMSO-D6) δ ppm 0.58-0.70 (m, 1 H) 0.71-0.89 (m, 2 H) 1.05-1.18 (m, 1 H) 1.20-1.30 (m, 6 H) 2.53-2.66 (m, 1 H) 2.76-2.91 (m, 1 H) 3.24-3.38 (m, 2 H) 3.75-3.92 (m, 3 H) 7.64 (t, J=7.07 Hz, 1H) 7.86 (td, J=7.83, 1.52 Hz, 1 H) 7.89 (d, J=6.57 Hz, 1 H) 8.18 (d, J=8.08 Hz, 1 H) 8.28 (dd, J=8.08, 1.52 Hz, 1 H) 8.87 (br s, 1 H) 12.18 (d, J=7.07 Hz, 1 H); ESI-MS: m/z 362.3 (M+H)⁺.

Example 144

4-(4-(1-methylcyclopropyl)piperazin-1-ylsulfonyl)isoquinolin-1-ol

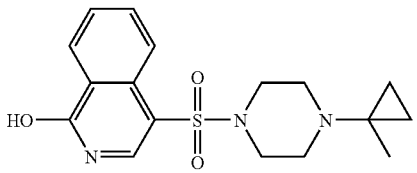

The title compound was prepared as described in Scheme 5. ¹H NMR (400 MHz, DMSO-D6) δ ppm 0.46-0.75 (m; 2 H) 0.76-1.09 (m, 2 H) 1.09-1.31 (m, 2 H) 2.72-3.90 (m, 8 H) 7.64 (t, J=7.45 Hz, 1 H) 7.82-7.91 (m, 2 H) 8.18 (d, J=8.34 Hz, 1 H) 8.28 (d, J=7.83 Hz, 1 H) 9.25 (s, 1 H) 12.19 (s, 1 H); ESI-MS: m/z 348.3 (M+H)⁺.

Example 145

(R)-4-(2-chlorophenylsulfonyl)-2-methyl-1-(1-methylcyclopropyl)piperazine

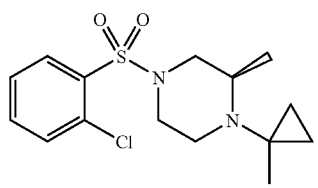

The title compound was prepared as described in Scheme 5 starting with commercially available (R)-tert-butyl 3-methylpiperazine-1-carboxylate. ¹H NMR (400 MHz, DMSO-D6) δ ppm 0.39-0.95 (m, 3 H) 0.99-1.48 (m, 7 H) 2.56-3.01 (m, 2 H) 3.09-3.66 (m, 3 H) 3.69-3.94 (m, 2 H) 7.57-7.64 (m, 1 H) 7.69-7.76 (m, 2 H) 7.98 (d, J=8.08 Hz, 1 H) 9.12 (br s, 1 H); ESI-MS: m/z 329.3 (M+H)⁺.

Example 146

(R)-4-(2-chlorophenylsulfonyl)-2-methyl-1-(1-methylcyclopropyl)piperazine

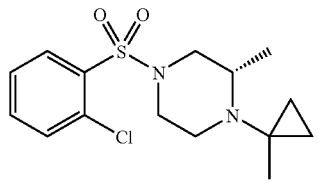

The title compound was prepared as described in Scheme 5 starting with commercially available (S)-tert-butyl 3-methylpiperazine-1-carboxylate. ¹H NMR (400 MHz, DMSO-D6) δ ppm 0.39-0.95 (m, 3 H) 0.99-1.48 (m, 7 H) 2.56-3.01 (m, 2 H) 3.09-3.66 (m, 3 H) 3.69-3.94 (m, 2 H) 7.57-7.64 (m, 1 H) 7.69-7.76 (m, 2 H) 7.98 (d, J=8.08 Hz, 1 H) 9.14 (br s, 1 H); ESI-MS: m/z 329.3 (M+H)⁺.

Example 147

(R)-1-(2-chlorophenylsulfonyl)-2-methyl-4-(1-methylcyclopropyl)piperazine

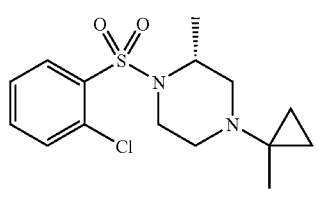

The title compound was prepared as a TFA salt as described in Scheme 10. ¹H NMR (400 MHz, DMSO-D6) δ ppm 0.24-1.33 (m, 10 H) 2.54-4.13 (m, 7 H) 7.56 (t, J=7.58 Hz, 1 H) 7.63-7.75 (m, 2 H) 8.04 (d, J=7.83 Hz, 1 H) 8.84 (br s, 1 H); ESI-MS: m/z 329.3 (M+H)⁺.

Example 148

1'-(2-chlorophenylsulfonyl)spiro[benzo[d][1,3]dioxole-2,4'-piperidine]

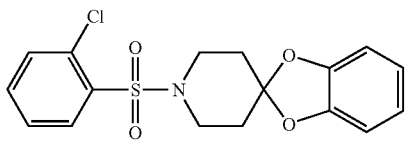

1-(2-chlorophenylsulfonyl)piperidin-4-one (137 mg, 0.500 mmol, prepared as described in Scheme 1) and catechol (55.6 mg, 0.500 mmol) were dissolved in toluene (3 mL) and pTSA (2 mg) was added. The reaction mixture was heated to reflux in Dean-Stark apparatus for 10 h and concentrated in vacuo. The crude product was purified by flash column chromatography on silica gel (25 g SiO$_2$, hexanes-ethyl acetate (2:1), 300 mL) to afford the title compound as a white solid (135.2 mg, 74%). $^1$H NMR (400 MHz, DMSO-D6) δ ppm 2.00-2.05 (m, 4 H) 3.37-3.44 (m, 4H) 6.78-6.89 (m, 4 H) 7.59 (ddd, J=8.27, 6.63, 1.52 Hz, 1 H) 7.71 (td, J=7.58, 1.52 Hz, 1 H) 7.75 (dd, J=8.08, 1.52 Hz 1 H) 8.02 (dd, J=7.83, 1.52 Hz, 1 H); ESI-MS: m/z 366.3 (M+H)$^+$.

Example 149

2-(4-(1-methylcyclopropyl)piperazin-1-ylsulfonyl)benzonitrile

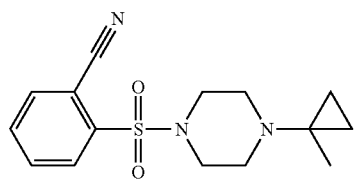

The title compound was prepared as described in Scheme 3. $^1$H NMR (400 MHz, DMSO-D6) δ ppm 0.29-1.29 (m, 7 H) 2.59-3.90 (m, 8 H) 7.89-8.05 (m, 3 H) 8.20 (d, J=6.82 Hz, 1 H) 8.98 (s, 1 H); ESI-MS: m/z 306.3 (M+H)$^+$.

Example 150

4-benzyl-7-(2-chlorophenylsulfonyl)-4,7-diazaspiro[2.5]octane

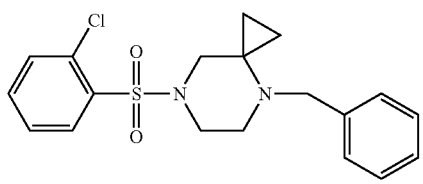

The title compound was prepared as described in Schemes 11. $^1$H NMR (400 MHz, DMSO-D6) δ ppm 0.48-0.55 (m, 2 H) 0.57-0.65 (m, 2 H) 2.71-2.77 (m, 2 H) 3.12 (s, 2 H) 3.24-3.28 (m, 2 H) 3.75 (s, 2 H) 7.17-7.28 (m, 5 H) 7.56 (ddd, J=7.89, 7.14, 1.64 Hz, 1 H) 7.68 (td, J=7.58, 1.52 Hz, 1 H) 7.72 (dd, J=8.08, 1.52 Hz, 1 H) 7.97 (dd, J=7.83, 1.52 Hz, 1 H); ESI-MS: m/z 377.3 (M+H)$^+$.

Example 151

1-(4-fluoronaphthalen-1-ylsulfonyl)-4-(1-methylcyclopropyl)piperazine

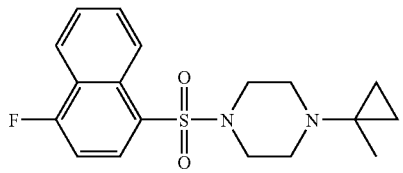

The title compound was prepared as described in Scheme 3. $^1$H NMR (400 MHz, DMSO-D6) δ ppm 0.22-0.28 (m, 2 H) 0.29-0.34 (m, 2 H) 0.91 (s, 3 H) 2.53 (t, J=4.93 Hz, 4 H) 2.91-3.03 (m, 4 H) 7.53 (dd, J=10.11, 8.34 Hz, 1 H) 7.77-7.81 (m, 1 H) 7.85 (ddd, J=8.53, 7.01, 1.39 Hz, 1 H) 8.15 (dd, J=8.34, 5.31 Hz, 1 H) 8.21 (d, J=8.34 Hz, 1 H) 8.70 (d, J=8.34 Hz, 1 H); ESI-MS: m/z 349.3 (M+H)$^+$.

Example 152

1-(2-chlorophenylsulfonyl)-4-(trifluoromethyl)piperidine

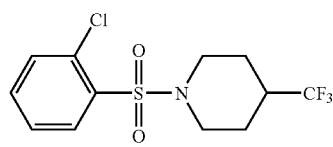

The title compound was prepared as described in Scheme 1. $^1$H NMR (400 MHz, DMSO-D6) δ ppm 1.38 (app qd, J=12.59, 4.67 Hz, 2 H) 1.86 (d, J=13.14 Hz, 2 H) 2.50-2.60 (m, 1 H) 2.78 (app t, J=12.63 Hz, 2 H) 3.79 (d, J=13.14 Hz, 2 H) 7.54-7.60 (m, 1 H) 7.65-7.73 (m, 2 H) 7.96-8.02 (m, 1 H); ESI-MS: m/z 328.2 (M+H)$^+$.

Example 153

1-(2-chlorophenylsulfonyl)-4-cyclopropylpiperazine

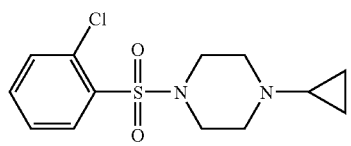

The title compound was prepared as described in Scheme 2 (Step B). $^1$H NMR (400 MHz, DMSO-D6) δ ppm 0.23-0.27 (m, 2 H) 0.36-0.41 (m, 2 H) 1.59-1.66 (m, 1 H) 2.52-2.57 (m, 4H) 3.07-3.13 (m, 4 H) 7.56 (ddd, J=7.77, 6.88, 2.02 Hz, 1 H) 7.65-7.72 (m, 2 H) 7.94 (dd, J=7.83, 1.52 Hz, 1 H); ESI-MS: m/z 301.2 (M+H)+.

Example 154

(S)-N-cyclopentyl-1-(quinolin-8-ylsulfonyl)pyrrolidin-3-amine

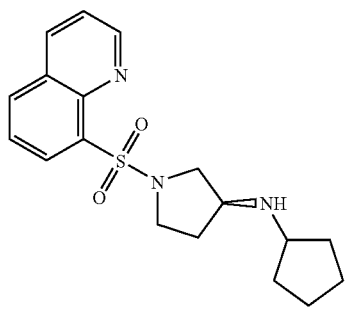

The title compound was prepared as described in Scheme 7. ¹H NMR (300 MHz, MeOD) δ ppm 1.03-1.24 (m, 2 H) 1.34-1.53 (m, 2 H) 1.53-1.82 (m, 5 H) 1.96-2.12 (m, 1 H) 2.81-3.00 (m, 1 H) 3.06-3.22 (m, 2 H) 3.39-3.53 (m, 1 H) 3.78-3.90 (m, 1 H) 3.96-4.07 (m, 1 H) 4.82 (br s, 1 H) 7.61 (dd, J=8.48, 4.33 Hz, 1 H) 7.68 (dd, 1 H) 8.16 (dd, J=8.10, 1.32 Hz, 1 H) 8.42 (ddd, J=15.26, 7.91, 1.70 Hz, 2 H) 9.05 (dd, J=4.14, 1.88 Hz, 1 H).

Example 155

(S)-8-(3-(azetidin-1-yl)pyrrolidin-1-ylsulfonyl)quinoline

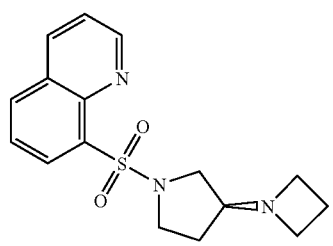

The title compound was prepared as described in Scheme 7. ¹H NMR (300 MHz, CHLOROFORM-d) δ ppm 1.53-1.64 (m, 1 H) 1.69-1.83 (m, 1 H) 1.88-1.99 (m, 2 H) 2.84 (dq, J=5.65, 5.40 Hz, 1 H) 2.99-3.13 (m, 4 H) 3.24 (dd, J=9.98, 4.71 Hz, 1 H) 3.61-3.74 (m, 2H) 3.83 (dt, J=9.42, 7.16 Hz, 1 H) 7.52 (dd, J=8.29, 4.14 Hz, 1 H) 7.57-7.64 (m, 1 H) 8.02 (dd, J=8.29, 1.51 Hz, 1 H) 8.24 (dd, J=8.48, 1.70 Hz, 1 H) 8.52 (dd, J=7.54, 1.51 Hz, 1 H) 9.07 (dd, J=4.33, 1.70 Hz, 1 H).

Example 156

(R)-4-(3-(dimethylamino)pyrrolidin-1-ylsulfonyl)isoquinolin-1-ol

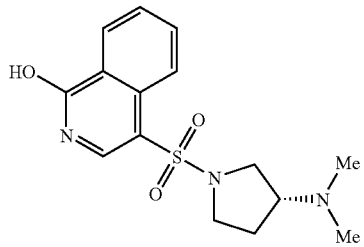

The title compound was prepared as described in Scheme 6. ¹H NMR (300 MHz, CHLOROFORM-d) δ ppm 1.80 (dq, J=12.39, 9.18 Hz, 1 H) 2.05-2.16 (m, 1 H) 2.21 (s, 6 H) 2.72-2.85 (m, 1 H) 3.12 (dd, J=9.42, 8.29 Hz, 1 H) 3.39 (td, J=9.61, 7.16 Hz, 1 H) 3.52 (m, 1 H) 3.64 (dd, J=9.23, 6.97 Hz, 1 H) 7.62 (ddd, J=8.01, 7.06, 1.13 Hz, 1 H) 7.81 (ddd, J=8.38, 7.06, 1.51 Hz, 1 H) 8.12 (s, 1 H) 8.32 (d, J=8.29 Hz, 1 H) 8.46 (dd, J=7.91, 1.51 Hz, 1 H).

Example 157

(S)-4-(3-(dimethylamino)pyrrolidin-1-ylsulfonyl)isoquinolin-1-ol

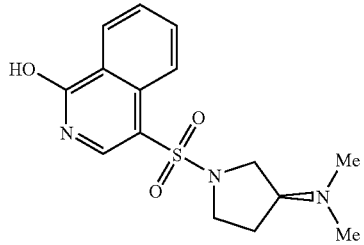

The title compound was prepared as described in Scheme 6. ¹H NMR (300 MHz, CHLOROFORM-d) δ ppm 1.80 (dq, J=12.39, 9.18 Hz, 1 H) 2.05-2.15 (m, 1 H) 2.21 (s, 6 H) 2.72-2.86 (m, 1 H) 3.09-3.18 (m, 1 H) 3.38 (td, J=9.61, 6.78 Hz, 1 H) 3.52 (td, J=9.23, 2.64 Hz, 1 H) 3.64 (dd, J=9.04, 7.16 Hz, 1 H) 7.62 (t, J=7.72 Hz, 1 H) 7.80 (ddd, J=8.38, 7.06, 1.51 Hz, 1 H) 8.13 (s, 1 H) 8.32 (d, J=8.29 Hz, 1 H) 8.46 (dd, J=7.91, 1.51 Hz, 1 H).

Example 158

(R)-N,N-dimethyl-1-(quinolin-8-ylsulfonyl)pyrrolidin-3-amine

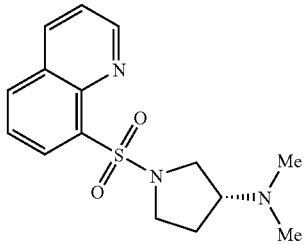

The title compound was prepared as described in Scheme 6. $^1$H NMR (300 MHz, CHLOROFORM-d) δ ppm 1.60-1.76 (m, 1 H) 1.95-2.11 (m, 1 H) 2.20 (s, 6 H) 2.53-2.66 (m, 1 H) 3.15 (t, J=9.23 Hz, 1 H) 3.47 (td, J=10.17, 6.78 Hz, 1 H) 3.97-4.05 (m, 1 H) 4.10 (dd, J=9.04, 7.16 Hz, 1 H) 7.53 (dd, J=8.29, 4.14 Hz, 1 H) 7.62 (t, J=7.91 Hz, 1 H) 8.03 (dd, J=8.10, 1.32 Hz, 1 H) 8.25 (dd, J=8.48, 1.70 Hz, 1 H) 8.51 (dd, J=7.54, 1.51 Hz, 1 H) 9.07 (dd, J=4.14, 1.88 Hz, 1 H).

Example 159

(S)-N,N-dimethyl-1-(quinolin-8-ylsulfonyl)pyrrolidin-3-amine

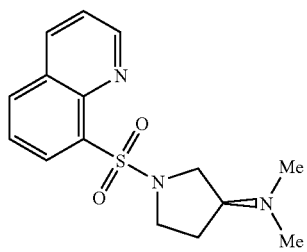

The title compound was prepared as described in Scheme 6. $^1$H NMR (300 MHz, CHLOROFORM-d) δ ppm 1.60-1.76 (m, 1 H) 1.95-2.11 (m, 1 H) 2.20 (s, 6 H) 2.53-2.66 (m, 1 H) 3.15 (t, J=9.23 Hz, 1 H) 3.47 (td, J=10.17, 6.78 Hz, 1 H) 3.97-4.05 (m, 1 H) 4.10 (dd, J=9.04, 7.16 Hz, 1 H) 7.53 (dd, J=8.29, 4.14 Hz, 1 H) 7.62 (t, J=7.91 Hz, 1 H) 8.03 (dd, J=8.10, 1.32 Hz, 1 H) 8.25 (dd, J=8.48, 1.70 Hz, 1 H) 8.51 (dd, J=7.54, 1.51 Hz, 1 H) 9.07 (dd, J=4.14, 1.88 Hz, 1 H).

Example 160

(R)-1-(1-chloroisoquinolin-4-ylsulfonyl)-N-(cyclopropylmethyl)pyrrolidin-3-amine

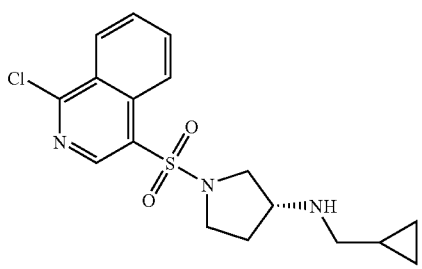

The title compound was prepared as described in Scheme 7. $^1$H NMR (300 MHz, CHLOROFORM-d) δ ppm 0.05-0.03 (m, 2 H) 0.36-0.45 (m, 2 H) 0.69-0.83 (m, 1 H) 1.64-1.76 (m, 1 H) 2.00-2.14 (m, 1 H) 2.25-2.37 (m, 2 H) 3.16 (dd, J=9.80, 4.90 Hz, 1 H) 3.34 (dq, J=5.65, 5.40 Hz, 1 H) 3.41-3.52 (m, 2 H) 3.56 (dd, J=9.98, 5.84 Hz, 1 H) 7.73-7.83 (m, 1 H) 7.90 (ddd, J=8.57, 7.06, 1.32 Hz, 1 H) 8.44 (d, J=7.91 Hz, 1 H) 8.78 (d, J=8.67 Hz, 1 H) 8.88 (s, 1 H).

Example 161

(R)-4-(3-(cyclopropylmethylamino)pyrrolidin-1-ylsulfonyl)isoquinolin-1-ol

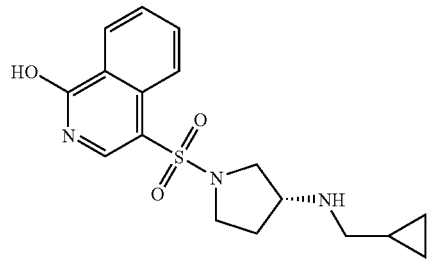

The title compound was prepared as described in Scheme 7. $^1$H NMR (300 MHz, CHLOROFORM-d) δ ppm −0.04-0.04 (m, 2 H) 0.34-0.43 (m, 2 H) 0.73-0.87 (m, 1 H) 1.66-1.78 (m, 1 H) 2.01-2.15 (m, 1 H) 2.29-2.41 (m, 2 H) 3.13 (dd, J=9.80, 4.90 Hz, 1 H) 3.31-3.45 (m, 3 H) 3.45-3.54 (m, 1 H) 7.50-7.58 (m, 1 H) 7.74 (ddd, J=8.48, 7.35, 1.51 Hz, 1 H) 8.09 (s, 1 H) 8.28 (d, J=8.29 Hz, 1 H) 8.37 (d, J=7.16 Hz, 1 H).

Example 162

(R)-4-(3-(azetidin-1-yl)pyrrolidin-1-ylsulfonyl)-1-chloroisoquinoline

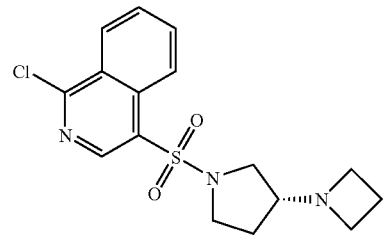

The title compound was prepared as described in Scheme 7. $^1$H NMR (300 MHz, CHLOROFORM-d) δ ppm 1.72 (ddd, J=13.09, 6.88, 3.01 Hz, 1 H) 1.78-1.90 (m, 1 H) 1.90-2.00 (m, 2 H) 2.88-2.97 (m, 3 H) 2.98-3.10 (m, 3 H) 3.17 (dd, J=9.98, 2.45 Hz, 1 H) 3.43-3.50 (m, 12H) 3.50-3.58 (m, 1 H) 7.77-7.84 (m, 1 H) 7.89-7.96 (m, 1 H) 8.48 (d, J=7.54 Hz, 21H) 8.81 (d, J=8.67 Hz, 1 H) 8.95 (s, 1 H).

Example 163

(R)-4-(3-(azetidin-1-yl)pyrrolidin-1-ylsulfonyl)isoquinolin-1-ol

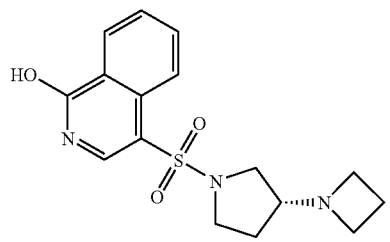

The title compound was prepared as described in Scheme 7. ¹H NMR (300 MHz, DMSO-D6) δ ppm ¹H NMR (300 MHz, MeOD) δ ppm 1.58-1.71 (m, 1 H) 1.80-1.92 (m, 1 H) 1.92-2.04 (m, 2 H) 2.94-3.19 (m, 6 H) 3.32-3.43 (m, 3 H) 7.63 (t, J=7.16 Hz, 1 H) 7.80-7.88 (m, 1 H) 7.99 (s, 1 H) 8.34-8.43 (m, 2 H).

Example 164

(R)-1-(5-(3-(dimethylamino)pyrrolidin-1-ylsulfonyl)indolin-1-yl)ethanone

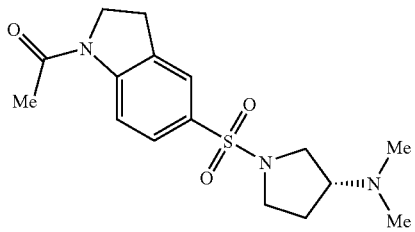

The title compound was prepared as described in Scheme 6. ¹H NMR (300 MHz, CHLOROFORM-d) δ ppm 1.55-1.70 (m, 1 H) 1.92-2.08 (m, 1 H) 2.18 (s, 6 H) 2.27 (s, 3 H) 2.56-2.71 (m, 1 H) 2.91 (t, J=8.90 Hz, 2 H) 3.19-3.31 (m, 2 H) 3.31-3.41 (m, 1 H) 3.51 (dd, J=9.09, 7.19 Hz, 1 H) 4.16 (t, J=8.52 Hz, 2 H) 7.61 (s, 1 H) 7.67 (dd, J=8.71, 1.89 Hz, 1 H) 8.32 (d, J=8.71 Hz, 1 H).

Example 165

(R)-N,N-dimethyl-1-(2-methyl-4-(thiophen-3-yl)phenylsulfonyl)pyrrolidin-3-amine

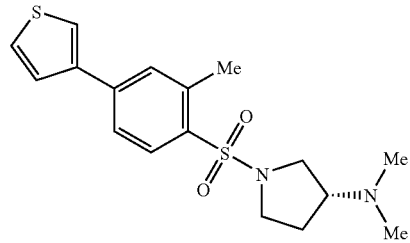

The title compound was prepared as described in Scheme 8, and was purified by HPLC.
¹H NMR (300 MHz, CHLOROFORM-d) δ ppm 2.22-2.46 (m, 2 H) 2.63 (s, 3 H) 2.87 (s, 6 H) 3.25-3.38 (m, 1 H) 3.45-3.61 (m, 2 H) 3.69 (m, 1 H) 3.79-3.95 (m, 1 H) 7.39 (m, 1 H) 7.42 (m, 1 H) 7.54 (s, 2 H) 7.57 (dd, J=2.83, 1.32 Hz, 1 H) 7.88 (d, J=8.29 Hz, 1 H).

Example 166

(R)-1-(indolin-5-ylsulfonyl)-N,N-dimethylpyrrolidin-3-amine

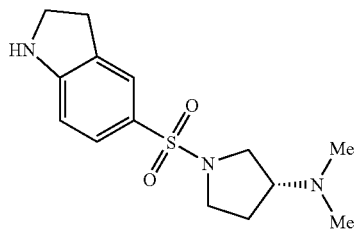

(R)-1-(5-(3-(dimethylamino)pyrrolidin-1-ylsulfonyl)indolin-1-yl)ethanone was dissolved in THF. A 2 N HCl solution of equal volume was added, and the reaction mixture was stirred at 60° C. for 1 h. Volatiles were removed in vacuo, and the product that was precipitated was collected on a fritted glass funnel, washed with water, and was dried in vacuo at 45° C. overnight to obtain the title compound in 65% yield. ¹H NMR (300 MHz, MeOD) δ ppm 2.02-2.22 (m, 1 H) 2.25-2.47 (m, 1 H) 2.88 (s, 6 H) 3.14-3.26 (m, 1 H) 3.28-3.33 (m, 2 H) 3.34-3.64 (m, 4 H) 3.82-4.01 (m, 2 H) 7.51-7.60 (m, 1 H) 7.87 (d, J=8.67 Hz, 1 H) 7.93 (s, 1 H).

Example 167

(R)-N,N-dimethyl-1-(3-methylbiphenyl-4-ylsulfonyl)pyrrolidin-3-amine

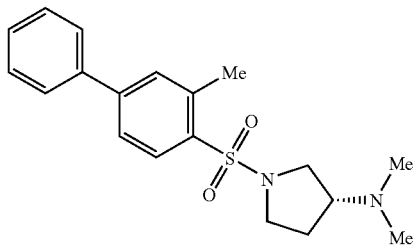

The title compound was prepared as described in Scheme 8, and was purified by HPLC. ¹H NMR (300 MHz, CHLOROFORM-d) δ ppm 2.19-2.33 (m, 1 H) 2.34-2.48 (m, 1 H) 2.64 (s, 3 H) 2.87 (s, 6 H) 3.24-3.37 (m, 1 H) 3.48-3.64 (m, 2 H) 3.65-3.74 (m, 1 H) 3.88 (m, 1 H) 7.37-7.59 (m, 7 H) 7.87-7.96 (m, 1 H).

Example 168

(R)-4-(3-(dimethylamino)pyrrolidin-1-ylsulfonyl)-3-methylbenzonitrile

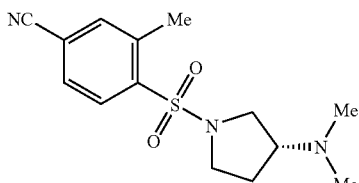

The title compound was prepared as described in Scheme 8. ¹H NMR (300 MHz, CHLOROFORM-d) δ ppm 2.31-2.50 (m, 2 H) 2.66 (s, 3 H) 2.93 (s, 6 H) 3.41-3.54 (m, 1 H) 3.54-3.67 (m, 2 H) 3.76-3.90 (m, 2 H) 7.60-7.69 (m, 2 H) 7.96-8.05 (m, 1 H).

Example 169

(R)-1-(4-(dimethylamino)-2-methylphenylsulfonyl)-N,N-dimethylpyrrolidin-3-amine

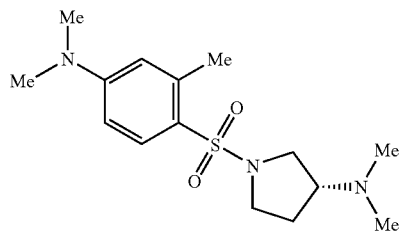

The title compound was prepared as a by-product as described in Scheme 8, and was purified by HPLC. $^1$H NMR (300 MHz, CHLOROFORM-d) δ ppm 2.33-2.47 (m, 2 H) 2.68 (s, 3 H) 2.85 (s, 6 H) 2.93 (s, 3 H) 3.01 (s, 3 H) 3.39-3.62 (m, 3 H) 3.70-3.84 (m, 2 H) 7.74 (d, J=8.33 Hz, 1 H) 7.79 (s, 1 H) 7.97 (d, J=7.95 Hz, 1 H).

Example 170

1-(4-chloro-5-(4-(1-methylcyclopropyl)piperazin-1-ylsulfonyl)indolin-1-yl)-2,2,2-trifluoroethanone

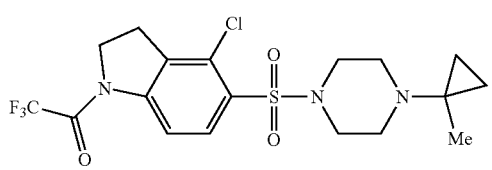

The title compound was prepared as described in Scheme 1. $^1$H NMR (500 MHz, CHLOROFORM-d) δ ppm 0.31-0.33 (m, 2 H) 0.46-0.48 (m, 2 H) 1.02 (s, 3 H) 2.66-2.68 (m, 4 H) 3.18 (br s, 4 H) 3.32 (t, J=8.44 Hz, 2 H) 4.39 (t, J=8.40 Hz, 2 H) 7.92 (d, J=8.80 Hz, 1 H) 8.14 (d, J=8.64 Hz, 1 H).

Example 171

4-chloro-5-(4-(1-methylcyclopropyl)piperazin-1-ylsulfonyl)indoline

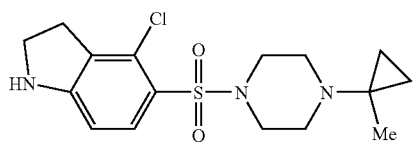

1-(4-chloro-5-(4-(1-methylcyclopropyl)piperazin-1-ylsulfonyl)indolin-1-yl)-2,2,2-trifluoroethanone was dissolved in 1 N sodium methoxide solution in methanol. The mixture was heated to 60° C. The reaction mixture was then concentrated in vacuo and the solid residue was purified by chromatography to give the title compound. $^1$H NMR (500 MHz, CHLOROFORM-d) δ ppm 0.32-0.33 (m, 2 H) 0.49 (br s, 2 H) 1.02 (s, 3 H) 2.67 (br s, 4 H) 3.09 (t, J=8.73 Hz, 2 H) 3.14 (br s, 4 H) 3.71 (t, J=8.71 Hz, 2 H) 6.38 (d, J=8.40 Hz, 1 H) 7.63 (d, J=8.35 Hz, 1 H).

Example 172

1-chloro-4-(4-(1-methylcyclopropyl)piperazin-1-ylsulfonyl)isoquinoline

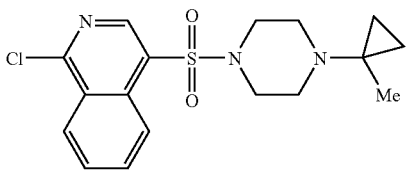

The title compound was prepared as described in Scheme 1. $^1$H NMR (400 MHz, CHLOROFORM-d) δ ppm 0.28-0.33 (m, 2 H) 0.39-0.44 (m, 2 H) 1.00 (s, 3 H) 2.68 (t, J=4.93 Hz, 4 H) 3.15 (br s, 4 H) 7.82 (ddd, J=8.34, 7.07, 1.01 Hz, 1 H) 7.93 (ddd, J=8.53, 7.01, 1.39 Hz, 1 H) 8.48 (d, J=7.83 Hz, 1 H) 8.77 (d, J=8.84 Hz, 1 H) 8.82 (s, 1 H).

Example 173

4-(2-(4-(4-(1-methylcyclopropyl)piperazin-1-ylsulfonyl)isoquinolin-1-yloxy)ethyl)morpholine

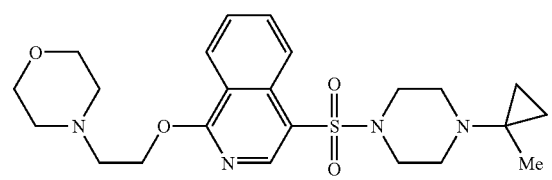

The title compound was prepared as described in Scheme 9. $^1$H NMR (400 MHz, CHLOROFORM-d) δ ppm 0.26-0.30 (m, 2 H) 0.36-0.42 (m, 2 H) 0.98 (s, 3 H) 2.60-2.63 (m, 4 H) 2.65 (t, J=4.93 Hz, 4 H) 2.91 (t, J=5.81 Hz, 2 H) 3.10 (br s, 4 H) 3.69-3.76 (m, 4 H) 4.72 (t, J=5.81 Hz, 2 H) 7.62 (t, J=7.71 Hz, 1 H) 7.78 (ddd, J=8.46, 7.07, 1.14 Hz, 1 H) 8.30 (d, J=8.34 Hz, 1 H) 8.56-8.62 (m, 2 H); ESI-MS: m/z 461.4 (M+H)$^+$.

Example 174

4-(4-(1-methylcyclopropyl)piperazin-1-ylsulfonyl)-N-(2-morpholinoethyl)isoquinolin-1-amine

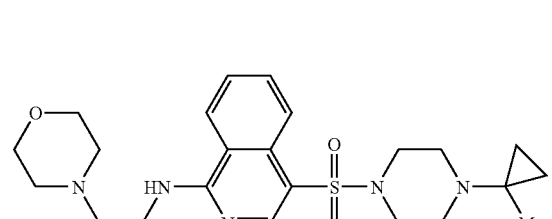

The title compound was prepared as described in Scheme 9. $^1$H NMR (400 MHz, CHLOROFORM-d) δ ppm 0.25-0.31 (m, 2 H) 0.37-0.43 (m, 2 H) 0.97 (s, 3 H) 2.52-2.59 (m, 4 H) 2.63 (t, J=4.80 Hz, 4 H) 2.74 (t, J=5.81 Hz, 2 H) 3.08 (br s, 4 H) 3.70 (q, J=5.56 Hz, 2 H) 3.73-3.79 (m, 4 H) 7.55 (t, J=7.71 Hz, 1 H) 7.69 (t, J=7.83 Hz, 1 H) 7.78 (d, J=8.08 Hz, 1 H) 8.55 (d, J=8.59 Hz, 1 H) 8.58 (s, 1 H).

Example 175

4-(4-cyclopropylpiperazin-1-ylsulfonyl)isoquinolin-1-ol

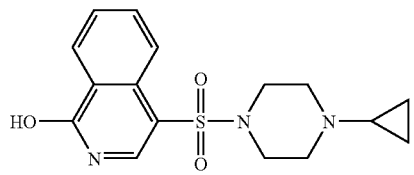

The title compound was prepared as described in Scheme 1. $^1$H NMR (400 MHz, CHLOROFORM-d) δ ppm 0.28-0.36 (m, 2 H) 0.38-0.47 (m, 2 H) 1.55-1.67 (m, 1 H) 2.65 (t, J=4.55 Hz, 4 H) 3.14-3.28 (m, 4 H) 7.62 (t, J=7.58 Hz, 1 H) 7.77-7.85 (m, 1 H) 8.08 (s, 1 H) 8.32 (d, J=8.34 Hz, 1 H) 8.46 (d, J=8.08 Hz, 1 H) 11.81 (s, 1 H).

Biological Testing

The activity of compounds as 11b-HSD1 inhibitors may be assayed in vitro, in vivo or in a cell line. Provided below is an in vitro enzymatic 11b-HSD1 dehydrogenase activity assay for activity against 11b-HSD1.

It should be noted that a variety of other expression systems and hosts are also suitable for the expression of 11b-HSD1, as would be readily appreciated by one of skill in the art.

Purified 11b-HSD1 may be obtained as follows: Residues 24 to 292 of 11-β-hydroxysteroid dehydrogenase isoform 1 was amplified from IMAGE clone 5193867 (ATCC clone 7277078) using PCR with the primers hsd1__24-f: 5'-AAC-GAGGAATTCAGACCAGAGATG-3' (SEQ. ID No. 1) and hsd1-292-r: 5'-TTACTTGTTTATGAATCTGTCCAT-3' (SEQ. ID No. 2). The resulting PCR product was topocloned into the pBAD-ThioE vector (Invitrogen) that was modified by inserting a DNA sequence that codes for MKHQHQHQHQHQHQQPL at the cloning site and adapted for TOPOcloning PCR (Invitrogen). Residues 24-292 of 11-β-hydroxysteroid dehydrogenase isoform 1 were generated fused with MKHQHQHQHQHQHQQPL at the N-terminus under control of an ara promoter.

E. coli DH 10b-Tir (Invitrogen), harboring the 11b-HSD1 expression plasmid, were grown overnight at 37° C., in Luria broth (LB) supplemented to 0.05 mg/ml kanamycin (Km). 15 mls of saturated culture was then used to inoculate one liter of fresh LB (0.05 mg/ml Km). When this culture reached an optical density of 0.4 (λ=600 nm), the growth temperature was shifted from 37° C. to 25° C. After an additional 2 hours of growth, arabinose and corticosterone were added to a final concentration of 0.2% (w/w), and 0.25 mM, respectively. Cells were harvested approximately 14 hours following induction, and were immediately frozen at −80° C. The cell pellets from each liter of cell culture were thawed and resuspended in 50 mls of lysis buffer (30 mM CHAPS, 50 mM Tris-HCl, pH 7.9, 0.15 M NaCl, 0.5 µl/ml benzonase, 1 µl/ml ReadyLyse). Following a 30-minute incubation at room temperature, the lysates were clarified by centrifugation. The resulting supernatant was loaded on 6 mls of Probond resin (Invitrogen), previously equilibrated with wash buffer (4 mM CHAPS, 50 mM Tris-HCl, pH 7.9, 0.25 M NaCl, 40 mM imidazole), and then washed with 10 column volumes of wash buffer. 11b-HSD1 was then eluted with 3 column volumes of wash buffer supplemented to 0.2 M imidazole. The eluate of purified 11b-HSD1 was extensively dialysed against 4 mM CHAPS, 25 mM Tris-HCl, pH 7.9, 0.25 M NaCl, and concentrated to 10 mg/ml. Size exclusion chromatography demonstrated that this method of purification yields monodispersive 11b-HSD1.

It should be noted that a variety of other expression systems and hosts are also suitable for the expression of 11b-HSD1, as would be readily appreciated by one of skill in the art.

The inhibitory properties of compounds relative to 11b-HSD1 may be determined using a white 384-well-plate format under the following reaction conditions: 50 mM Tris pH 7.5, 150 mM NaCl, 0.1 mM EDTA, 0.01% Brij35, 10 µM each of cortisol and NADP$^+$, 1% DMSO. Reaction product may be determined quantitatively by fluorescence intensity using a fluorescence plate reader (Molecular Devices Gemini) with a 340 nm excitation wavelength and a 460 nm emission wavelength.

The assay reaction may be initiated as follows: 4 µl buffer containing 25 µM cortisol and 25 µM NADP$^+$ was added to each well of the plate, followed by the addition of 2 µl of inhibitor (2 fold serial dilutions for 11 data points for each inhibitor) containing 5% DMSO. 4 µl of 125 nM 11b-HSD1 enzyme solution may be added to initiate the reaction (final enzyme concentrations was 50 nM). Fluorescence intensities of the resulting reaction mixtures may be measured after 60 minutes incubation at room temperature.

IC50 values may be calculated by non-linear curve fitting of the compound concentrations and fluorescence intensities to the standard IC50 equation. As a reference point for this assay, carbenoxolone and BVT14225 showed IC50s of 100 nM and 500 nM, respectively, for the 11b-HSD1 dehydrogenase assay.

EDTA refers to ethylenediaminetetraacetic acid.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound of the formula:

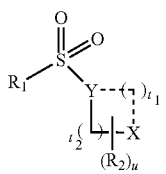

wherein:

$t_1$ is 2;

$t_2$ is 2;

u is selected from the group consisting of 0, 1, 2, 3, 4, 5, 6, 7, 8, 9 and 10;

X is $NR_3$;

Y is N;

$R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted, wherein the hetero$(C_{3-12})$bicycloalkyl or hetero$(C_{4-12})$bicycloaryl is selected from the group consisting of:

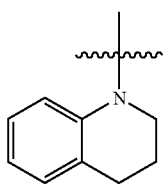 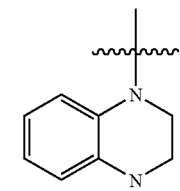 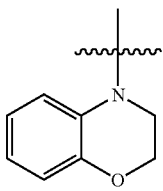

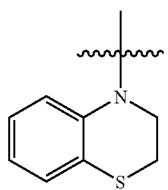 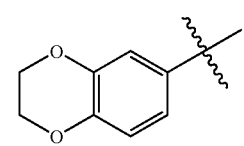

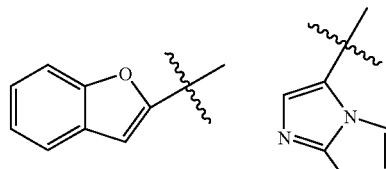

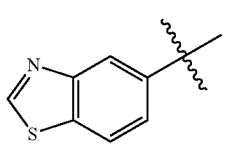 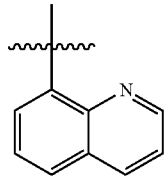

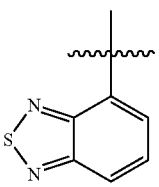 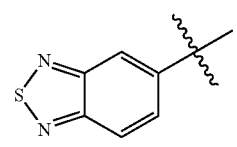

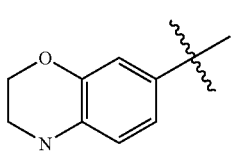 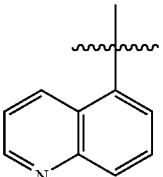

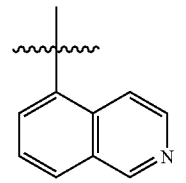 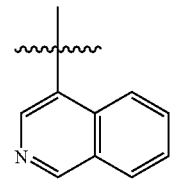

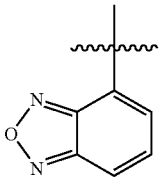 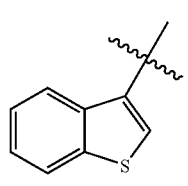

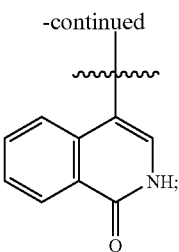

with the proviso that $R_1$ is not an alk-4-yl-phenyl when Y is N;

$R_2$ is selected from the group consisting of hydrogen, nitro, cyano, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group; and $R_3$ is selected from the group consisting of hydrogen, nitro, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo $(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring;

wherein the substituents are selected from the group consisting of aldehyde, alicyclic, aliphatic, $(C_{1-10})$alkyl, alkylene, alkylidene, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, nitro, oxaalkyl, and oxoalkyl moieties.

2. The compound according to claim 1, wherein $R_1$ is selected from the group consisting of:

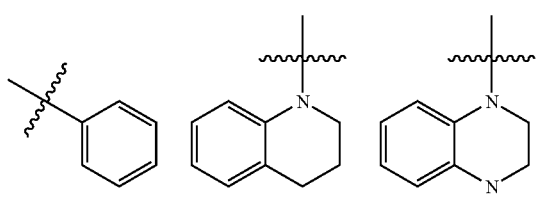

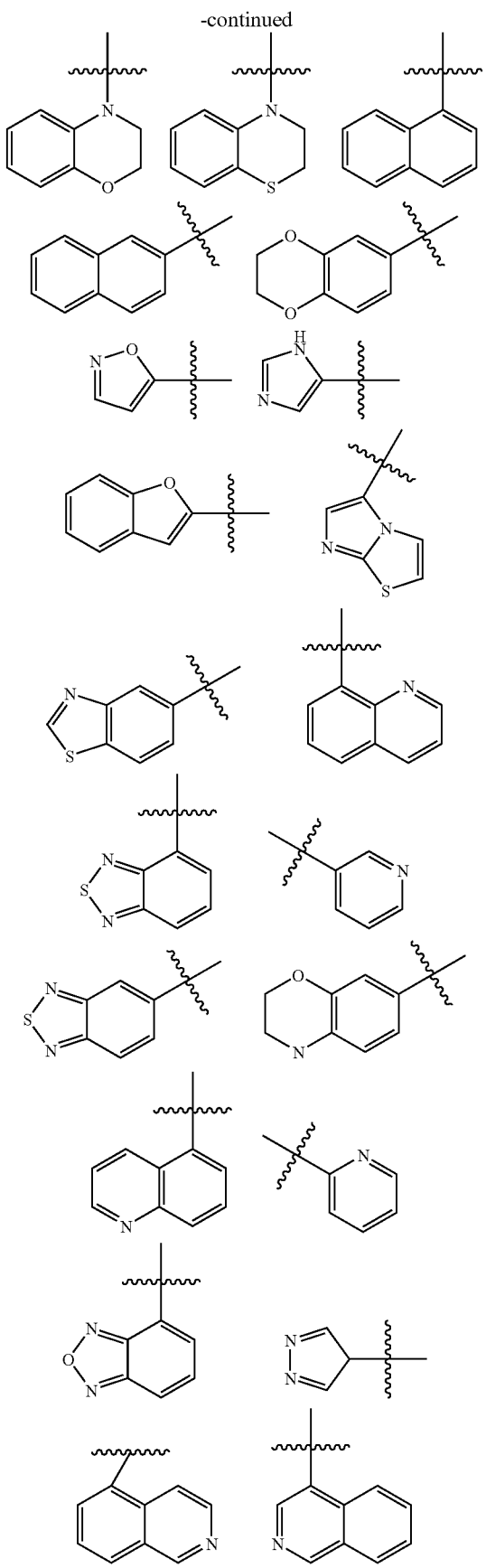

-continued

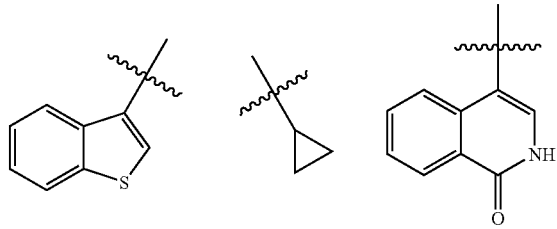

wherein R₁ is unsubstituted or substituted.

3. The compound according to claim 1, wherein R₁ is selected from the group consisting of:

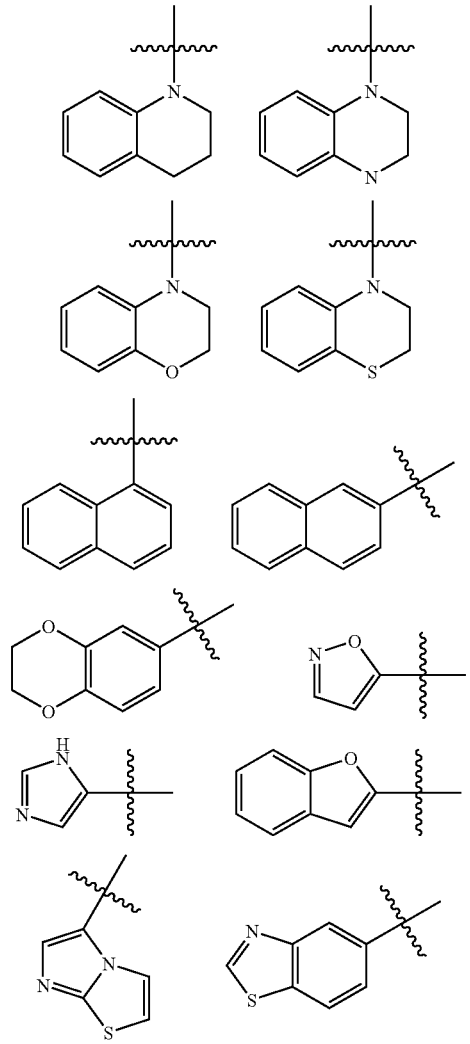

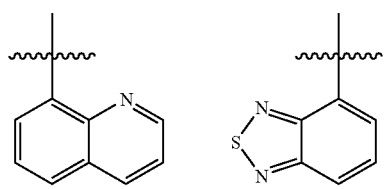

-continued

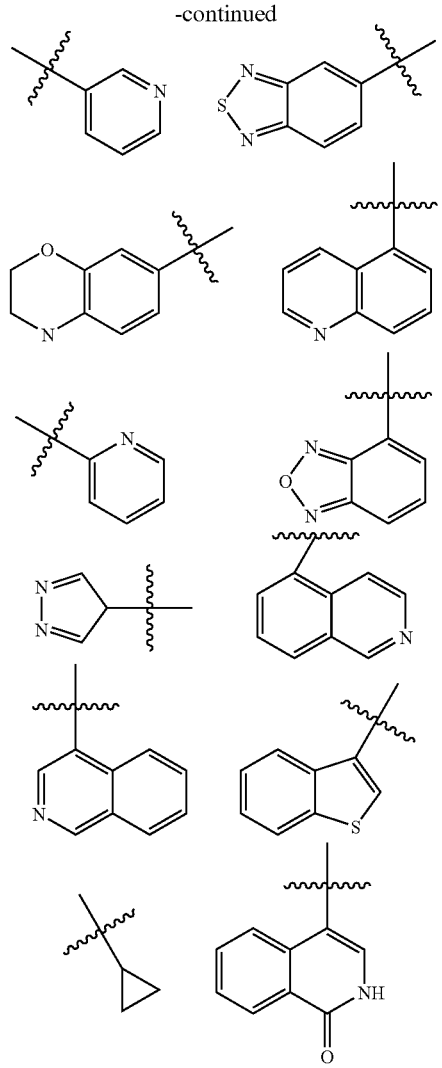

wherein R₁ is unsubstituted or substituted.

4. The compound according to claim 1, wherein R₂ is selected from the group consisting of halo, alkoxy, $(C_{1-3})$ alkyl, halo$(C_{1-3})$alkyl, $(C_{3-6})$cycloalkyl, dialkylamino and cycloamino, each substituted or unsubstituted.

5. The compound according to claim 1, wherein R₂ is selected from the group consisting of —CH₃, cyclopropyl, —F, —CF₃ and —OCH₃, each substituted or unsubstituted.

6. The compound according to claim 1, wherein R₃ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, aryl, heteroaryl, $(C_{9-12})$bicycloaryl, and hetero$(C_{4-12})$bicycloaryl, each substituted or unsubstituted.

7. The compound according to claim 1, wherein R₃ is:

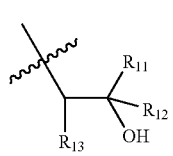

wherein:

R₁₁ is selected from the group consisting of hydrogen, nitro, cyano, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl(C₁₋₁₀)alkyl, heteroaryl(C₁₋₅)alkyl, perhalo(C₁₋₁₀)alkyl, (C₃₋₁₂)cycloalkyl(C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, aryl, heteroaryl, (C₉₋₁₂)bicycloaryl, and hetero(C₄₋₁₂)bicycloaryl, each substituted or unsubstituted;

R₁₂ is selected from the group consisting of hydrogen, nitro, cyano, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl(C₁₋₁₀)alkyl, heteroaryl(C₁₋₅)alkyl, perhalo(C₁₋₁₀)alkyl, (C₃₋₁₂)cycloalkyl(C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, aryl, heteroaryl, (C₉₋₁₂)bicycloaryl, and hetero(C₄₋₁₂)bicycloaryl, each substituted or unsubstituted, or R₁₁ and R₁₂ are taken together to form a ring; and R₁₃ is selected from the group consisting of hydrogen, nitro, cyano, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl(C₁₋₁₀)alkyl, heteroaryl(C₁₋₅)alkyl, perhalo(C₁₋₁₀)alkyl, (C₃₋₁₂)cycloalkyl(C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, aryl, heteroaryl, (C₉₋₁₂)bicycloaryl, and hetero(C₄₋₁₂)bicycloaryl, each substituted or unsubstituted.

8. The compound according to claim 1, wherein R₃ is:

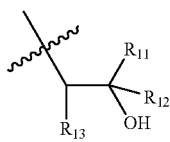

wherein:

R₁₁ is selected from the group consisting of hydrogen, —CH₃; —CH₂CH₃; —CH(CH₃)₂; —CH₂CH(CH₃)₂; —CH₂C(CH₃)H₂; -Ph; —CH₂Ph; spiro-cyclobutyl; or spiro-cyclopentyl, each substituted or unsubstituted;

R₁₂ is selected from the group consisting of hydrogen and methyl, substituted or unsubstituted; and R₁₃ is selected from the group consisting of hydrogen, propyl, cyclopropyl, spiro-cyclopropyl, butyl, spiro-cyclobutyl, spiro-cyclopentyl, benzyl, and phenyl, each substituted or unsubstituted.

9. The compound according to claim 1, wherein R₃ is selected from the group consisting of methyl, cyclopropyl, cyclobutyl, cyclopentyl, phenyl, pyridyl, pyrimidyl, thiazolyl, and adamantly, each substituted or unsubstituted.

10. The compound according to claim 1, wherein R₃ is:

wherein R₁₄ is selected from the group consisting of hydrogen, nitro, cyano, hydroxy, alkoxy, aryloxy, heteroaryloxy, carbonyl, amino, (C₁₋₁₀)alkylamino, sulfonamido, imino, sulfonyl, sulfinyl, (C₁₋₁₀)alkyl, (C₃₋₁₂)cycloalkyl, hetero(C₃₋₁₂)cycloalkyl, (C₉₋₁₂)bicycloalkyl, hetero(C₃₋₁₂)bicycloalkyl, aryl(C₁₋₁₀)alkyl, heteroaryl(C₁₋₅)alkyl, perhalo(C₁₋₁₀)alkyl, (C₃₋₁₂)cycloalkyl(C₁₋₁₀)alkyl, halo(C₁₋₁₀)alkyl, carbonyl(C₁₋₃)alkyl, thiocarbonyl(C₁₋₃)alkyl, sulfonyl(C₁₋₃)alkyl, sulfinyl(C₁₋₃)alkyl, amino (C₁₋₁₀)alkyl, imino(C₁₋₃)alkyl, aryl, heteroaryl, (C₉₋₁₂)bicycloaryl, and hetero(C₄₋₁₂)bicycloaryl, each substituted or unsubstituted.

11. The compound according to claim 10, wherein R₁₄ is selected from the group consisting of (C₁₋₆)alkyl, halo(C₁₋₆)alkyl, and aminocarbonyl, each substituted or unsubstituted.

12. The compound according to claim 1, wherein R₃ is a substituted or unsubstituted phenyl.

13. The compound according to claim 12, wherein R₃ is a phenyl substituted with a substituent selected from the group consisting of hydroxy, halo, alkoxy, carbonyl, nitro, and amino, each substituted or unsubstituted.

14. A compound of the formula:

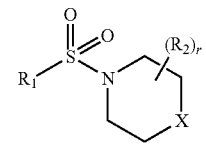

wherein:

r is selected from the group consisting of 0, 1, 2, 3, 4, 5, 6, 7 and 8;

X is NR₃;

R₁ is selected from the group consisting of (C₃₋₁₂)cycloalkyl, hetero(C₃₋₁₂)cycloalkyl, (C₉₋₁₂)bicycloalkyl, hetero(C₃₋₁₂)bicycloalkyl, aryl, heteroaryl, (C₉₋₁₂)bicycloaryl, and hetero(C₄₋₁₂)bicycloaryl, wherein the hetero(C₃₋₁₂)bicycloalkyl or hetero(C₄₋₁₂)bicycloaryl is selected from the group consisting of:

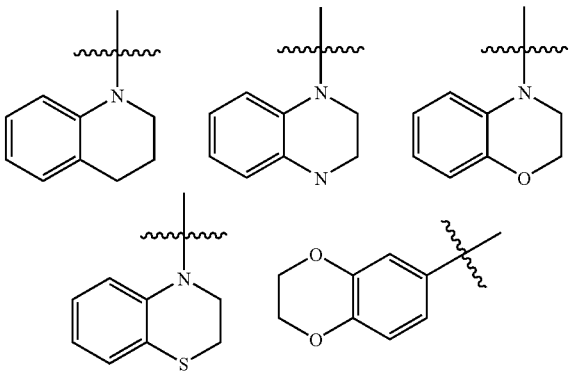

-continued

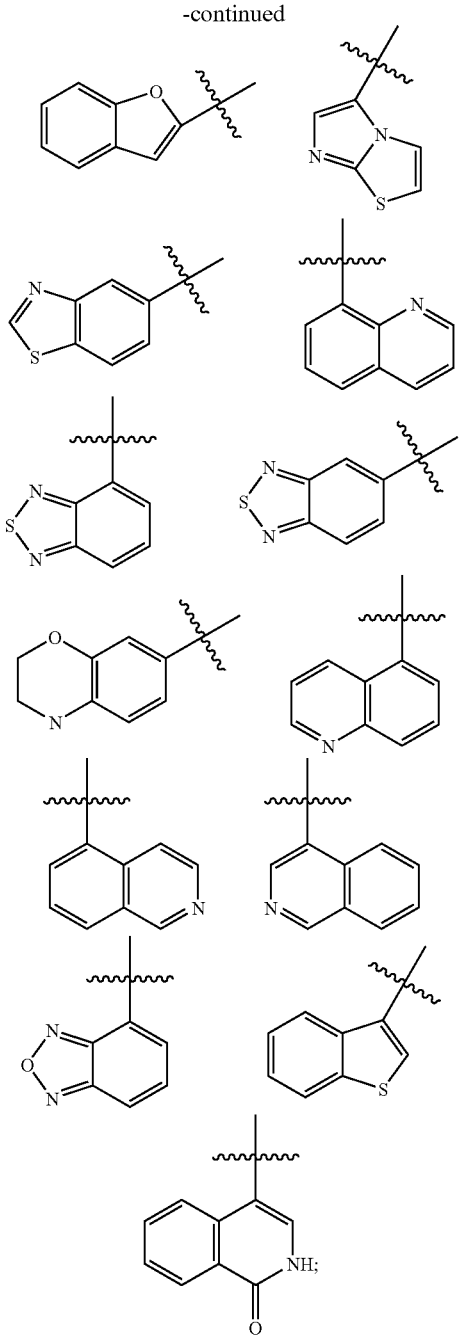

each substituted or unsubstituted, with the proviso that R₁ is not an alk-4-yl-phenyl;

R$_2$ is selected from the group consisting of hydrogen, nitro, cyano, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, aryl, heteroaryl, ($C_{9-12}$)bicycloaryl, and hetero($C_{4-12}$)bicycloaryl, each substituted or unsubstituted, or two R$_2$ are taken together to form a ring, or two R$_2$ are attached to the same atom and taken together to form an oxo group; and R$_3$ is selected from the group consisting of hydrogen, nitro, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo ($C_{1-10}$)alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or R$_2$ and R$_3$ are taken together to form a ring;

wherein the substituents are selected from the group consisting of aldehyde, alicyclic, aliphatic, ($C_{1-140}$) alkyl, alkylene, alkylidene, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, nitro, oxaalkyl, and oxoalkyl moieties.

15. The compound according to claim 14 of the formula:

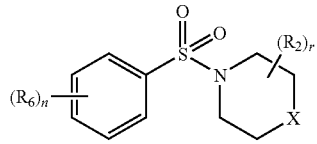

wherein:
r is selected from the group consisting of 0, 1, 2, 3, 4, 5, 6, 7 and 8;
n is selected from the group consisting of 1, 2, 3, 4 and 5;
X is NR$_3$;
R$_2$ is selected from the group consisting of hydrogen, nitro, cyano, hydroxy, alkoxy, aryloxy, heteroaryloxy, carbonyl, amino, ($C_{1-10}$alkylamino, sulfonamido, imino, sulfonyl, sulfinyl, ($C_{1-10}$alkyl, ($C_{3-12}$cycloalkyl, hetero($C_{3-12}$cycloalkyl, ($C_{9-12}$bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$) alkyl, sulfinyl($C_{1-3}$)alkyl, amino ($C_{1-10}$)alkyl, imino ($C_{1-3}$)alkyl, aryl, heteroaryl, ($C_{9-12}$)bicycloaryl, and hetero($C_{4-12}$)bicycloaryl, each substituted or unsubstituted, or two R$_2$ are taken together to form a ring, or two R$_2$ are attached to the same atom and taken together to form an oxo group;

R$_3$ is selected from the group consisting of hydrogen, nitro, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo ($C_{1-10}$alkyl, carbonyl($C_{1-3}$)alkyl, thiocarbonyl($C_{1-3}$) alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_3$ are taken together to form a ring; and each $R_6$ is independently selected from the group consisting of hydrogen, nitro, cyano, hydroxy, carboxy, alkoxy, aryloxy, heteroaryloxy, carbonyl, amino, carboxamido, $(C_{1-10})$alkylamino, sulfonamido, imino, sulfonyl, sulfinyl, $(C_{1-10})$alkyl, $(C_{3-12})$cycloalkyl, hetero$(C_{3-42})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-13})$alkyl, sulfinyl$(C_{1-3})$alkyl, amino $(C_{1-10})$alkyl, imino$(C_{1-3})$alkyl, aryl, heteroaryl, $(C_{9-42})$bicycloaryl, and hetero$(C_{4-12})$bicycloaryl, each substituted or unsubstituted, or two $R_6$ are taken together to form a ring, with the proviso that $R_6$ is not an alk-4-yl.

16. The compound according to claim 15, wherein $R_6$ is selected from the group consisting of halo, cyano, alkoxy, aryloxy, $(C_{1-6})$alkyl, and aryl, each substituted or unsubstituted.

17. The compound according to claim 14 of the formula:

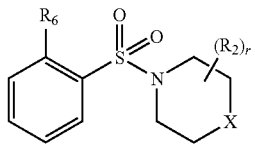

wherein:
r is selected from the group consisting of 0, 1, 2, 3, 4, 5, 6, 7 and 8;
X is $NR_3$;
$R_2$ is selected from the group consisting of hydrogen, nitro, cyano, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;
$R_3$ is selected from the group consisting of hydrogen, nitro, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring; and
$R_6$ is selected from the group consisting of hydrogen, nitro, cyano, hydroxy, carboxy, alkoxy, aryloxy, heteroaryloxy, carbonyl, amino, carboxamido, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_9)_{-12})$bicycloaryl, and hetero$(C_{4-12})$bicycloaryl, each substituted or unsubstituted.

18. The compound according to claim 17, wherein $R_6$ is selected from the group consisting of halo, cyano, alkoxy, aryloxy, $(C_{1-6})$alkyl, and aryl, each substituted or unsubstituted.

19. The compound according to claim 14 of the formula:

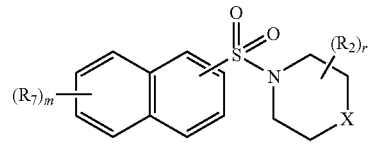

wherein:
r is selected from the group consisting of 0, 1, 2, 3, 4, 5, 6, 7 and 8;
m is selected from the group consisting of 0, 1, 2, 3, 4, 5, 6 and 7;
X is $NR_3$;
$R_2$ is selected from the group consisting of hydrogen, nitro, cyano, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or two $R_2$ are taken together to form a ring, or two $R_2$ are attached to the same atom and taken together to form an oxo group;
$R_3$ is selected from the group consisting of hydrogen, nitro, hydroxy, alkoxy, aryloxy, heteroaryloxy, carbonyl, amino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$(C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, aryl, heteroaryl, $(C_{9-12})$bicycloaryl, and hetero$(C_{4-12})$bicycloaryl, each substituted or unsubstituted, or $R_2$ and $R_3$ are taken together to form a ring; and
each $R_7$ is independently selected from the group consisting of hydrogen, nitro, cyano, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, aryl$(C_{1-10})$alkyl, heteroaryl$(C_{1-5})$alkyl, perhalo$((C_{1-10})$alkyl, $(C_{3-12})$cycloalkyl$(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_7$ are taken together to form a ring.

20. The compound according to claim 19, wherein $R_7$ is selected from the group consisting of ($C_{1-6}$)alkyl and amino, each substituted or unsubstituted.

21. The compound according to claim 14 of the formula:

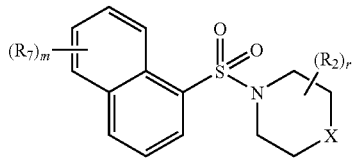

wherein:
r is selected from the group consisting of 0, 1, 2, 3, 4, 5, 6, 7 and 8;
m is selected from the group consisting of 0, 1, 2, 3, 4, 5, 6 and 7;
X is $NR_3$;
$R_2$ is selected from the group consisting of hydrogen, nitro, cyano, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;
$R_3$ is selected from the group consisting of hydrogen, nitro, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_3$ are taken together to form a ring; and
each $R_7$ is independently selected from the group consisting of hydrogen, nitro, cyano, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_1$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_7$ are taken together to form a ring.

22. The compound according to claim 21, wherein $R_7$ is selected from the group consisting of ($C_{1-6}$)alkyl and amino, each substituted or unsubstituted.

23. The compound according to claim 14 of the formula:

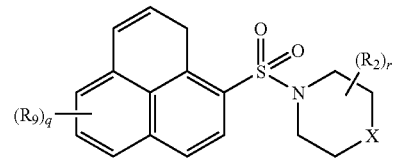

wherein:
r is selected from the group consisting of 0, 1, 2, 3, 4, 5, 6, 7 and 8;
q is selected from the group consisting of 0, 1, 2, 3, 4, 5, 6, 7, 8 and 9;
X is $NR_3$;
$R_2$ is selected from the group consisting of hydrogen, nitro, cyano, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo($C_{1-10}$)alkyl, carbonyl ($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, aryl, heteroaryl, ($C_{9-12}$)bicycloaryl, and hetero($C_{4-12}$)bicycloaryl, each substituted or unsubstituted, or two $R_2$ are taken together to form a ring, or two $R_2$ are attached to the same atom and taken together to form an oxo group;
$R_3$ is selected from the group consisting of hydrogen, nitro, hydroxy, alkoxy, aryloxy, heteroaryloxy, carbonyl, amino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo ($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or $R_2$ and $R_3$ are taken together to form a ring; and
each $R_9$ is independently selected from the group consisting of hydrogen, nitro, cyano, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, aryl($C_{1-10}$)alkyl, heteroaryl($C_{1-5}$)alkyl, perhalo($C_{1-10}$)alkyl, ($C_{3-12}$)cycloalkyl($C_{1-10}$)alkyl, halo ($C_{1-10}$)alkyl, carbonyl($C_{1-3}$)alkyl, thiocarbonyl ($C_1$)$_{-3}$)alkyl, sulfonyl($C_{1-3}$)alkyl, sulfinyl($C_{1-3}$)alkyl, amino ($C_{1-10}$)alkyl, imino($C_{1-3}$)alkyl, aryl, heteroaryl, ($C_{9-12}$)bicycloaryl, and hetero($C_{4-12}$)bicycloaryl, each substituted or unsubstituted, or two $R_9$ are taken together to form a ring.

24. A compound selected from the group consisting of:
1-Phenyl-4-(m-tolylsulfonyl)piperazine;
1-(3-Methoxyphenylsulfonyl)-4-phenylpiperazine;
1-(3-Phenoxyphenylsulfonyl)-4-phenylpiperazine;

1-(3-Chloro-2-methylphenylsulfonyl)-4-phenylpiperazine;
1-(4-Phenoxyphenylsulfonyl)-4-phenylpiperazine;
1-(4-Methoxyphenylsulfonyl)-4-phenylpiperazine;
1-(2,4-Dimethoxy-benzenesulfonyl)-4-phenyl-piperazine;
N-[4-(4-Phenyl-piperazine-1-sulfonyl)-phenyl]-acetamide;
1-(2-Chloro-6-methyl-benzenesulfonyl)-4-phenyl-piperazine;
1-(2,6-Dichloro-benzenesulfonyl)-4-phenyl-piperazine;
1-(2-Chloro-4-fluoro-benzenesulfonyl)-4-phenyl-piperazine;
1-(2,3-Dichloro-benzenesulfonyl)-4-phenyl-piperazine;
1-(2,4-Dichloro-benzenesulfonyl)-4-phenyl-piperazine;
2-(4-phenylpiperazin-1-ylsulfonyl)benzonitrile;
4-(4-phenylpiperazin-1-ylsulfonyl)benzonitrile;
1-(2-chlorophenylsulfonyl)-4-phenylpiperazine;
1-(3-chlorophenylsulfonyl)-4-phenylpiperazine;
1-Phenyl-4-(o-tolylsulfonyl)piperazine;
1-(2,5-Difluorophenylsulfonyl)-4-phenylpiperazine;
1-(3-Chloro-2-fluorophenylsulfonyl)-4-phenylpiperazine;
3-(4-Phenylpiperazin-1-ylsulfony)benzonitrile;
1-(2-Fluorophenylsulfonyl)-4-phenylpiperazine;
1-(2-Bromophenylsulfonyl)-4-phenylpiperazine;
2-(4-(2-Chlorophenylsulfonyl)piperazin-1-yl)phenol;
2-(4-(3-Chlorophenylsulfonyl)piperazin-1-yl)phenol;
1-(2-Chlorophenyl)-4-(2-chlorophenylsulfonyl)piperazine;
1-(3-Chlorophenyl)-4-(2-chlorophenylsulfonyl)piperazine;
1-(4-Chlorophenyl)-4-(2-chlorophenylsulfonyl)piperazine;
1-(2-Chlorophenylsulfonyl)-4-(2-methoxyphenyl)piperazine;
(1R,4S)-2-(4-Chlorophenyl)-5-(2-chlorophenylsulfonyl)-2,5-diaza-bicyclo [2.2.1]heptane;
4-(4-(2-Chlorophenylsulfonyl)piperazin-1-yl)benzaldehyde;
4-(4-(2-Chlorophenylsulfonyl)piperazin-1-yl)phenol;
1-(4-(4-(2-Chlorophenylsulfonyl)piperazin-1-yl)phenyl)ethanone;
1-(2-Chlorophenylsulfonyl)-4-(2-nitrophenyl)piperazine;
1-(2-Chlorophenylsulfonyl)-4-(3-nitrophenyl)piperazine;
1-(2-Chlorophenylsulfonyl)-4-(4-nitrophenyl)piperazine;
2-(4-(2-Chlorophenylsulfonyl)piperazin-1-yl)benzenamine;
2-(4-(2-Chlorophenylsulfonyl)piperazin-2-yl)benzenamine;
2-(4-(2-Chlorophenylsulfonyl)piperazin-1-yl)benzoic acid;
2-(4-(2-Chlorophenylsulfonyl)piperazin-1-yl)benzamide;
1-(2-Chlorophenylsulfonyl)-4-(pyridin-2-yl)piperazine;
1-(2-Chlorophenylsulfonyl)-4-(5-chloropyridin-2-yl)piperazine;
1-(2-Chlorophenylsulfonyl)-4-(3-nitropyridin-2-yppiperazine;
3[4-(2-Chloro-benzenesulfonyl)piperazin-1yl]-pyridin-2-ol;
2-(4-(2-Chlorophenylsulfonyl)piperazin-1-yl)pyrimidine;
1-(2-Chlorophenylsulfonyl)-4-(5-nitrothiazol-2-yl)piperazine;
2-(4-(2-chlorophenylsulfonyl)piperazin-1-yl)thiazole-4-carboxylic acid;
2-(4-(2-Chlorophenylsulfonyl)piperazin-1-yl)thiazole-4-carboxamide;
(2-(4-(2-Chlorophenylsulfonyl)piperazin-1-yl)thiazol-4-yl)methanol;
1-(2-Chlorophenylsulfonyl)-4-1'-adamantylpiperazine
tert-Butyl 2-(4-(4-chlorophenylsulfonyl)-2-oxopiperazin-1-y)acetate;
1-(2-Chlorophenylsulfonyl)-4-cyclopentylpiperazine;
1-(2-chlorophenylsulfonyl)-4-cyclohexylpiperazine;
1-(2-Chlorophenylsulfonyl)piperazine;
1-Benzyl-4-(2-chlorophenylsulfonyl)piperazin-2-one;
4-(4-(2-Chlorophenylsulfonyl)piperazin-1-yl)-1H-indole;
7-(4-(2-Chlorophenylsulfonyl)piperazin-1-yl)-1H-indazole;
4-(4-(2-Chlorophenylsulfonyl)piperazin-1-yl)-1H-indazole;
Trans-2-(4-(2-chlorophenylsulfonyl)piperazin-1-yl)cyclopentanol;
Trans-2-(4-(2-chlorophenylsulfonyl)piperazin-1-yl)cyclohexanol;
1-(2-Chlorophenylsulfonyl)-4-(1-methylcyclopropyl)piperazine;
1-(3-Chloro-2-methylphenylsulfonyl)-4-(1-methylcyclopropyl)piperazine;
1-(2-Chloro-6-methylphenylsulfonyl)-4-(1-methylcyclopropyl)piperazine;
1-(2-Chloro-4-fluorophenylsulfonyl)-4-(1-methylcyclopropyl)piperazine;
1-(4-Bromo-2-chlorophenylsulfonyl)-4-(1-methylcyclopropyl)piperazine;
1-(1-Methylcyclopropyl)-4-(2-(trifluoromethyl)phenylsulfonyl)piperazine;
3-Chloro-4-(4-(1-methylcyclopropyl)piperazin-1-ylsulfonyl)benzonitrile;
1-(4-Bromo-2-methylphenylsulfonyl)-4-(1-methylcyclopropyl)piperazine;
1-(4-Bromo-2-(trifluoromethyl)phenylsulfonyl)-4-(1-methylcyclopropyl) piperazine;
4-(4-(1-Methylcyclopropyl)piperazin-1-ylsulfonyl)benzonitrile;
1-(4-Isopropoxyphenylsulfonyl)-4-(1-methylcyclopropyl)piperazine;
1-(4-(Difluoromethoxy)phenylsulfonyl)-4-(1-methylcyclopropyppiperazine;
1-(3-(Difluoromethoxy)phenylsulfonyl)-4-(1-methylcyclopropyl)piperazine;
1-(1-Methylcyclopropyl)-4-(perfluorophenylsulfonyl) piperazine;
(1-(4-(2-chlorophenylsulfonyl)piperazin-1-yl)cyclobutyl) methanol;
Ethyl 1-(4-(2-chlorophenylsulfonyl)piperazin-1-yl)cyclopropanecarboxylate;
(R)-4-(2-chlorophenylsulfonyl)-2-methyl-1-(1-methylcyclopropyl) piperazine;
(R)-4-(2-chlorophenylsulfonyl)-2-methyl-1-(1-methylcyclopropyl) piperazine;
(R)-1-(2-chlorophenylsulfonyl)-2-methyl-4-(1-methylcyclopropyl) piperazine;
2-(4-(1-methylcyclopropyl)piperazin-1-ylsulfonyl)benzonitrile;
4-benzyl-7-(2-chlorophenylsulfonyl)-4,7-diazaspiro [2.5] octane ;
1-(2-chlorophenylsulfonyl)-4-cyclopropylpiperazine;
1-(2-Chloro-benzenesulfonyl)-4-(1-fluoromethyl-cyclopropyl)-piperazine;
1-(2-Chloro-benzenesulfonyl)-4-(1-trifluoromethyl-cyclopropyl)-piperazine;
1-[4-(2-Chloro-benzenesulfonyl)-piperazin-1-yl]-cyclopropanecarboxylic acid amide;

2[4-(2-Chloro-benzenesulfonyl)-piperazin-1-yl]-2-cyclopropyl-ethanol;

7-(2-Chloro-benzenesulfonyl)-4-(1-methyl-cyclopropyl)-4,7-diaza-spiro[2.5]octane;

1-(2-Chloro-benzenesulfonyl)-2,5-dimethyl-4-(1-methyl-cyclopropyl)-piperazine;

2-(2-Chloro-benzenesulfonyl)-5-(1-methyl-cyclopropyl)-2,5-diaza-bicyclo[2.2.2]octane;

1-(4-Chlorophenylsulfonyl)-4-phenylpiperazine;

tert-Butyl 4-(2-chlorophenylsulfonyl)piperazine-1-carboxylate; and 1-(2-Chlorophenylsulfonyl)-4-methylpiperazine.

25. The compound according to claim 1, wherein the compound is in the form of a pharmaceutically acceptable salt.

26. The compound according to claim 1, wherein the compound is present in a mixture of stereoisomers.

27. The compound according to claim 1, wherein the compound comprises a single stereoisomer.

28. A pharmaceutical composition comprising as an active ingredient a compound according to claim 1.

29. The pharmaceutical composition according to claim 28, wherein the composition is a solid formulation adapted for oral administration.

30. The pharmaceutical composition according to claim 28, wherein the composition is a liquid formulation adapted for oral administration.

31. The pharmaceutical composition according to claim 28, wherein the composition is a tablet.

32. The pharmaceutical composition according to claim 28, wherein the composition is a liquid formulation adapted for parenteral administration.

33. A pharmaceutical composition comprising a compound according to claim 1, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: DNA sequence encoding PCR Primer hsd1_24-f
```

```
<400> SEQUENCE: 1
aacgaggaat tcagaccaga gatg                                24

<210> SEQ ID NO 2
<211> LENGTH: 24
<212> TYPE: DNA
<213> ORGANISM: Artificial
<220> FEATURE:
<223> OTHER INFORMATION: DNA sequence encoding PCR Primer hsd1-292-r

<400> SEQUENCE: 2
ttacttgttt atgaatctgt ccat                                24
```